United States Patent
Wang et al.

(10) Patent No.: US 8,420,363 B2
(45) Date of Patent: Apr. 16, 2013

(54) IMPEDANCE BASED DEVICES AND METHODS FOR USE IN ASSAYS

(75) Inventors: Xiaobo Wang, San Diego, CA (US); Xiao Xu, San Diego, CA (US)

(73) Assignee: Acea Biosciences, Inc., San Diego, CA (US)

( * ) Notice: Subject to any disclaimer, the term of this patent is extended or adjusted under 35 U.S.C. 154(b) by 33 days.

(21) Appl. No.: 12/325,530

(22) Filed: Dec. 1, 2008

(65) Prior Publication Data

US 2009/0205201 A1    Aug. 20, 2009

Related U.S. Application Data

(62) Division of application No. 10/705,447, filed on Nov. 10, 2003, now Pat. No. 7,470, 533.

(60) Provisional application No. 60/435,400, filed on Dec. 20, 2002, provisional application No. 60/469,572, filed on May 9, 2003.

(51) Int. Cl.
*C12N 13/00* (2006.01)
*B05D 3/00* (2006.01)

(52) U.S. Cl.
USPC ...... 435/173.1; 435/4; 435/285.2; 435/287.1; 427/532; 427/554; 427/555

(58) Field of Classification Search ........... 435/4, 173.1, 435/285.2, 287.1; 427/532, 554, 555
See application file for complete search history.

(56) References Cited

U.S. PATENT DOCUMENTS

| | | | | |
|---|---|---|---|---|
| 5,981,268 | A | * | 11/1999 | Kovacs et al. ............... 435/287.1 |
| 6,033,628 | A | * | 3/2000 | Kaltenbach et al. .......... 422/68.1 |
| 6,132,683 | A | * | 10/2000 | Sugihara et al. ............ 422/82.01 |
| 6,280,586 | B1 | * | 8/2001 | Wolf et al. ...................... 257/253 |
| 6,686,193 | B2 | * | 2/2004 | Maher et al. ................ 435/285.2 |
| 7,553,448 | B2 | * | 6/2009 | Kumar et al. ..................... 422/52 |
| 2004/0022677 | A1 | * | 2/2004 | Wohlstadter et al. ........... 422/52 |
| 2006/0216203 | A1 | * | 9/2006 | Fuller et al. ................. 422/82.01 |
| 2008/0314882 | A1 | * | 12/2008 | Bhullar et al. ............ 219/121.69 |

* cited by examiner

*Primary Examiner* — Nathan Bowers
(74) *Attorney, Agent, or Firm* — Biotech Beach Law Group PC

(57) ABSTRACT

A device for detecting cells and/or molecules on an electrode surface is disclosed. The device detects cells and/or molecules through measurement of impedance changes resulting from the cells and/or molecules. A disclosed embodiment of the device includes a substrate having two opposing ends along a longitudinal axis. A plurality of electrode arrays are positioned on the substrate. Each electrode array includes at least two electrodes, and each electrode is separated from at least one adjacent electrode in the electrode array by an expanse of non-conductive material. The electrode has a width at its widest point of more than about 1.5 and less than about 10 times the width of the expanse of non-conductive material. The device also includes electrically conductive traces extending substantially longitudinally to one of the two opposing ends of the substrate without intersecting another trace. Each trace is in electrical communication with at least one of the electrode arrays.

14 Claims, 58 Drawing Sheets

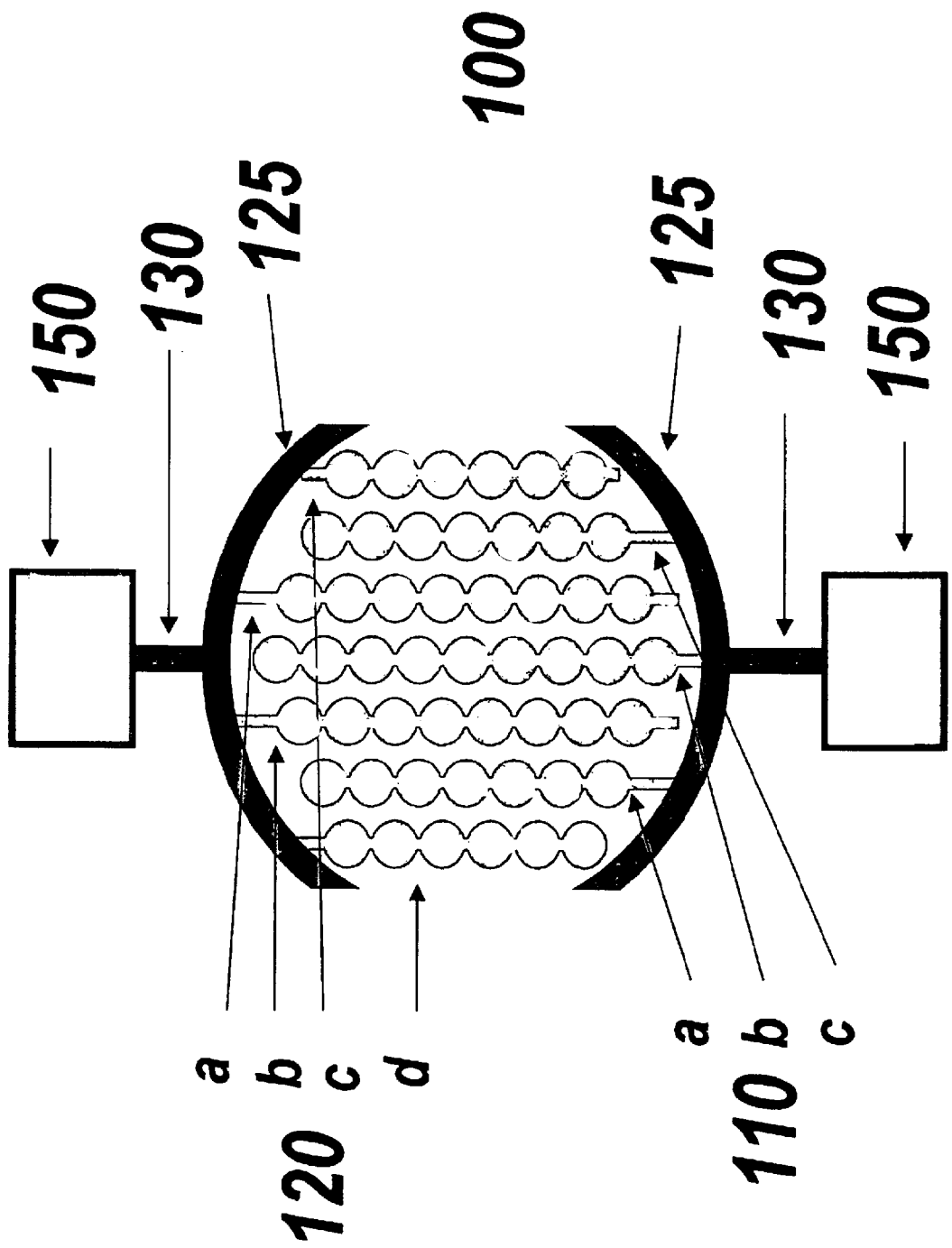

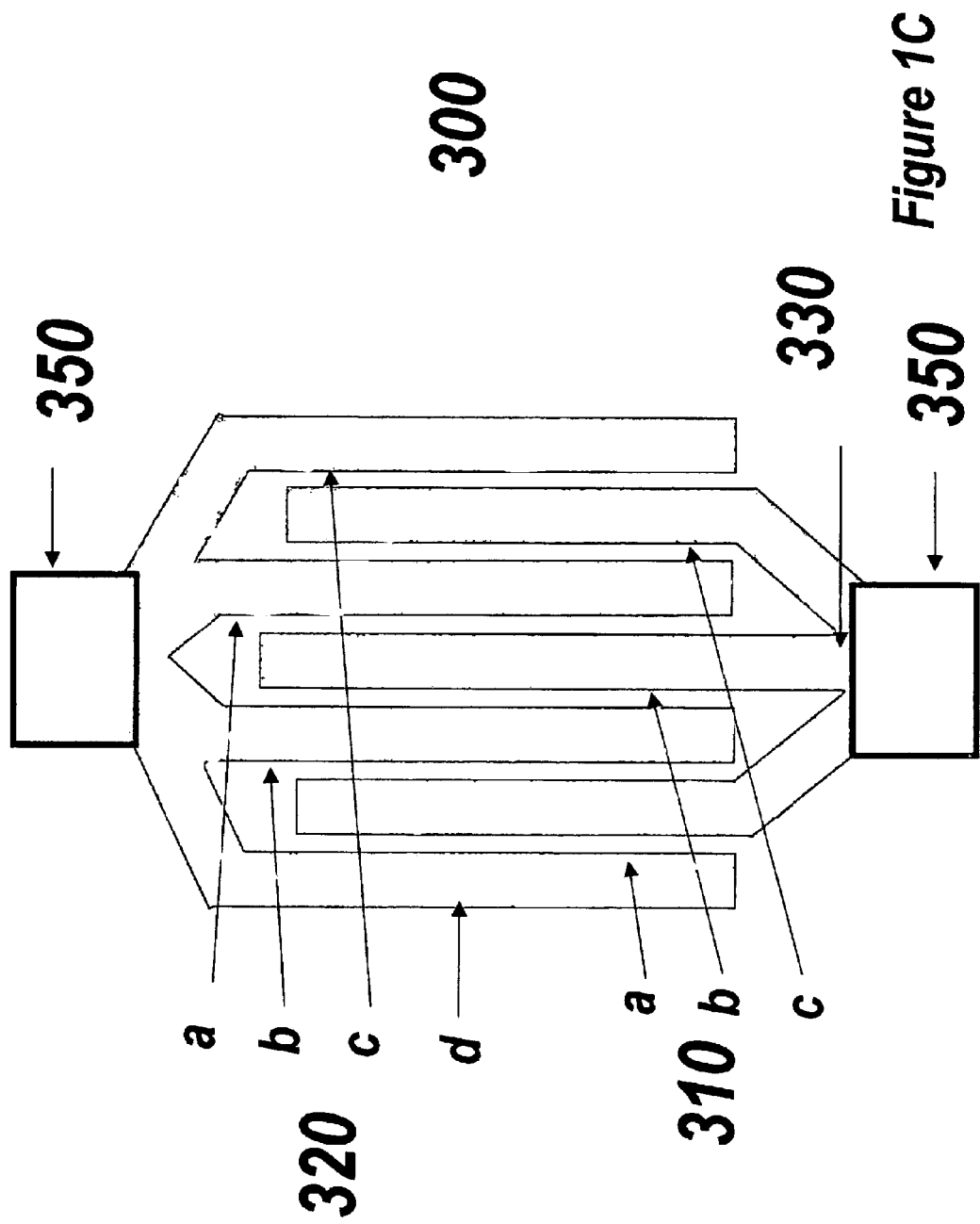

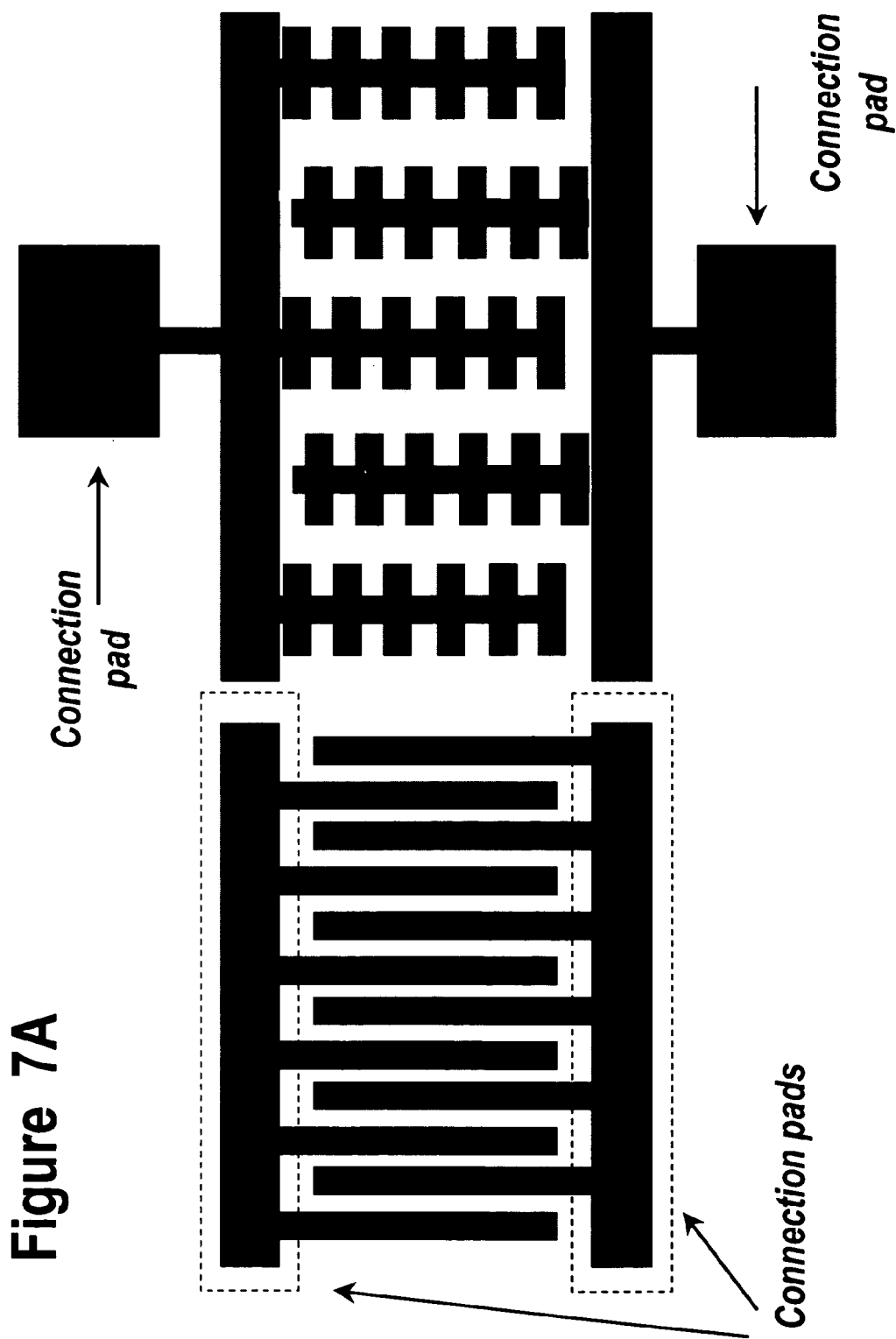

Concentric electrode structures

Connection pads

Figure 8.

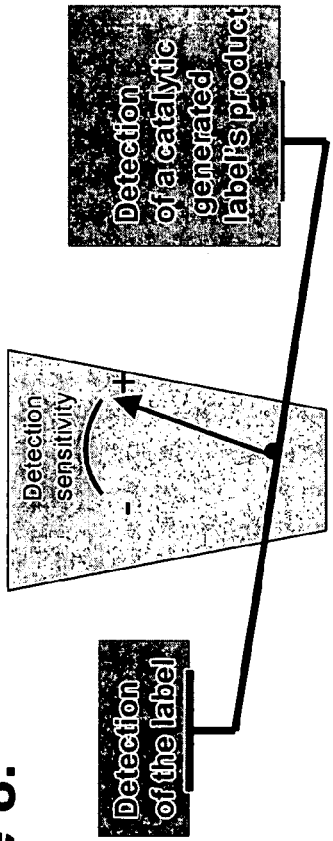

Signal amplification for improved detection sensitivity by indirect measuring catalytic products of enzyme-mediated reactions. Examples of enzymes commonly used include alkaline phosphatase (AP) and horseradish peroxidase (HRP). Here are some typical reactions used.

| Enzyme | Reagents | Reaction |
|---|---|---|
| HRP | 4-chloro-1-napthol (4CN) | Oxidized products form purple precipitate |
| HRP | 3,3'-diaminobenzidine (DAB, with or without NiCl$_2$) | Forms dark brown precipitate |
| HRP | 3,3',5,5'-tetramethylbenzidine (TMB) | Forms dark purple stain |
| AP | 5-bromo-4-chloro-3-indolyl phosphate (BCIP)/nitroblue tetrazolium (NBT) | BCIP hydrolysis products indigo percipitate after oxidation with NBT; reduced NBT precipitates, dark blue-gray stain results |

|  | Resistance (ohm) |
|---|---|
| t0 | 82 |
| t8min | 801 |
| t13min | 1263 |
| t28min | 1825 |
| t80min | 1881 |
| t17h | 1841 |

| Fibronectin | Resistance Fold Change |
|---|---|
| 0 | 0.49 |
| 50pg | 1.28 |
| 500pg | 8.66 |
| 5ng | 14.67 |

← — — — — Electronic conductor lines

POGO-Pins or
POGO-Pin like
structures

Electronic
conductor
lines

Metal clip type A

Connection pads on substrate

Electrode structures

Metal clip type B

Connection pads on substrate

Electrode structures

Printed Circuit Board

Electrode strip

**Measurement unit
(Electrode structure unit)**

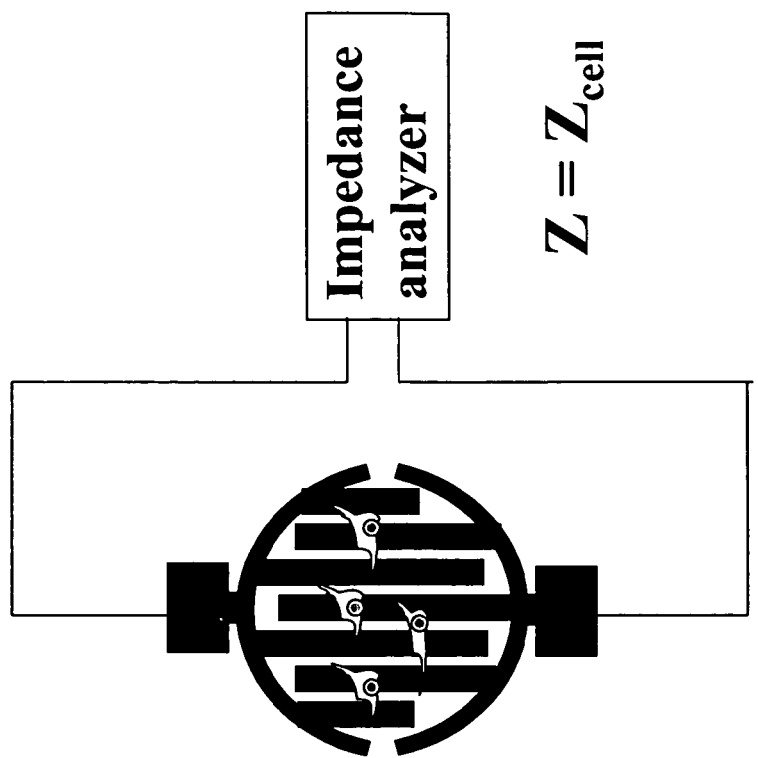
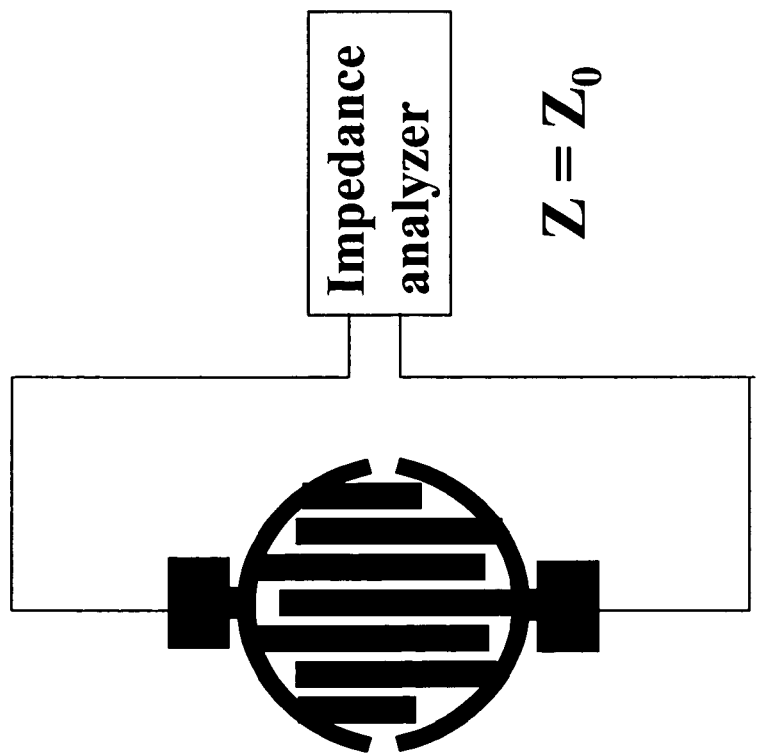
Figure 22

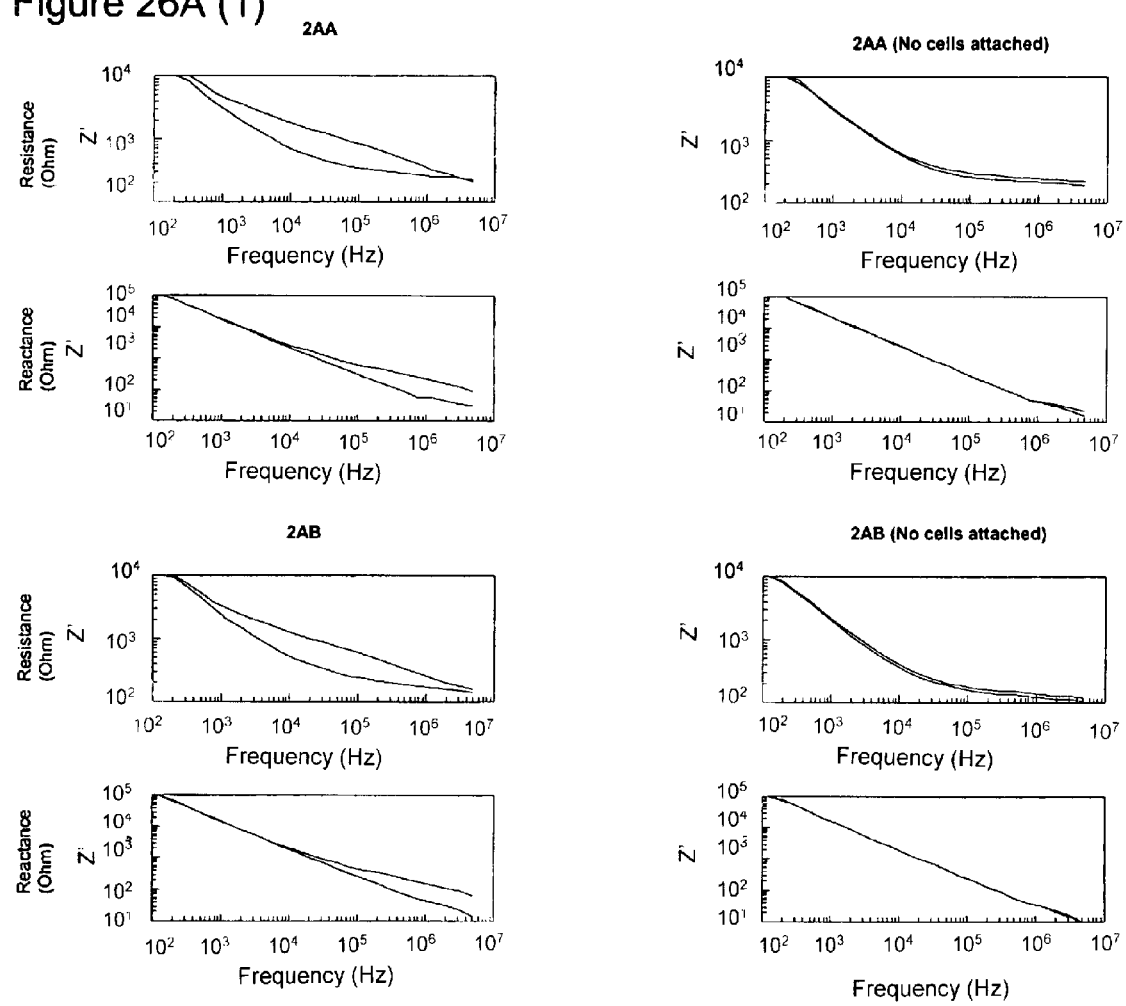

Figure 26A (2)
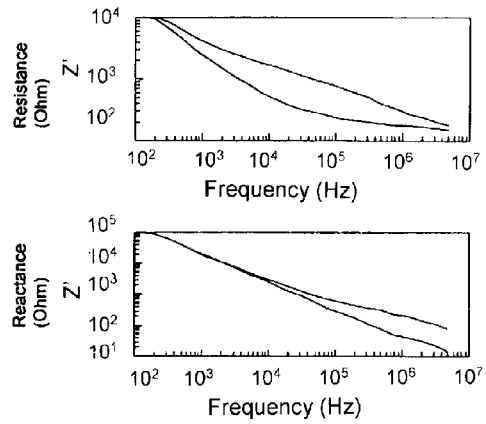
2AC
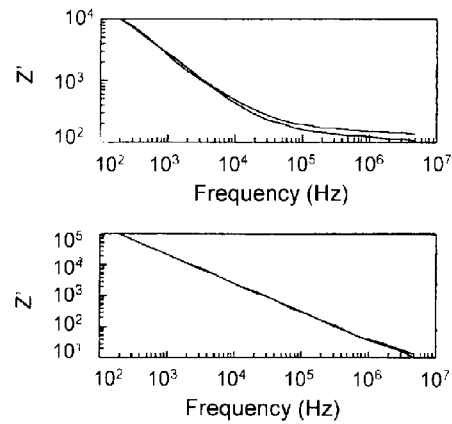
2AC No Cells attached
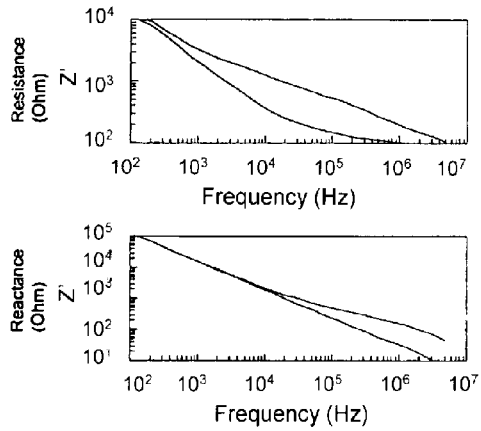
2AD
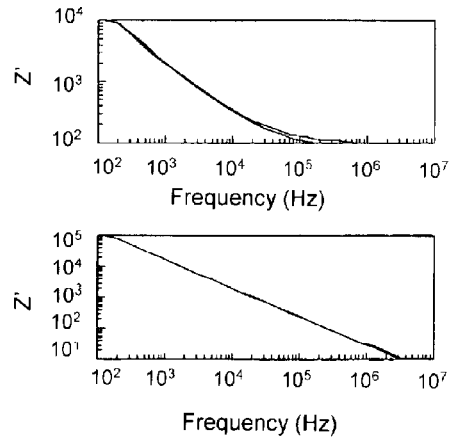
2AD (No cells attached)

Figure 26A (3)
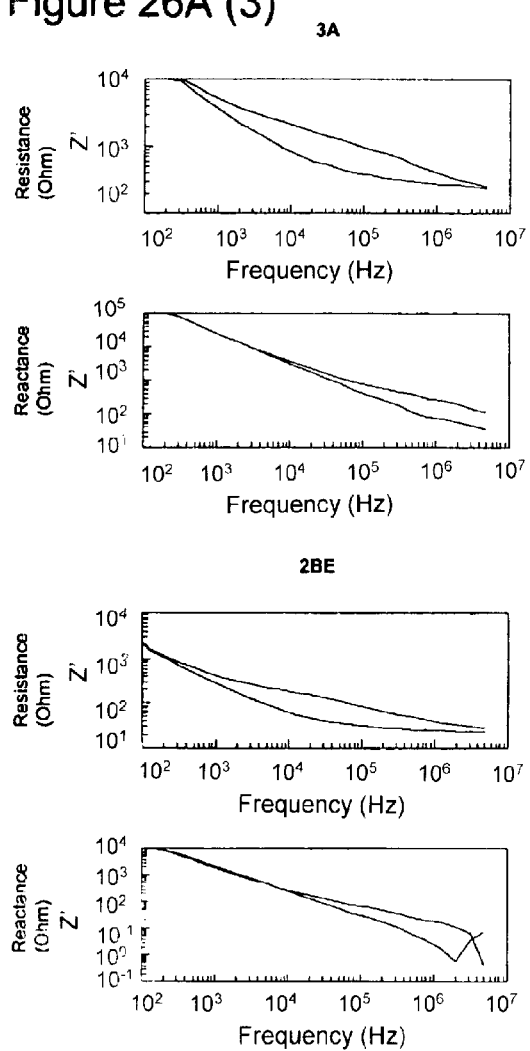
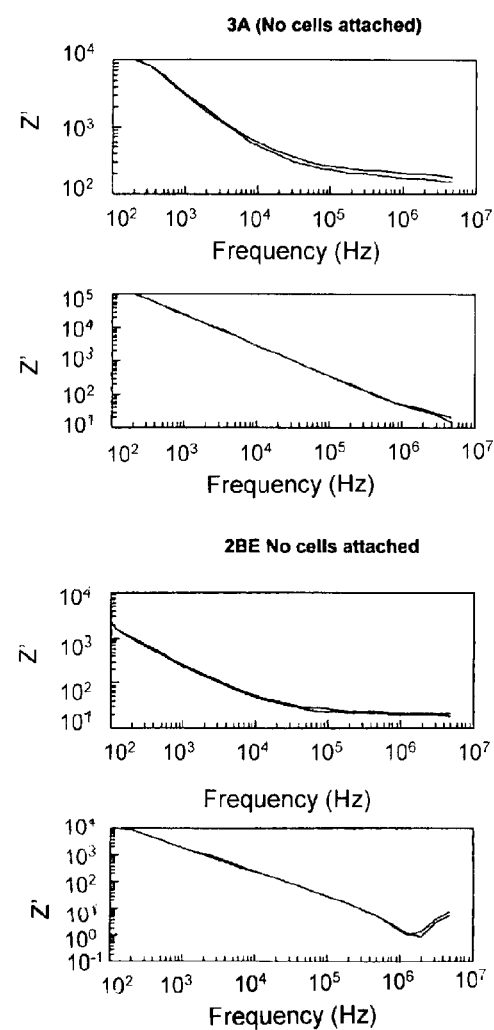

Figure 26A (4)
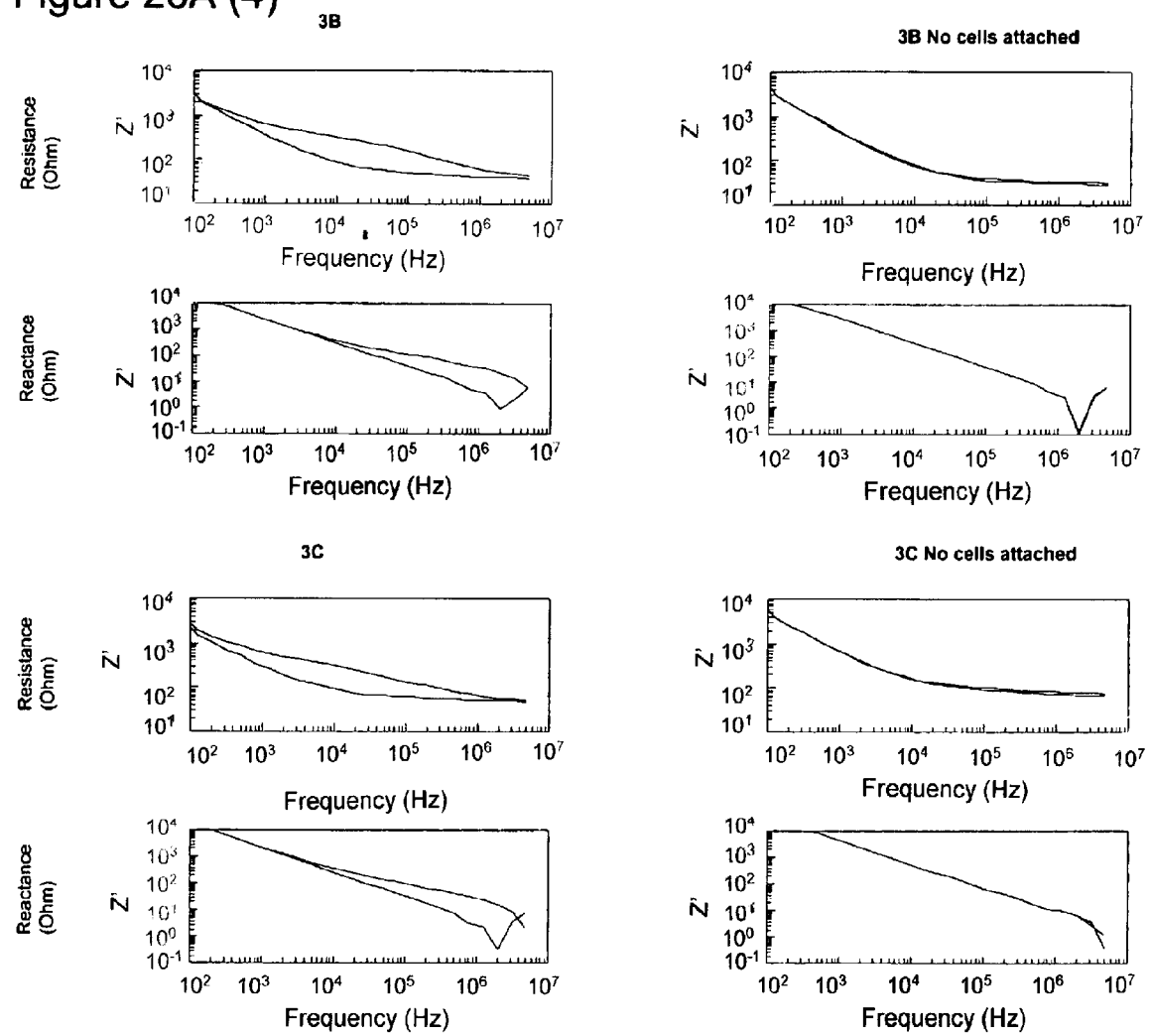

NIH 3T3 and PAE Cell Proliferation

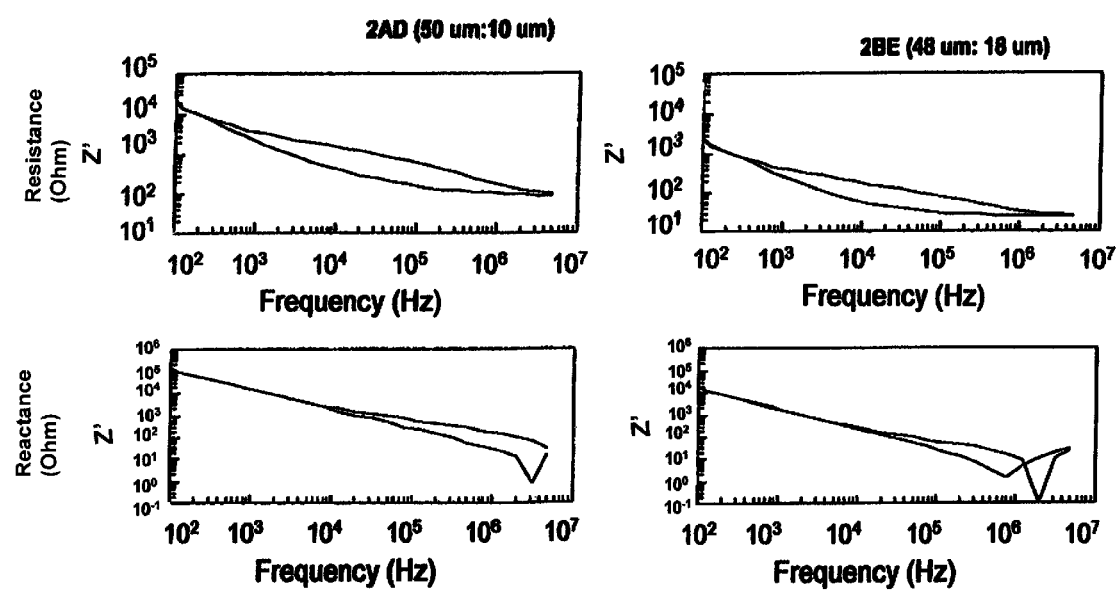
Figure 42A (1)

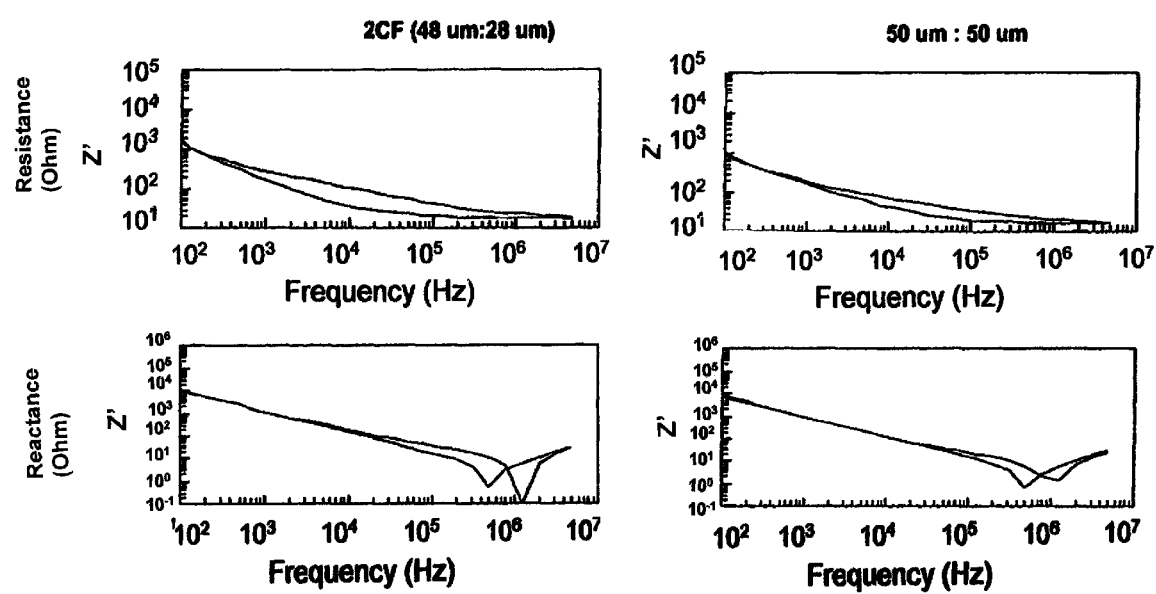
Figure 42A (2)

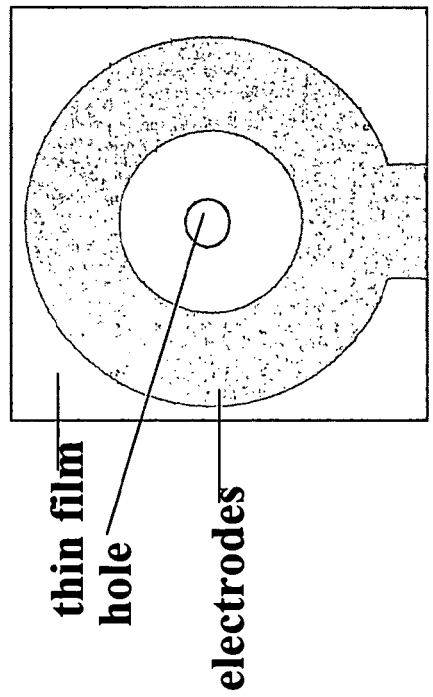
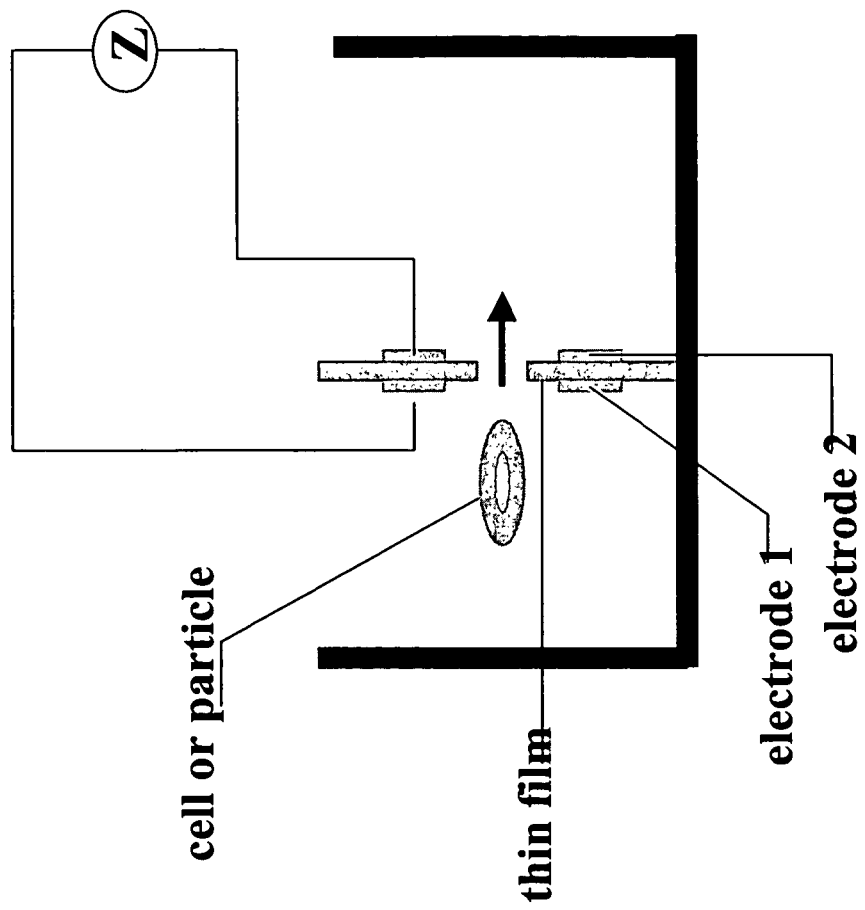
Figure 45

IMPEDANCE BASED DEVICES AND METHODS FOR USE IN ASSAYS

This application is a divisional application of U.S. patent application Ser. No. 10/705,447, filed Nov. 10, 2003, now U.S. Pat. No. 7,470,533 which claims benefit of priority to U.S. provisional application No. 60/397,749, filed on Jul. 20, 2002; U.S. provisional application No. 60/435,400, filed on Dec. 20, 2002; and U.S. Provisional application No. 60/469,572, filed on May 9, 2003, each of which is incorporated by reference herein, and U.S. patent application Ser. No. 10/705,447 also claims benefit of priority to PCT Application No. PCT/US03/22557, entitled "IMPEDANCE BASED DEVICES AND METHODS FOR USE IN ASSAYS," filed Jul. 18, 2003, which is incorporated by reference herein. This application also incorporates by reference PCT Application No. PCT/US03/22537, entitled "IMPEDANCE BASED APPARATUSES AND METHODS FOR ANALYZING CELLS AND PARTICLES ", filed Jul. 18, 2003.

BACKGROUND OF THE INVENTION

1. Technical Field

This invention relates generally to the field of sensors for use in cell and molecule based assays. In particular, the invention provides sensor devices which detect a change in measured impedance between and among electrodes, from which the presence, behavior, quantity or change in cells or molecules in a sample solution can be identified. The sensor devices can be used for monitoring cell or particle attachment, growth and migration and in identifying modulators of cell attachment, growth and migration. The sensor devices can also be used for analyzing and assaying molecules.

2. Background Art

With the advent of automated equipment for introducing compositions into wells of a microtiter plates, a number of efforts have been made to develop plates which include all of the components necessary to analyze plated cells or small molecules in a single step. For example, in Ehret, et al., *Biosensors and Bioelectronics,* 12:29-41 (1997), the authors described an electronic impedance-based device for measurement of cells in a liquid analyte sample. The presence of targeted cells in the same is indicated by a change in impedance between evenly sized and spaced electrode pairs to which the cells adhere. U.S. Pat. No. 6,376,233, describe how such a device in combination with other sensors would be produced in a microtiter plate format using semiconductor material as a the "plate" to provide the substrate for the measurement electrodes. Electrical conduits extend from electrodes in the '233 patent device in various planes, and in several directions, through the semiconductor substrate.

Others have explored in using electronic methods for analyzing and assaying biological molecules and cells. For example, U.S. Pat. No. 3,890,201 describes a multichamber module-cap combination device in which electrically conductive strips in the bottom of the chambers are used for measuring the impedance of a sample of nutrient media in which aerobic microorganisms are grown, and U.S. Pat. No. 4,072,578 describes a multi-chambered module attached to an electrically non-conductive base within which electrically conductive leads completely embedded and lying flat, terminal portions at one end of the conductive leads emerging in pairs into the chamber in spaced relationship to each other to form electrodes for culturing samples of microorganisms while monitoring the impedance of the growth media.

U.S. Pat. No. 5,187,096 discloses a cell substrate electrical impedance sensor with multiple electrode arrays. Each electrode pair within the impedance sensor for measuring the cell-substrate impedance comprises one small electrode (a measuring electrode) and one large electrode (a reference electrode) on two different layers. The difference between the electrode sizes ensures that the measured impedance change relative to the impedance when no cells are present on the electrodes is directly correlated with the cell numbers and sizes, generally 20-50 cells, or even single cells attached to or grown on the measuring electrodes. Some applications of the cell sensor include the monitoring of conditions within bioreactors, within cell cultures, the testing of compounds for cytotoxicity, research of cell biology to detect cell motility, metabolic activity, cell attachment and spreading, etc. However, this impedance sensor with two layered structures is somewhat complicated with the measuring electrodes on one layer and the reference electrodes on another layer. The selected electrode area for the small electrodes limits the maximum of 50 cells being monitored.

The use of a large (reference) electrode and a small (measurement or active) electrode for cell-electrode impedance measurement was reported in many publications, including, Giaever I. and Keese C. R., "Monitoring fibroblast behavior in tissue culture with an applied electric field". Proc. Natl. Acad. Sci. (USA), 1984, vol. 81, pp 3761-3764; Giaever I. and Keese C. R., "Micromotion of mammalian cells measured electrically", Proc. Natl. Acad. Sci. (USA), 1991, vol. 88, pp 7896-7900; Tiruppathi C. et al, "Electrical method for detection of endothelial cell shape change in real time; assessment of endothelial barrier function", Proc. Natl. Acad. Sci. (USA), 1992, vol. 89, pp 7919-7923; Lo C. M. et al., "Monitoring motion of confluent cells in tissue culture", Experimental cell research, 1993, vol. 204, pp 102-109; Lo C. M. et al, "Impedance analysis of MDCK cells measured by electric cell-substrate impedance sensing", Biophys. J., 1995, vol. 69, pp. 2800-2807; Lo C. M. et al, "pH change in pulsed $CO_2$ incubators cause periodic changes in cell morphology", Experimental cell research, 1994, vol. 213, pp. 391-397; Mitra P. et al., "Electric measurements can be used to monitor the attachment and spreading of cells in tissue culture", Bio-Techniques, 1991, vol. 11, pp. 504-510; Kowolenko M. et al, "Measurement of macrophage adherence and spreading with weak electric fields", J. Immunological Methods, (1990) vol. 127, pp. 71-77; Luong J. H. et al, "Monitoring motility, spreading, and mortality of adherent insect cells using an impedance sensor", Anal. Chem.; 2001; vol: 73, pp 1844-1848. For example, in the first article of cell-electrode impedance measurement (by Giaever I. and Keese C. R., "Monitoring fibroblast behavior in tissue culture with an applied electric field", Proc. Natl. Acad. Sci. (USA), 1984, vol. 81, pp 3761-3764), the large electrode had an area ~2 $cm^2$ and the small electrode had an area of $3\times10^{-4}$ $cm^2$.

PCT application US01/46295 (WO 02/42766) and U.S. Patent Application Publication 2002/0086280 describe a similar system adapted for monitoring cell movement. At least one sensing electrode (measurement electrode) and a counter electrode are situated in a well into which a biocompatible chemical gradient stabilizing medium is introduced and into which migratory cells are placed. A migrating cell's arrival at the sensing electrode is detected by a change in impedance due to contact between the cell and a sensing electrode, which is smaller than the counter electrode. The system can be used to determine the stimulatory or inhibitory effect of test compounds on cell migration by comparing the time of arrival of a migratory cell at a sensing electrode (detected by the impedance change) in the presence of a test compound with the time of arrival of a migratory cell at a sensing electrode in the absence of a test compound.

U.S. Pat. Nos. 5,981,268 and 6,051,422 disclose a similar hybrid sensor for measurement of single cells. In this case, an array of measuring electrodes shares a common reference electrode. In order to measure single cell responses, the diameter of measuring electrode is smaller than that of a cell. The sensors can be applied to detect and monitor changes in cells as a result of cell responses to environmental and chemical challenges. However, this impedance sensor can monitor responses of only single cells. Furthermore, the sensitivity of such devices critically depends on the cell location relative to the electrodes.

United States Patent Applications 2002/0150886 and 2002/0076690 disclose the use of antibodies immobilized on interdigitated electrodes for the detection of pathogens. The interdigitated electrodes are incorporated onto a surface of a fluidic channel through which a fluid sample is passed, and binding of a pathogen to the antibody-coated electrodes can be detected by an increase in impedance between spaced electrodes.

The use of interdigitated electrodes fabricated on silicon or sapphire or glass substrates as impedance sensors to monitor cell attachment is described in papers by Ehret et al. (Biosensors and Bioelectronics 12: 29-41 (1996), Med. Biol. Eng. Computer. 36: 365-370 (1998)), Wolf et al. (Biosensors and Bioelectronics 13: 501-509 (1998)), and Henning et al. Anti-cancer Drugs 12: 21-32 (2001)). These methods use expensive substrates such as silicon and sapphire and, due to the electrode configurations (both electrode widths and gaps are about 50 microns), have a less than optimal efficiency, as only an average of about 50% of the cells are able to contribute to the impedance signal.

U.S. Pat. No. 6,280,586 discloses a device for measuring the presence of a component of an analyte having at least one reference sensor and at least one electrical sensor each having a measurement output connectable to an evaluation device. The reference sensor interdigitated capacitor and a reference electrode each having an electrical measurement structure are located on a common substrate. The measurement structure of the electrical sensor is connected to at least one function-specific plant or animal receptor cell serving as a biological sensor, wherein each electrical sensor measures the analyte under investigation by measuring a morphologic or physiologic property of the receptor cells. A structured, biocompatible micro porous interlayer is provided between the receptor cell and the measurement structure. The receptor is at least partially adhered to the microporous interlayer. The measurement structure of the reference sensor is free of connections of function specific receptor cells. The change of the measured property is indicative of the presence of the compound in the analyte.

U.S. Pat. No. 5,810,725 discloses a planar electrode array for stimulation and recording of nerve cells and the individual electrode impedance is in a range between 1 ohm and 100 k-ohm at a frequency of 1 kHz with an electrolytic solution comprising 1.4% NaCl. U.S. Pat. No. 6,132,683 discloses an electrode array comprising a plurality of measuring electrodes and reference electrodes for monitoring and measuring electrical potential in a neural cell sample, wherein the impedance of the reference electrode is smaller than that of measuring electrodes. However, these electrodes are not optimized for a quantitative measurement of impedance at the interface between a cell and a microelectrode.

In another type of application, direct current (DC) electrical field is used to electronically size particles, in particular, biological cells by using the well-known "coulter" counting principle. In this case, a DC current is applied to a micron or multiple-micro-size aperture. Electrical voltage change is monitored when a cell or other particle is forced through the aperture. Despite its success of the coulter principle, the device is limited in its sensitivity as well as its dynamic range in counting and sizing biological cells. See U.S. Pat. Nos. 2,656,508 and 3,259842, and Larsen et al., "Somatic Cell Counting with Silicon Apertures", *Micro Tatal Analysis Systems,* 2000, 103-106, edited by A. Van den Berg et al., 2000 Kluwer Academic Publishers.

U.S. Pat. No. 6,169,394 discloses a micro-electric detector having conductivity or impedance based measurements of a test sample placed in a microchannel. The detector includes a pair of electrodes disposed on opposing sidewalls of the microchannel to create a detection zone in the microchannel between and adjacent to the electrodes. Similarly, Song at al. demonstrated use of such microelectrodes for detecting cellular DNA content by measuring capacitance change when a cell is caused to pass by two opposing electrodes disposed on the two side walls of a microfluidic channel. See Song at al., *Proc. Natl. Acad. Sci. U.S.A.,* 97(20):10687-90 (2000).

U.S. Pat. No. 5,643,742, 6,235,520 and 6,472,144 disclose systems for electrically monitoring and recording cell cultures, and for high throughput screening. The systems comprise multiple wells into each of which cells are introduced and into each of which a pair of electrodes are placed. The systems can measure the electrical conductance within each well by applying a low-voltage, AC signal across a pair of electrodes placed in the well and measuring the conductance across the electrodes, to monitor the level of growth or metabolic activity of cells contained in each well.

Others have taken different approaches to the use of impedance measurements to assay molecules in a sample. For example, Ong, et al., *Sensors,* 2:219-232 (2000), uses impedance changes in a circuit to detect the presence of bacteria in food. In German published application DE 39 15 290 and PCT Application WO 96/01836 devices are disclosed as having electrodes disposed on a substrate for use in detection of small molecules, especially polynucleotides. However, these devices are limited to use in specific applications, and are not intended for general laboratory research.

Other bioelectrical sensors rely on changes in capacitance or other signals as indicia of assay results. For example, U.S. Pat. No. 6,232,062 discloses a method for detecting the presence of a target sequence in a nucleic acid sample. The method comprises applying a first input signal comprising an AC component and a non-zero DC component to a hybridization complex, said hybridization complex comprising at least a target sequence and a first probe single stranded nucleic acid, said hybridization complex being covalently attached to a first electron transfer moiety comprising an electrode and a second electron transfer moiety, and detecting the presence of said target sequence by detecting the presence of said hybridization complex. Examples of the second electron transfer moieties include transition metal complexes, organic electron transfer moieties, metallocenes.

In another example, Patolsky et al, *Nature Biotechnology,* 19, 253-257, (2001), described a method for detection of single base mutation in DNA. With electrochemical redox labels, they measured Faradic impedance spectra for an electrode on which a primer thiolated oligonucleotide was assembled and hybridization of target DNA molecules occurred. The technique achieved a sensitivity of $10^{-14}$ mol/ml for sample DNA tested.

Bioelectrical sensors have also been adapted to use in detection of cell migration. For example, in the device of Cramer (U.S. Pat. No. 4,686,190), the passage of cells through a membrane can be detected by a sensor. However, the usefulness of the Cramer device is limited by several design limitations including in one embodiment, the concealment of the active surface of the sensor by the membrane.

This invention aims to expand the usage and application of electrical field impedance measurement and other electronic methods for measuring and analyzing cells and molecules, non-cell particles, and biological, physiological, and pathological conditions of cells, and provides devices, apparatuses and systems for these analyses.

BRIEF SUMMARY OF THE INVENTION

In one aspect, the present invention is directed to a device for assaying target small molecules, such as polynucleotides and polypeptides. The device includes a nonconductive substrate, onto which a plurality of sensors, each including an arrangement of electrodes, are disposed. The exposed surface of the electrodes includes capture molecules, to which cells may adhere and/or small molecules may bind.

Such adherence or binding causes a change in the impedance between electrodes, which change produces a signal indicative of the adherence on, or binding to, the electrodes. Further changes in impedance are measurably caused in response to changes in the population of adhered cells or bound molecules, such as cell growth or a change in the composition of the bound molecule (e.g., through hybridization).

Toward measurement of the impedance changes associated with these events, methods are provided for the use of the device. One embodiment of the device utilizes a microtiter plate-like design which is especially well adapted to use with automated assaying equipment. The device according to this embodiment of the invention takes the form of a nonconductive substrate plate, onto which one or more containers to serve as cell or small molecule sample receptacles are placed, preferably in perpendicular relationship to the substrate. Electrical conduits are provided within one or more planes of the substrate, to connect its active sensors to an impedance signal processor. The conduits are configured to minimize background noise and the potential for conduit-to-conduit interference.

In one aspect, the invention includes a device for detecting cells and/or molecules on an electrode surface through measurement of impedence changes resulting from the cells and/or molecules. The device includes a substrate having two opposing ends along a longitudinal axis and a plurality of electrode arrays positioned on the substrate. Each electrode array includes at least two electrodes, and each electrode is separated from at least one adjacent electrode in the electrode array by an expanse of non-conductive material. The electrode has a width at its widest point of more than about 1.5 and less than about 10 times the width of the expanse of nonconductive material. The device also includes electrically conductive traces extending substantially longitudinally to one of the two opposing ends of the substrate without intersecting another trace. Each trace is in electrical communication with at least one of the electrode arrays.

The "longitudinal axis" refers generally to an axis along a surface of the substrate. For example, the longitudinal axis may be parallel to the centerline of one of the two longest dimensions of the substrate (e.g., the length of the width). Similarly, "substantially longitudinally" refers to the general direction along the longitudinal axis.

The substrate may include glass, sapphire, silicon dioxide on silicon, or a polymer. The substrate may be configured as a plate. In a preferred embodiment, the device includes a plurality of receptacles. Each receptacle is disposed on the nonconductive substrate in a perpendicular orientation thereto, and each receptacle forms a fluid-tight container associated with at least one electrode array on the substrate.

Up to half of the electrical traces may extend to one end of the substrate, while up to half of the electrical traces extend to the other end of the substrate.

The device may also include electrical traces between adjacent pairs of electrode arrays.

The electrodes of each electrode array may be of equal widths. In a preferred embodiment, the electrodes each have a width of 80 microns at their widest point. In a further preferred embodiment the gap between adjacent electrodes at their widest point is 20 microns.

Each electrode array may include a plurality of evenly spaced electrode pairs. Each plurality of electrodes may be organized in an interdigitated fashion. In one embodiment, at least one bus encircles up to half of the plurality of interdigitated electrodes in each electrode array.

Alternatively, each plurality of electrodes may be organized in a concentric sinusoidal or castellated fashion. In one embodiment, at least one bus encircles up to half of the plurality of concentrically organized electrodes in each electrode array.

The bus disposed nearest to the plurality of electrodes may be separated from the plurality by an expanse of nonconductive substrate. The buses may include a pair of electrodes, each of which extends around half the diameter of the electrode array. In one embodiment, the device also includes a plurality of receptacles, wherein each receptacle is disposed on the nonconductive substrate in a perpendicular orientation thereto, wherein further each receptacle forms a fluid-tight container surrounding the buses. In one embodiment, the containers are arranged on the substrate in honeycomb fashion.

In a preferred embodiment, the device includes an impedance analyzer electrically connected to all or a plurality of the electrically conductive traces at their termini on at least one end of the substrate. The impedance may be measured at a frequency ranging from about 1 Hz to about 1 MHz.

In a preferred embodiment, the device includes one or more capture reagents immobilized on the surfaces of at least two electrodes in each electrode array. The capture reagents are capable of binding target cells and/or molecules.

In one embodiment, the device includes connection means for establishing electrical communication between the electrically conductive traces and an impedance analyzer. In a preferred embodiment, the connection means include a mechanical clip adapted to securely engage the substrate and to form electrical contact with a trace.

BRIEF DESCRIPTION OF THE DRAWINGS

FIG. 1A is a schematic representation of a device 100 with two electrode structures of same or similar areas deposited on a substrate. First electrode structure has electrode elements 110a, 110b, 110c and second electrode structure has electrode elements 120a, 120b, 120c and 120d. Electrode elements within an electrode structure are connected to each other by arc-shaped connection electrode bus 125. Like the electrode elements, such connection-buses (125) are also made of electrically-conductive material (e.g. gold film, platinum film, gold film over a chromium or titanium film). These electrically-conductive connection-paths or connection buses (125) may have an insulating coating. Electrode elements 110a-110c and 120a-120d comprise electrode lines with connected circles added on the line. The overall area of electrode elements and gaps between electrode elements may correspond to, or may be slightly larger than, or may be slightly smaller than, the bottom of a well (e.g., a cylinder shaped well, a conical shaped well, or a cubic shaped well), for example, a 24 well-plate, a 96-well plate, or 384 well plate that are commonly used. The whole surfaces of the wells may be covered with electrodes to ensure that the molecular interactions occurring on the bottom surface of the well can contribute to the impedance change. This arrangement has an advantage that non-uniform molecular interaction occurring on the bottom surface of these wells would result in only a small variation in the impedance measured between electrode structure 110 and 120, 150 are connection pads that can be connected to an external impedance measurement circuit. 130 is the electrical connection traces that connects the connection pad to the electrode structures 110 and 120. Such connection traces can extend in any direction in the plane of the electrodes. FIG. 1 C is a schematic representation of a device 300 with two electrode structures of similar areas deposited on a substrate. Electrode structures 310 and 320 comprise multiple interconnected electrode elements (310a-310f, 320a-320f). Electrode elements (310a-310c, 320a-320d) are rectangular lines and together form an interdigitated electrode structure unit. Different from FIG. 1A and FIG. 1B, the electrode structures having electrode elements 310a-310c and 320a-320c are connected to connection pads 350.

FIG. 8 shows a schematic representation of signal amplification in molecular detection by measuring the catalytic products of an enzyme-mediated reaction involving targeted small molecules. As depicted, measured changes in impedance indicate the presence of a catalytic product from the enzyme-mediated reactions on the sensor surface. In one exemplary approach, the enzyme-mediated reactions occur on the surfaces of electrodes, catalytic products are precipitants from the solution onto electrode surfaces. The electronic impedances are measured to monitor the presence and quantity of the catalytic products on the electrodes.

FIGS. 19(A, C, E and G) are cross-sectional drawing of a device of the present invention showing two electrodes. Capturing molecules, depicted with "Y" symbols, are anchored, placed, introduced, or bound to surface of the electrodes. Capturing molecules may be any molecules that may interact with target molecules to be measured or monitored in a sample solution. Capturing molecules may be antibodies, peptides, ligands, receptors proteins, nucleic acids, nucleotides, oligonucleotides, or any molecules that can interact with or bind to target molecules. Illustrated in FIGS. 19(A, C, E and G) is a measurement of background impedance $Z_0$ as measured for the electrodes coated with or covered with or modified with capturing molecules.

FIG. 19(B) is Cross-sectional drawing of a device of the present invention showing two electrodes with capturing molecules, depicted with "Y" symbols, on the surfaces of the electrodes and with target molecules, depicted with "◆" symbols and binding to the capture molecules. Capturing molecules and target molecules form a molecular interaction or molecular binding pairs so that target molecules can bind to the capturing molecules. Target molecules may be any molecules that may interact with capturing molecules. Target molecules in a sample solution or suspected to be in a sample solution are molecules of interest to be measured or monitored. Like capturing molecules, target molecules may be antibodies, antigens, peptides, ligands, receptors, proteins, nucleic acids, nucleotides, oligonucleotides, or any molecules that can interact with or bind to capturing molecules. Illustrated in (B) is a measurement of impedance $Z_M$ as measured for the electrodes modified with capturing molecules to which target molecules bind. The figures in (A) and (B) are a pair and show that the impedance between electrodes will be changed from $Z_0$ to $Z_M$, corresponding to a condition that electrodes are modified with capturing molecules (A) and to a condition that target molecules bind to the capturing molecules (B).

FIG. 19(D) is a cross-sectional drawing of a device of the present invention showing two electrodes with capturing molecules, depicted with "Y" symbols, on the surfaces of the electrodes and with target molecules, depicted with "◆" symbols and binding to the capture molecules. Different from FIG. 19(B), target molecules here are labeled with labeling molecules or labeling particles, depicted with "●" symbols. Capturing molecules and target molecules form a molecular interaction or molecular binding pairs so that target molecules can bind to the capturing molecules. Labeling molecules or particles are the molecules or particles that would increase the impedance change of ($Z_{ML}-Z_0$), in another word, to amplify the detection signal. Target molecules may be any molecules that may interact with capturing molecules. Target molecules in a sample solution or suspected to be in a sample solution are molecules of interest to be measured or monitored. Like capturing molecules, target molecules may be antibodies, antigens, peptides, ligands, receptors, proteins, nucleic acids, nucleotides, oligonucleotides, or any molecules that can interact with or bind to capturing molecules. Illustrated in (D) is a measurement of impedance $Z_{ML}$ as measured for the electrodes modified with capturing molecules to which target molecules bind, wherein target molecules are labeled with labeling molecules or particles. The figures in (C) and (D) are a pair and show that the impedance between electrodes will be changed from $Z_0$ to $Z_{ML}$, corresponding to a condition that electrodes are modified with capturing molecules (C) and to a condition that target molecules bind to the capturing molecules (D). Labeling molecules or particles in FIG. 19(D) are used to amplify or further increase the impedance change of ($Z_{ML}$–$Z_0$). One non-limiting example of the labeling molecules may be certain large organic molecules whose presence on the electrode will affect the passage of the ions or electrons at the electrode surfaces and will result in a large change in impedance as measured between electrodes. One example of labeling particles may be nano-sized or microsized, electrically non-conducing, or semi-conducting, or even conducing particles. Another example of labeling particles may nano-sized or micro-sized liposomes into whose surfaces signal amplifying molecules are incorporated. The presence of such labeling particles will affect the passage of the ions or electrons at the electrode surfaces and will result in a large change in impedance as measured between electrodes.

FIG. 19(F) is a cross-sectional drawing of a device of the present invention showing two electrodes with capturing molecules, depicted with "Y" symbols, on the surfaces of the electrodes and with target molecules, depicted with "♦" symbols and binding to the capture molecules. Different from FIG. 19(B), target molecules here are labeled with labeling molecules or labeling particles, depicted with "●" symbols. Capturing molecules and target molecules form a molecular interaction or molecular binding pairs so that target molecules can bind to the capturing molecules. Labeling molecules or particles are the molecules or particles that would increase the impedance change of ($Z_{MP}$–$Z_0$), in another word, to amplify detection signal. In this case, the signal amplification of the labeling molecules or particles is achieved through certain reaction between labeling molecules or particles with some reaction (R) molecules in solution. The reaction product (P) is deposited or precipitated on the electrode surfaces, resulting the impedance $Z_{MP}$ between electrodes. Target molecules may be any molecules that may interact with capturing molecules. Target molecules in a sample solution or suspected to be in a sample solution are molecules of interest to be measured or monitored. Like capturing molecules, target molecules may be antibodies, antigens, peptides, ligands, receptors, proteins, nucleic acids, nucleotides, oligonucleotides, or any molecules that can interact with or bind to capturing molecules. Illustrated in (F) is a measurement of impedance $Z_{MP}$ as measured for the electrodes modified with capturing molecules to which target molecules bind, wherein target molecules are labeled with labeling molecules or particles. The figures in (E) and (F) are a pair and show that the impedance between electrodes will be changed from $Z_0$ to $Z_{MP}$, corresponding to a condition that electrodes are modified with capturing molecules (E) and to a condition that target molecules bind to the capturing molecules (F). Labeling molecules or particles in FIG. 19(F) are used to amplify or further increase the impedance change of ($Z_{ML}$–$Z_0$). The signal amplification of the labeling molecules or particles in FIG. 19(F) is achieved through certain reaction between labeling molecules or particles with some reaction (R) molecules in solution. The reaction product (P) is deposited or precipitated on the electrode surfaces and will affect the passage of electrons and/or ions at the electrode surfaces, leading to a large impedance change. The condition show in FIG. 19(F) can be regarded as a particular example of FIG. 19(D).

FIG. 19(H) is a cross-sectional drawing of a device of the present invention showing two electrodes with capturing molecules, depicted with "Y" symbols, on the surfaces of the electrodes and with target molecules, depicted with "♦" symbols and binding to the capture molecules. Different from FIG. 19(B), target molecules here are labeled with labeling molecules, depicted with "●" symbols. Capturing molecules and target molecules form a molecular interaction or molecular binding pairs so that target molecules can bind to the capturing molecules. Labeling molecules are the molecules that would increase the impedance change of ($Z_{MEP}$–$Z_0$), in another word, to amplify detection signal. In this case, the labeling molecules are enzymes and signal amplification of the labeling molecules is achieved through enzyme-mediated or catalyzed reactions of substrate molecules (S) in a solution. The product (P) of the enzyme-mediated reaction is deposited or precipitated on the electrode surfaces, resulting impedance ($Z_{MEP}$) of the electrodes is measured. Target molecules may be any molecules that may interact with capturing molecules. Target molecules in a sample solution or suspected to be in a sample solution are molecules of interest to be measured or monitored. Like capturing molecules, target molecules may be antibodies, antigens, peptides, ligands, receptors, proteins, nucleic acids, nucleotides, oligonucleotides, or any molecules that can interact with or bind to capturing molecules. Illustrated in (H) is a measurement of impedance $Z_{MEP}$ as measured for the electrodes modified with capturing molecules to which target molecules bind, wherein target molecules are labeled with labeling molecules or particles. The figures in (G) and (H) are a pair and show that the impedance between electrodes will be changed from $Z_0$ to $Z_{MEP}$, corresponding to a condition that electrodes are modified with capturing molecules (G) and to a condition that target molecules bind to the capturing molecules (H). Labeling molecules in FIG. 19(G) are used to amplify or further increase the impedance change of ($Z_{MEP}$–$Z_0$). In this case, the labeling molecules are enzymes and signal amplification of the labeling molecules is achieved through enzyme-mediated or catalyzed reactions of substrate molecules (S) in a solution. The product (P) of the enzyme-mediated reaction is deposited or precipitated on the electrode surfaces, resulting impedance ($Z_{MEP}$) of the electrodes is measured. The reaction product (P) is deposited or precipitated on the electrode surfaces and will affect the passage of electrons and/or ions at the electrode surfaces, leading to a large impedance change. The condition show in FIG. 19(H) can be regarded as a particular example of FIG. 19(F). Some examples of such enzyme-based signal amplification are described in FIG. 8.

FIG. 22 is a schematic representation of a system for monitoring the impedance change as the cells are adhered to the electrode surfaces.

FIG. 41(A) is a summary of the frequency spectra shown in FIGS. 38(C), 39(C) and 40(C). One method to calculate "cell number index" is based on such frequency spectra of resistance ratios by first determining the maximum value of the resistance ratio and then subtracting "one" from the maximum value. The "cell number indices" calculated this way for adding cells of different numbers of 7000, 3200 and 500 are 5.17, 1.82 and 0.17, respectively. Evidently, the larger the number of cells, the larger the cell number index.

FIG. 41(A) is a summary of the frequency spectra shown in FIGS. 38(D), 39(D) and 40(D).

FIG. 45 is a schematic diagram for impedance analysis of single particles going through a micro-pore on a substrate, where the electrodes are integrated on the substrate.

DETAILED DESCRIPTION OF THE INVENTION

Figure 1B:
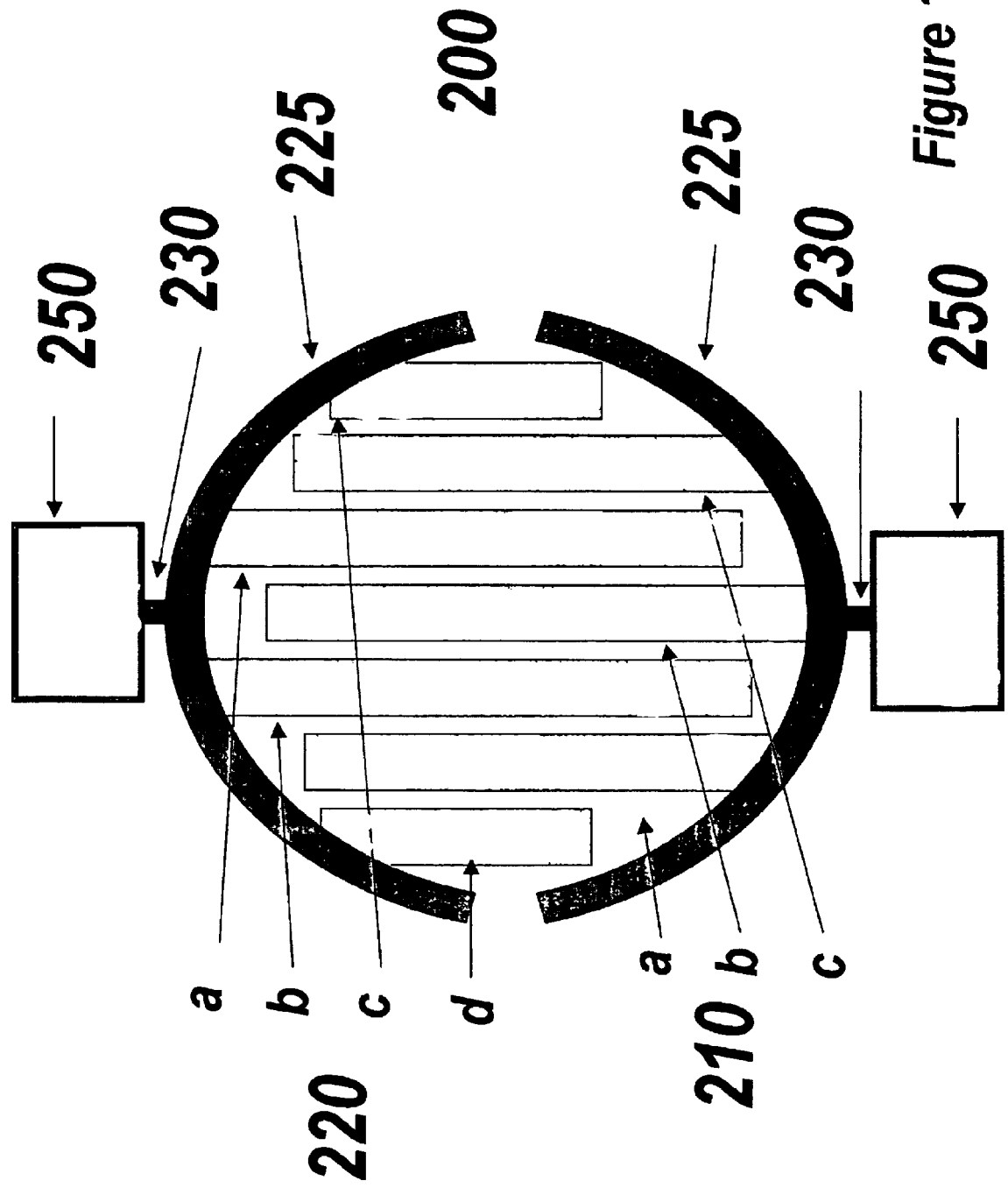
FIG. 1B is a schematic representation of an device 200 with two electrode structures of similar areas deposited on a substrate. Electrode structures 210 and 220 comprise multiple interconnected electrode elements. Electrode elements (210a-210c, 220a-220d) are rectangular lines and together form an interdigitated electrode structure unit. Similar to FIG. 1A, the electrode elements (210a-210c, 220a-220d) within each electrode structure are connected through arc-shaped, electrically conductive paths or electrode buses (225). Connection pads 250 are connected to electrode structures through the electrical connection traces 230.
Figure 2:
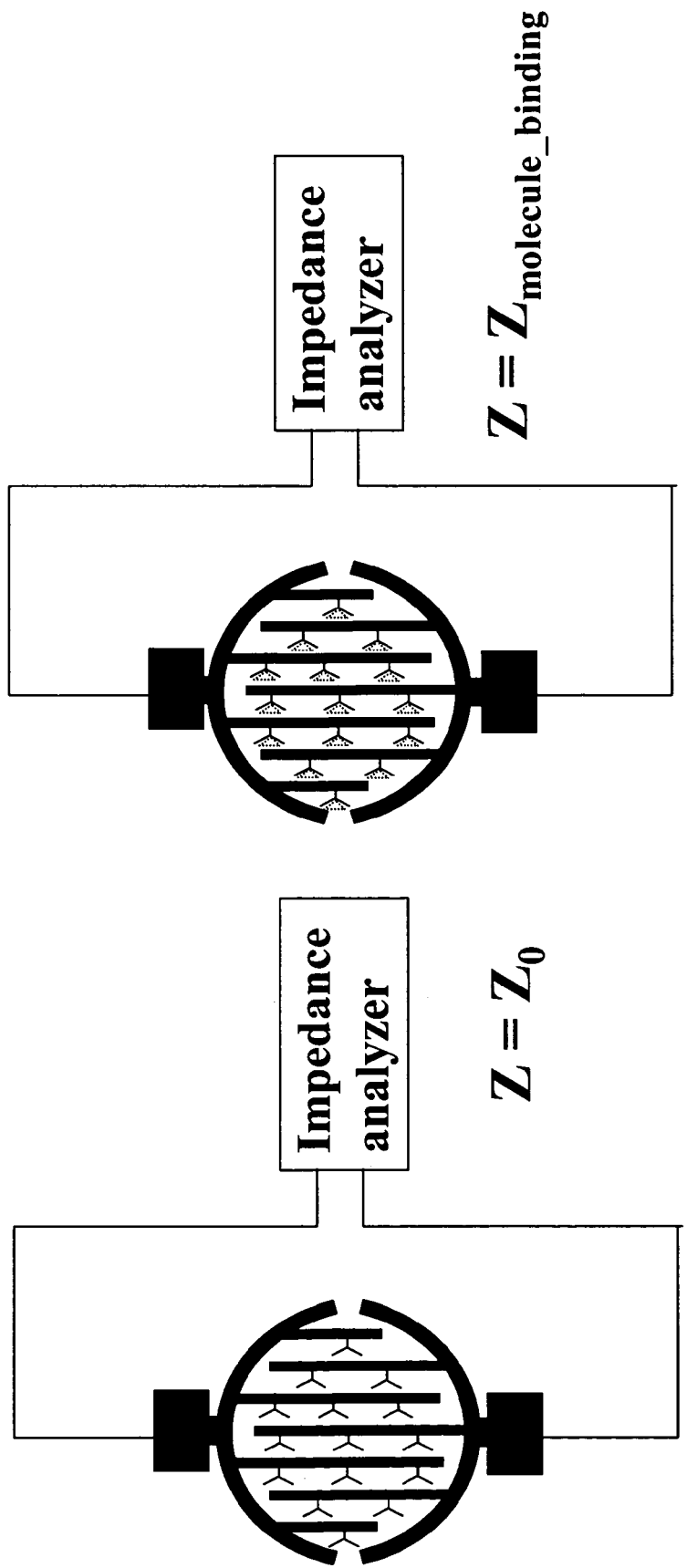
FIG. 2 is a schematic representation of a system for monitoring the impedance change as a result of the target molecules being captured to or bound to the electrode surfaces. The "γ" symbols in the Figure represent the capture molecules on the electrode surfaces. The "Δ" symbols represent the target molecules that can bind to the capture molecules. The left panel shows the background impedance ($Z_0$) of the electrodes prior to the binding of target molecules. The right panel shows the measured impedance ($Z_{molecule-ng}$) of the electrodes after the binding of target molecules to the capture molecules. The impedance is monitored by an impedance analyzer or impedance measuring circuits. Impedance analyzers are well known to those skilled in the art.
Figure 3:
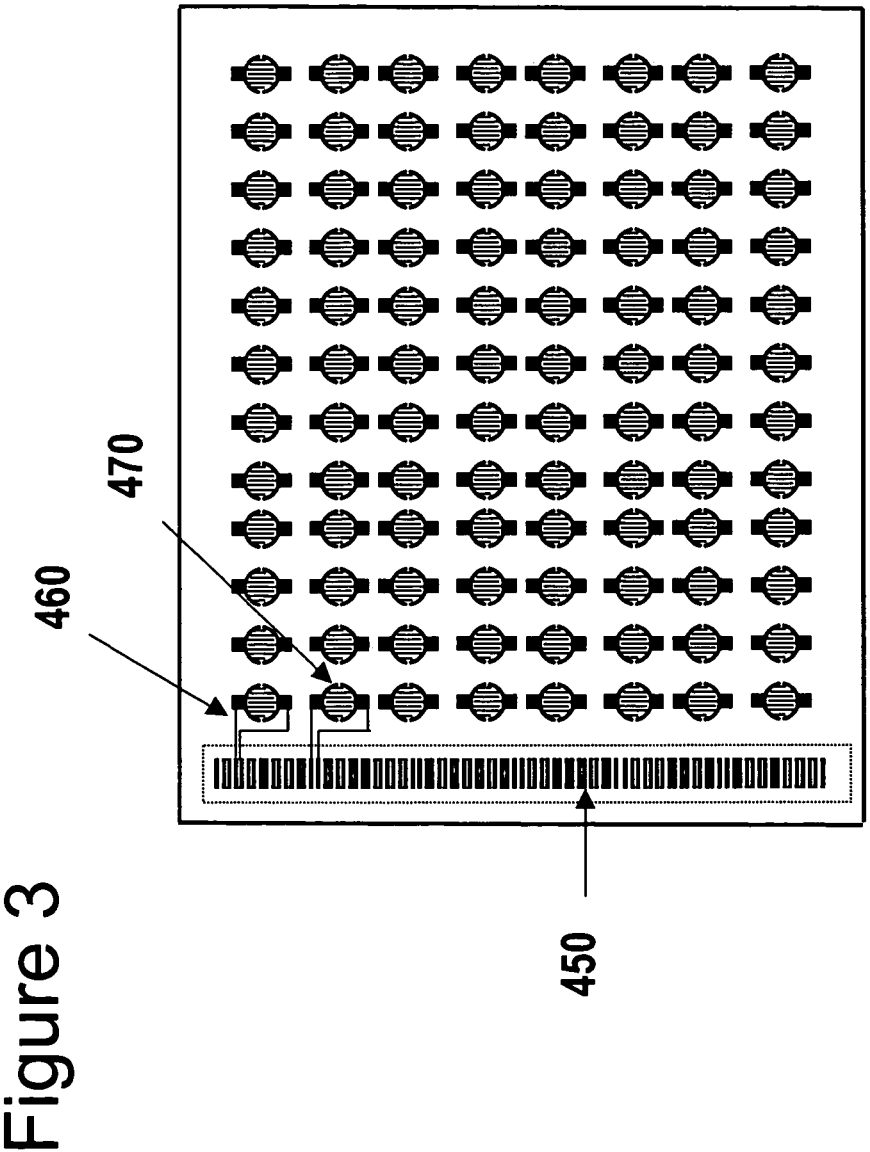
FIG. 3 is a schematic representation of a molecular assay, 96-well, electrode plate with detection microelectrode arrays fabricated or incorporated into a substrate that corresponds to bottom surface of the wells. For simplicity, the structures defining the walls of the wells are not shown. The electrode lines 450 on the left of the FIG. 3 are connection pads for the microelectrode array to connect to external impedance measurement circuits. There are two electrode structures forming an electrode structure unit for each well (or for at least some of the wells) and thus two connection pads are used for a well that comprises an electrode structure unit used in the device. For illustrative purposes, the electrical connections are shown for only electrode structures from two up-left wells 460 and 470. One approach to form such a 96-well, electrode plate is to attach the substrate comprising electrode structures to a plate comprising an arrangement of tubes, such as a bottomless microwell plate (e.g. a microtiter plate), so that the substrate forms the bottoms of wells or fluid containers that can be used to monitor molecular interactions.

For clarity of disclosure, and not by way of limitation, the detailed description of the invention is divided into the subsections that follow.

A. Definitions

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "membrane" is a sheet of material.

As used herein, "biocompatible membrane" means a membrane that does not have deleterious effects on cells, including the viability, attachment, spreading, motility, growth, or cell division.

When a suspension of viable, unimpaired, epithelial or endothelial cells is added to a vessel, a surface of the vessel "is suitable for cell attachment" when a significant percentage of the cells are adhering to the surface of the vessel within twelve hours. Preferably, at least 50% of the cells are adhering to the surface of the vessel within twelve hours. More preferably, a surface that is suitable for cell attachment has surface properties so that at least 70% of the cells are adhering to the surface within twelve hours of plating (i.e., adding cells to the vessel). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating. To have desired surface properties for cell attachment, the surface may need to chemically-treated (e.g. treatment with an acid and/or with a base), and/or physically treated (e.g. treatment with plasma), and/or biochemically treated (e.g. coated with one or more molecules or biomolecules that promotes cell attachment). In the present invention, a biocompatible surface (such as a membrane) preferably is suitable for the attachment of cells of the type that are to be used in an assay that uses the biocompatible surface (e.g., membrane), and most preferably, allows the attachment of at least 90% of the cells that contact the biocompatible surface during the assay.

A "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

An "extracellular matrix component" is a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

An "electrode" is a structure having a high electrical conductivity, that is, an electrical conductivity much higher than the electrical conductivity of the surrounding materials.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

"Electrode traces" are electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

A "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

"Interdigitated" means having projections coming one direction that interlace with projections coming from a different direction in the manner of the fingers of folded hands (with the caveat that interdigitated electrode elements preferably do not contact one another).

As used herein, a "high probability of contacting an electrode element" means that, if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "at least two electrodes fabricated on said substrate" means that the at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same side of said substrate" means that the at least two electrodes are fabricated on the same side of the substrate.

As used herein, "at least two electrodes fabricated to a same plane of said substrate" means that, if the nonconducting substrate has multiple layers, the at least two electrodes are fabricated to the same layer of the substrate.

As used herein, "said . . . electrodes have substantially same surface area" means that the surface areas of the electrodes referred to are not substantially different from each other, so that the impedance change due to cell attachment or growth on any one of the electrodes referred to will contribute to the overall detectable change in impedance to a same or similar degree as the impedance change due to cell attachment or growth on any other of the electrodes referred to. In other words, where electrodes have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode structure is less than 5, 4, 3, 2, 1.5, 1.2 or 1.1. More preferably, the at least two electrodes of an electrode structure have nearly identical or identical surface area.

As used herein, "said device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g. nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among said electrodes" means that the impedance between or among said electrodes would have a significant change that can be detected by an impedance analyzer or impedance measurement circuit when molecule binding reaction occurs on the electrode surfaces. The impedance change refers to the difference in impedance values when molecule binding reaction occurs on the electrode surface of the apparatus and when no molecular reaction occurs on the electrode surface. Alternatively, the impedance change refers to the difference in impedance values when cells are attached to the electrode surface and when cells are not attached to the electrode surface, or when the number, type, activity, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among said electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "said at least two electrodes have substantially different surface area" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode is significantly smaller than the impedance change due to cell attachment or growth on the smaller electrode. Ordinarily, the ratio of surface area between the largest electrode and the smallest electrode is more than 10. Preferably, the ratio of surface area between the largest electrode and the smallest electrode is more than 20, 30, 40, 50 or 100.

As used herein, "multiple pairs of electrodes or electrode structures spatially arranged according to wells of a multi-well microplate" means that the multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound.

As used herein, "the electrodes have, along the length of the microchannel, a length that is substantially less than the largest single-dimension of a particle to be analyzed" means that the electrodes have, along the length of the microchannel, a length that is at least less than 90% of the largest single-dimension of a particle to be analyzed. Preferably, the electrodes have, along the length of the microchannel, a length that is at least less than 80%, 70%, 60%, 50%, 40%, 30%, 20%, 10%, 5% of the largest single-dimension of a particle to be analyzed.

As used herein, "the microelectrodes span the entire height of the microchannel" means that the microelectrodes span at least 70% of the entire height of the microchannel. Preferably, microelectrodes span at least 80%, 90%, 95% of the entire height of the microchannel. More preferably, microelectrodes span at least 100% of the entire height of the microchannel.

As used herein, "an aperture having a pore size that equals to or is slightly larger than size of said particle" means that aperture has a pore size that at least equals to the particle size but less than 300% of the particle size. Here both pore size and particle size are measured in terms of single dimension value.

As used herein, "microelectrode strip or electrode strip" means that a non-conducting substrate strip on which electrodes or electrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. The microelectrode strip can be of any geometry for the present invention. One exemplary geometry for the microelectrode strips is rectangular shape—having the width of the strip between less than 50 micron to over 10 mm, and having the length of the strip between less than 60 micron to over 15 mm. An exemplary geometry of the microelectrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

B. Devices and Methods for Analyzing or Assaying Molecules and Cells

The devices for assaying target molecules of the invention permit analysis of multiple samples of molecules in a simple, automatable fashion. Generally, the devices include: a) a nonconducting substrate; b) at least two electrodes fabricated on said substrate, wherein the surfaces of said electrodes are modified with capture molecules to which target molecules in a solution can bind, c) at least two connection pads on said substrate, wherein said at least two electrodes are electrically connected by traces respectively to said at least two connection pads. In use, binding of target molecules from a biological sample (preferably in solution) to capture molecules on electrode surfaces results in a detectable change in impedance between or among said at least two electrodes.

In another aspect, the present invention is directed to a device for assaying molecules in a sample solution, which device comprises: a) a nonconducting substrate; b) at least two electrode structures fabricated on said substrate, wherein i) one of said at least two electrode structures has at least two electrode elements; and ii) the surfaces of said at least two electrode structures are modified with capture molecules to which target molecules in a solution or suspected in a solution can bind; c) at least two connection pads on said substrate, wherein said at least two electrode structures are connected respectively to said at least two connection pads, wherein said binding of target molecules in a solution or suspected in a solution to capture molecules results in a detectable change in impedance between or among said at least two electrode structures.

In another aspect, the present invention is directed to a device for monitoring cell-substrate impedance, which device comprises: a) a nonconducting substrate; b) at least two electrodes fabricated on a same side of the substrate, wherein the at least two electrodes have substantially the same surface area; and c) at least one connection pad on said substrate, wherein said at least two electrodes are connected to said at least one connection pad; in which the device has a surface suitable for cell attachment or growth and cell attachment or growth on the device results in detectable change in impedance between or among the at least two electrodes.

In another aspect, the present invention is directed to apparatus for monitoring cell-substrate impedance, which apparatus comprises: a) a nonconducting substrate; b) at least two electrodes fabricated on the same side of the substrate, in which the at least two electrodes have substantially same surface area; c) at least one connection pad on said substrate, wherein said at least two electrodes are connected to said at least one connection pad; and d) an impedance analyzer connected to the one or more connection pads, wherein the device has a surface suitable for cell attachment or growth and cell attachment or growth on the device results in a detectable change in impedance between or among the at least two electrodes.

In still another aspect, the present invention is directed to a device for monitoring cell-substrate impedance, which device comprises: a) a nonconducting substrate; b) at least two electrode structures fabricated to the same side of said substrate, wherein said at least two electrode structures have substantially same surface area and each of said at least two electrode structures comprises two or more electrode elements; c) at least one connection pad on said substrate, wherein said at least two electrode structures are connected to said at least one connection pad; wherein the device has a surface suitable for cell attachment or growth and cell attachment or growth on the device results in a detectable change in impedance between or among the at least two electrode structures.

Preferably, cell attachment or growth on the surface of any of the electrodes or electrode structures in the above devices results in detectable change in impedance between or among said electrodes or electrode structures.

In yet another aspect, the present invention is directed to a device for monitoring cell-substrate impedance, which device comprises: a) a nonconducting substrate; b) at least two electrodes fabricated on the same side of the substrate, the at least two electrodes having substantially different surface areas; and c) means for connecting said at least two electrodes to connection pads located on the substrate, wherein the device has a surface suitable for cell attachment or growth and said cell attachment or growth on the device results in a detectable change in impedance between or among the at least two electrodes. Preferably, an electrode having a smaller surface area than the largest electrode of said at least two electrodes has a surface modified by a cell adhesion-promoting moiety.

The change in impedance to be detected in the above devices for assaying target molecules or monitoring cell-substrate impedance can be measured in any suitable range of frequency. For example, the impedance can be measured in a frequency ranging from about 1 Hz to about 100 MHz. The impedance can be measured in a frequency ranging from about 100 Hz to about 2 MHz. The impedance is typically a function of the frequency, i.e., the impedance values change as frequency changes.

The impedance between or among electrodes has two components—a resistance component and a reactance component. The reactance can be divided into two categories, capacitive reactance and inductive reactance. In cases where an impedance has a resistance component and a capacitive reactance component, the impedance is sometimes said to have a resistance component and a capacitance component. A change in either resistance component or reactance component or both components can constitute a change in impedance.

Any suitable nonconductive substrate can be used in the present devices. As used herein "non-conducting" means nonconductive at the conditions under which the device is to be used, in particular, materials having resistivities greater than about $10^5$ ohm meters, and preferably greater than about $10^6$ ohm meter, more preferably greater than about $10^7$ ohm meters. Exemplary substrates can comprise many materials, including, but not limited to, silicon dioxide on silicon, silicon-on-insulator (SOI) wafer, glass (e.g., quartz glass, lead glass or borosilicate glass), sapphire, ceramics, polymer, plastics, e.g., polyimide (e.g. Kapton, polyimide film supplied by DuPont), polystyrene, polycarbonate, polyvinyl chloride, polyester, polypropylene and urea resin. Preferably, the substrate and the surface of the substrate are not going to interfere with molecular binding reactions that will occur at the substrate surface. For cell-substrate impedance monitoring, any surface of the nonconducting substrate that can be exposed to cells during the use of a device of the present invention is preferably biocompatible. Substrate materials that are not biocompatible can be made biocompatible by coating with another material, such as polymer or biomolecular coating. The substrate material may be porous or nonporous. The substrate can also be made of a printed-circuit-board (PCB). In this case, the PCB board refers to a mechanical assembly including layers of fiberglass sheet, optionally laminated with etched metal film patterns (e.g. copper patterns). For electronics industry, a printed-circuit-board is used to mount electronic parts suitable for packaging. In the present application, the PCB board can be used to pattern desired electrode configurations for detecting and measuring molecules in the solution, and for measuring cell-substrate impedance. The surfaces of PCB substrates that are exposed to sample solutions in using a device of the present invention can be coated, for example with polymers or biomolecular coatings, if necessary. For monitoring cell-substrate impedance, the surfaces of PCB substrates that are exposed to cells in using a device or apparatus of the present invention can be coated, for example with polymers or biomolecular coatings, to render the surfaces biocompatible.

A substrate can have a coating to which the target molecules in a solution or suspected in a solution can bind to. The coating may contain specific capture molecules to which to the target molecules can specifically bind to. The capture molecules can be any molecules including nucleic acid molecules, protein molecules, antibodies (against proteins, antigens, nucleic acid molecules such as DNA or RNA or DNA/RNA hybrids, chemical molecules, etc), or any combination of the above.

A substrate can have a coating that can promote cell attachment. The coating can be a polymer, such as a plastic film, or one or more biomolecules or one or more derivatives of one or more biomolecules, such as, but not limited to a polymer such as polyornithine or polylysine, peptides or proteins, or extracellular matrix components (or derivatives thereof), including, but not limited to, gelatin, fibronectin, laminin, collagen, one or more glycosaminoglycans, one or more peptidoglycans, etc. Such coatings can preferably but optionally cover the entire surface of a substrate that is exposed to or can be contacted by cells during the use of a device, including the electrode surfaces. A coating can be a semi-solid or gel. A coating can be a simple or complex mixture of biomolecules and can simulate or replicate a naturally occurring extracellular matrix.

The extracellular matrix that surrounds many animal cells forms the structural framework that stabilizes tissues and plays an important role in cell differentiation, proliferation, migration, shape, orientation and signaling pathways. Although many cell types can be cultured on tissue culture plastic, this environment is not physiological. Extracellular matrix molecules when coated on substrates can provide an effective physiological substrate that support and promotes key cell functions. A given extracellular matrix (natural, derived from cells or tissues, or artificial) can be a complex mixture containing glycoproteins, collagens and proteoglycans. Nonlimiting examples of extracellular matrix components include collagens (e.g., fibrillar, type I, V and II), glycoproteins such as fibronectin, laminin, vitronectin, thrombospondin, tensascin. An extracellular matrix can optionally comprise additional components such as, but not limited to, growth factors For example, Matrigel™ Basement Membrane Matrix (BD BioSciences) is a solubilized basement membrane preparation extracted from the Engelbreth-Holm-Swarm (REHS) mouse sarcoma, a tumor rich in extracellular matrix proteins. Its major component is laminin, followed by collagen IV, heparan sulfate proteoglycans, entactin and nidogen. It also contains TGF-beta, fibroblast growth factor, tissue plasminogen activator, and other growth factors which occur naturally in the EHS tumor.

In use, a device of the present invention can include one or more receptacles which serve as fluid containers. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastics, glass, or plastic coated materials such as ceramics, glass, metal, etc.

A substrate of a device of the present invention can have one or more holes, or pores. In some preferred embodiments of the present invention, in which a change in impedance is detected by cell attachment, for example, to the upper surface of a substrate, and the upper surface of the substrate comprises one or more electrodes, the holes in the substrate can be less than the diameter of the cells to be used in an assay using the device, such that the cells do not go through the holes of the substrate. For example, the pores can be less than about 5 microns, or less than about 1 micron in diameter. Media or other solutions or gels, including media, solutions, or gels containing growth factors, chemoattractants, drugs, or test compounds can optionally be provided beneath the substrate where they can permeate the porous substrate.

It is an object of the present invention to reliably, sensitively, and quantitatively measure and monitor target molecules or cells which are in or suspected to be in sample solutions. To this end, electrodes are arranged over the surface of the substrate called the "sensor area" that comprises electrodes and the gaps between electrodes. For monitoring behavior of cells, it is preferred that electrodes be arranged such that, over the "sensor area", there is a distribution of electrodes or electrode elements such that contact and/or attachment of a cell with the substrate in the sensor area has a high probability of resulting in contact and/or attachment of the cell with at least one electrode or electrode element (or portion or portions thereof) on the substrate. In most aspects of the present invention, a substrate (or a portion thereof) will be encompassed by a fluid container (for example a well) in which an assay can be performed. In these aspects, it is preferred that the sensor area of a substrate will include the surface region of a device, which region is enclosed in a fluid container such as a well. That means, when a device is assembled to a fluidic container with the electrode sensor area facing up and the plane on which electrodes are located forming the inner, bottom surface of the fluidic container, the sensor area occupies the entire, inner, bottom surface of the fluidic container. A high probability of a cell contacting an electrode means a greater than 50% probability, preferably a greater than 70% probability, and more preferably a greater than 90% probability.

Thus, in one preferred aspect of the present invention, a device of the present invention comprises more than one electrode structure and can be reversibly or irreversibly attached to a bottomless multi-well plate, for example, such that the substrate of the device forms the bottoms of the wells. A particularly preferred embodiment of the device is a bottomless multi-well plate fitted perpendicularly with tubular fluid containers with opposing open ends which are attached in a fluid-tight fashion to the well bearing surface of the substrate.

The fluid containers of the device, if present, may be of any diameter or size sufficient to retain a biological fluid sample on the electrode sensors of the device. However, using a bottomless multi-well plate fitted perpendicularly with tubular fluid containers with opposing open ends as an example, it will be appreciated that the diameter of the containers at the mouth of the containers should preferably be just larger than the diameter of each well around which the container is disposed.

In an especially preferred embodiment, the diameter of each fluid container disposed around each well on the substrate is larger at the mouth of the fluid container opposite the substrate than at the end of the container attached to the substrate. For example, the diameter of the mouth of the container may be of a size sufficient to permit entry of an automated sample applicator into each container (see, e.g., FIG. 8, element shown at 830).

Using a conventional microtiter plate well (a 96 well plate) as a reference, an example of a suitable diameter for the substrate-attached end of the fluid container would be a diameter between 4 and 7 mm; preferably between 4 and 6.5 mm. In the latter configuration (using a 6.5 mm container diameter for reference), the space between fluid containers in a column of such containers would be approximately 2.5 mm, while the space between fluid containers in adjacent rows of such containers would be approximately 9 mm. The diameter for the substrate-attached end of the container may also be related to the size of the sensor areas (including the electrode elements and the gaps between them). As will be seen below, in a preferred embodiment, the sensor area occupies nearly entire surface region of the device, wherein such surface region is enclosed or will be enclosed within a fluid container. Thus, if the diameter for the substrate-attached end of the container is too large, it will leave very little space for electrode traces extending from electrodes to the ends or edges of the substrate. In one particular exemplary embodiment for a 96 well plate, the diameter for the substrate-attached end of the container is 5 mm and the diameter of the sensor area using, for example, electrodes shown in FIG. 1A, is 5.5 mm. Here the sensor area in FIG. 1A refers to the area defined by the inner diameter of the two arc-shaped, electrically conducting connection traces 125.

Figure 7D:
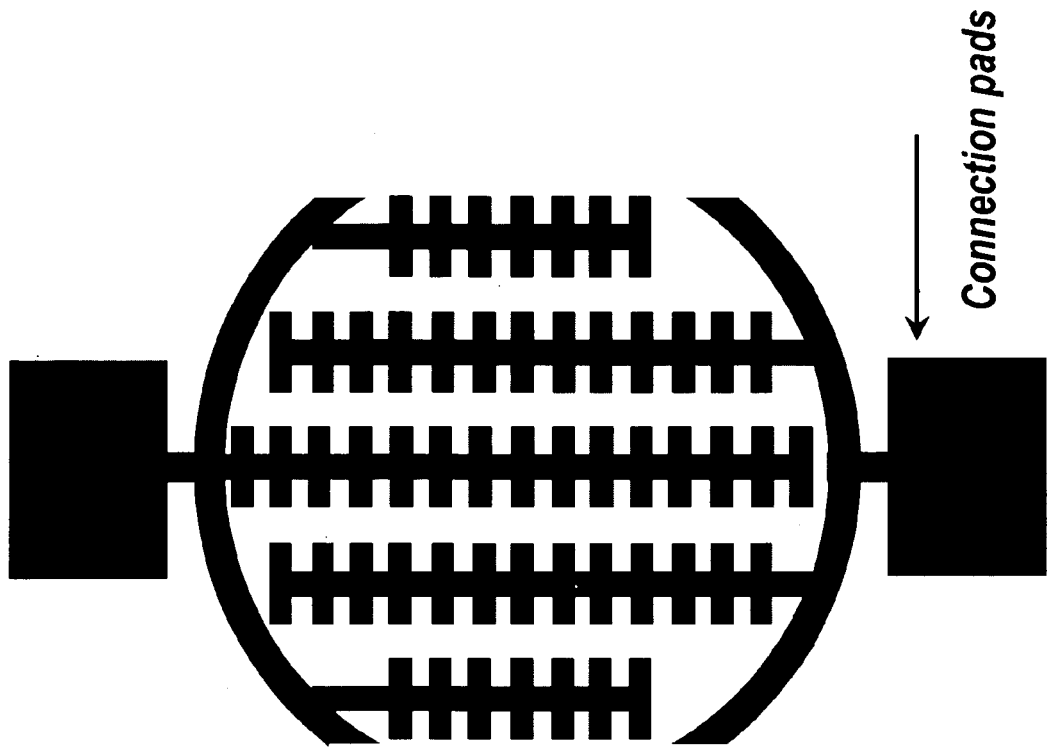
FIG. 7 is a schematic representation of electrode geometries that can be used in the present invention for assaying or analyzing molecules. 7(A), interdigitated, parallel line electrode array, where the electrode width can be larger, equal to, or smaller than the electrode gaps; 7(B) castellated, offset electrode structures; 7(C) electrode structures with disc electrodes added on the electrode lines; 7(D) castellated, straight electrode structures; 7(E) sinusoidal electrode structures; 7(F) concentric electrode structures. The characteristic dimension of the electrodes can be as small as less than 10 microns, or as large as over several hundred microns. The total active electrode area can be of different shapes such as regular shapes like rectangular shapes (FIG. 7(A), 7(B), 7(E)), or circle-like shapes (FIG. 7(C), 7(D)), or other regular or irregular shapes. Preferably, the total electrode-region area (the area including the electrodes and the gaps between the electrodes) covers nearly the complete bottom surface of the top chamber. Electrode structures are connected to impedance measurement circuits (e.g. an impedance analyzer) via connection pads (as illustrated in FIGS. 7(A) and 7(B)) that are either directly linked to electrode elements (FIG. 7(A), FIG. 7(C) and FIG. 7(E)) or connected to electrode elements through additional electrical connection (FIG. 7(B) and FIG. 7(D)).
In FIGS. 7(A), (C) and (E), connection pads are also the electrically-conducting connection traces that connect electrode elements within an electrode structure.
Figure 7C:
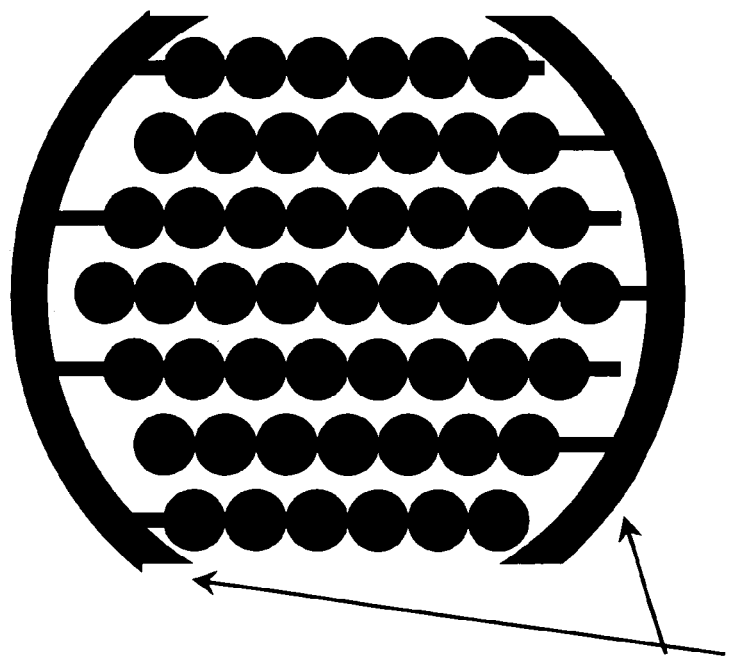
Figures 7E, 7F:
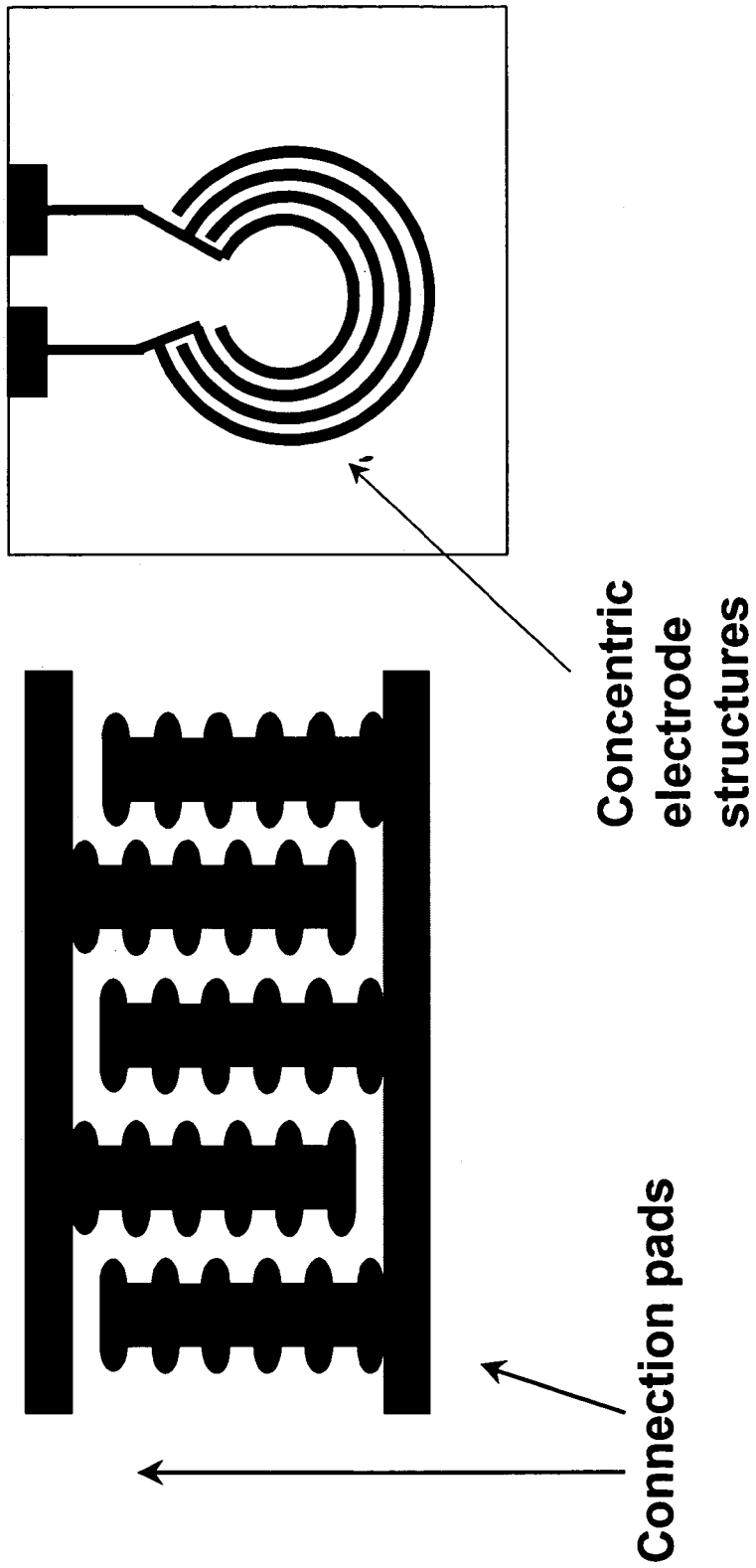
Figure 9:
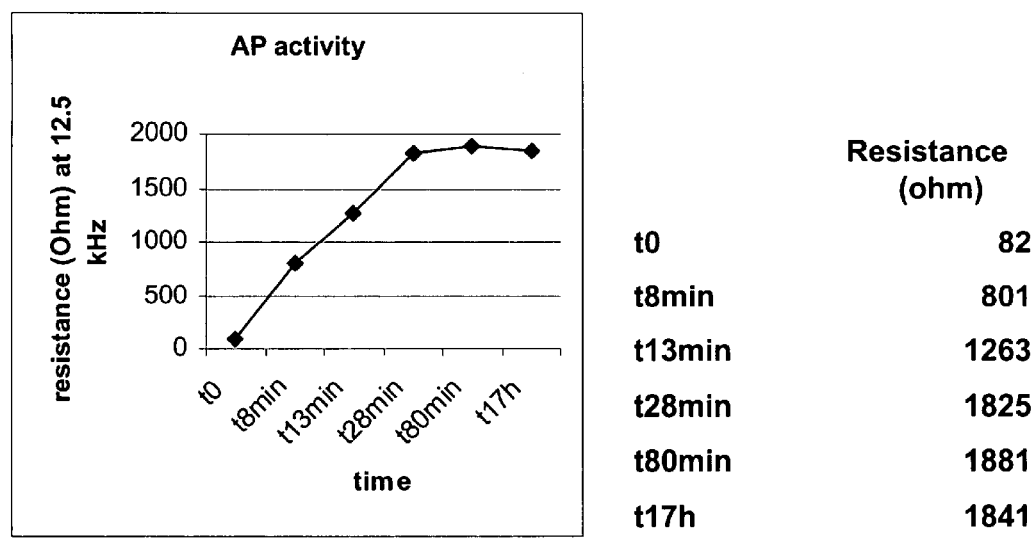
FIG. 9 illustrates the dynamic monitoring of catalytic product precipitation on a device of the invention. The device includes a glass substrate (1 cm squared) on which a microelectrode structure unit was fabricated. Gold (~0.2 micron) over Cr (~0.03 micron) film was deposited on the glass substrate. The microelectrode structure unit having a circle-on-a-line electrode geometry was patterned and fabricated. To use the device, a hollow plastic well having a cylinder shape was bonded to the microelectrode device so that the electrode structure unit was exposed to experiment liquid sample when the sample was added to the plastic well. The surface of the microelectrode was pre-coated with biotinylated bovine serum albumen (BSA) followed by blocking with 3% dry milk at room temperature for 30 min. After brief washing with phosphate buffered saline (PBS), streptavidin alkaline phosphatase (AP, 10 ng/ml) was added and incubate at room temperature for 30 min followed by extensive wash with PBS. Alkaline phosphatase substrate BCIP/NBT (from Sigma, BCIP: 5-bromo-4-chloro-3-indoyl phosphate; NBT: nitroblue tetrazolium) was added to the solution and the resistance between the electrode structures in the plastic well was measured using an electric impedance analyzer. The AP-mediated reactions (AP's substrate BCIP/NBT were converted into precipitants) results in precipitation (see FIG. 8) on the surfaces of electrode structure units. The precipitation caused an increase in the resistance between the electrode structure units. With time, more precipitation occurs on the electrode surfaces and higher resistance was measured. The time-dependent AP activity on the electrode surface was monitored by measuring the time-dependent resistance between the electrode structure units (see FIG. 9).
Figure 10:
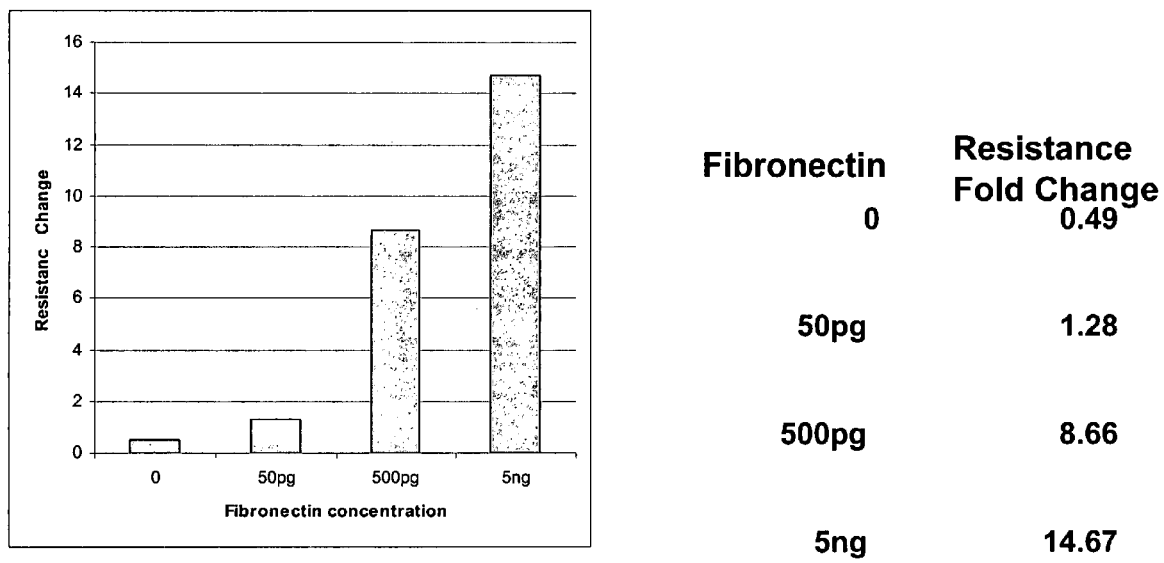
FIG. 10 shows a quantitative detection of fibronectin on a device of the invention by impedance analysis. The device was similar to the one used in FIG. 9. Briefly, the device is a glass substrate (1 cm squared) on which a microelectrode structure unit was fabricated. Gold (~0.2 micron) over Cr (~0.03 micron) film was deposited on the glass substrate. The microelectrode structure unit having a circle-on-a-line electrode geometry was patterned and fabricated. To use the device, a hollow plastic well having a cylinder shape was bonded to the microelectrode device so that the electrode structure unit was exposed to experiment liquid sample when the sample was added to the plastic well. Different amount of fibronectin (5 ng, 500 pg and 50 pg) was added into plastic wells and then incubate at room temperature for 2 hours. This incubation step resulted in the coating of the device surface with fibronectin molecules. The surface of the device was blocked with 3% dry milk at room temperature for 1 hour. After brief wash with PBS, mouse anti-fibronectin (1:200 in dilution) was added to the device and incubate at 4° C. overnight. This overnight incubation resulted in the binding of the mouse anti-fibronectin molecules to fibronectins on the device surface. After washing, alkaline phosphatase (AP)-labeled goat anti-mouse IgG was added and incubate at room temperature for 1 hour followed by extensive washing. This 1 hour incubation resulted in the AP-labeled goat anti-mouse IgG bound to the mouse anti-fibronectin on the device surface. Alkaline phosphatase substrate BCIP/NBT (from Sigma. BCIP: 5-bromo-4-chloro-3-indoyl phosphate; NBT: nitroblue tetrazolium) was added and the resistance between the electrode structures in the plastic well was measured using an electric impedance analyzer. The AP-mediated reactions (AP's substrate BCIP/NBT were converted into precipitants) results in precipitation (see FIG. 8) on the surfaces of electrode structure units. The precipitation caused an increase in the resistance between the electrode structure units. With time, more precipitation occurs on the electrode surfaces and higher resistance was measured. The figure shown the resistance changes at 30 min after adding the substrate BCIP/NBT. The device can detect as little as 50 pg of fibronectin coated onto the surface of the device as indicated in the figure.

The electrodes or electrode elements within an electrode structure in the present apparatuses can have any suitable shape, e.g., a rectangular, circular, a circle on a rectangular line ("circle-on-line"), a square on a rectangular line or a sinusoidal line. They can also take the form of curved lines such as, but not limited to spirals or arcs. Some examples of electrodes, electrode structures or electrode structure units for the device of the present invention are shows in FIGS. 1 and 7.

In some preferred embodiments of the present invention, electrode structures can be interdigitated electrode structures (IDESs) or concentric electrode structures (CCESs), such as those depicted in FIGS. 1B, 1C, 7A and FIG. 7F. For example, an electrode structure can comprise two or more electrodes configured as one or more IDESs or one or more CCESs. Interdigitated electrode structures (IDESs) can be further modified or changed so that the parallel line electrode elements have large perimeter subgeometries, meaning that, as viewed from above, superimposed on the linear electrode elements (which may itself be parallel lines, curved, loop, form angles, turn corners, etc.) are branches, outcroppings, bulges, and the like, giving the linear electrode path a larger perimeter than if its edges conformed to the directionality of the path of the electrode element. Examples of such large perimeter structures are a diamond-on-line electrode structures, circle-on-line electrode structures shown in FIGS. 1A and 7C, astellated electrode structures as shown in FIGS. 7B and 7D. Electrode structures with large perimeter subgeometries are not limited to those depicted herein, and can be regular or irregular, both in the periodicity of the subgeometries and in the shapes of the subgeometries (curves, angles, circles, rectangles) themselves.

Electrodes or electrode elements are preferably distributed over the entire surface of the device they are fabricated on, wherein such surface region is or will be exposed to contact by sample solutions including cells and/or target molecules. In another word, the surface region that is or will be exposed to sample solutions is covered with electrodes (or electrode elements) and gaps between electrodes (or electrode elements). In preferred devices of the present invention, the sensor area can occupy at least 5%, 10%, 30%, 50%, 70%, 80%, 90%, 95% or even 100% of the entire surface region of the device, wherein such surface region is enclosed or will be enclosed within a fluid container. In another word, in preferred devices of the present invention, at least 5%, 10%, 30%, 50%, 70%, 80%, 90%, 95% or even 100% of the surface region that is enclosed or will be enclosed within a fluid chamber and that is exposed or will be exposed to sample solution is covered with electrodes (or electrode elements) and gaps between electrodes (or electrode elements). Preferably, the distribution of electrodes or electrode elements over the sensor area is uniform or approximately uniform.

In embodiments in which a device comprises at least two electrode structures, the two or more electrode elements are preferably arranged in the electrode structures. Where an electrode element is not of rectangular geometry, "electrode width or electrode element width" refers to the averaged dimension of the electrode element that extends in the plane of the substrate (in the direction normal to the major axis of the electrode element) from where it borders one electrode gap to where it borders the electrode gap on its opposite side. Where an electrode gap is not of rectangular geometry, "electrode gap" refers to the averaged dimension of the gap that extends in the plane of the substrate (in the direction normal to the major axis of the gap) from where it borders one electrode element to where it borders the other electrode element on its opposite side.

For monitoring the behavior of cells, preferably, the gap between electrode elements does not substantially exceed the size (e.g. width of cells when they spread and attach on the substrate) of cells whose behavior is to be monitored using the device. This reduces the possibility that contact between a cell and a substrate occurs without the cell contacting at least a portion of an electrode or electrode element. Further, the width of the gap between electrode elements (or the gap size) preferably is not substantially less than the size of cells (e.g. width of an average cell when it spreads and attaches to the substrate) whose behavior is to be monitored using the device, to reduce the possibility of a cell contacting two neighboring electrode elements is measured and thereby giving rise to a somewhat disproportionately large impedance signal, in comparison to a cell contacting only one electrode element. This is particularly important, if the electrode width is much larger (e.g. ten times) than the size of cells whose behavior is to be monitored using the device. On the other hand, if the electrode width is in comparable with the size of cells (e.g. width of an average cell when it spreads and attaches to the substrate), the width of the gap between electrode elements can be somewhat smaller than the size of cells. While other gap dimensions may be used, preferably, the gap between electrode elements of the electrode structures ranges from about 0.2 times and 3 times the width of an average cell used in an assay using the device. Preferably, the width of a gap between electrodes or electrode elements of a device of the present invention used for monitoring eukaryotic cells, such as mammalian cells, such as cancer cells, endothelial or epithelial cells, is between about 3 microns and 80 microns, more preferably between about 5 microns and 50 microns, and most preferably between about 8 microns and 30 microns.

The width of an electrode element is preferably not too narrow since the resistance of the electrode elements will increase as the width of the electrode element decreases. The increased resistance along the electrode elements will cause a large electrical potential difference between different points along the electrode element, resulting in difference impedance signals for cells landed on and attach to different regions of the electrode elements. It is preferred that cells landed on and attached to any region on the substrate surfaces give similar impedance signals. Thus, for an electrode element that is part of an interdigitated electrode structure or concentric electrode structure, where the device is to be used for monitoring eukaryotic cells, such as mammalian cells, such as cancer cells, endothelial or epithelial cells, the electrode width is preferably greater than about 3 microns, and more preferably greater than about 10 microns. The width is also limited by the consideration that if an electrode element is very wide, a cell that is positioned over a central part of such a very wide electrode will result in a small impedance signal when compared with that of a cell that is positioned over the edge of an electrode, where the field strength can be significantly higher. Preferably, an electrode element's width is between about 0.5 times and about 10 times the size (e.g., the width of an average cell when it spreads and attaches to the substrate) of cells used in an assay that uses the device. Preferably, for an electrode element that is part of an IDES or CCES, where the device is to be used for monitoring eukaryotic cells, such as mammalian cells, such as cancer cells, endothelial or epithelial cells, an electrode or electrode element is less than about 500 microns wide, and is preferably less than about 250 microns wide. In some preferred embodiments of the present invention, an electrode element is between about 20 microns and about 250 microns wide.

In the present application, it is preferred that the electrode gap between electrode elements should be designed with respect to the electrode width. While other ratios of the electrode element width to gap may be utilized, preferably, the ratio of electrode element width to gap width is between about 1:3 and 20:1. Preferably, the electrode element width is between 1.5 and 15 times the gap width. More preferably, the electrode element width is between 2 and 6 times the gap width; for example, if the electrode width is 90 microns at the widest point of each electrode, the gap width would be about 20 microns at the widest point of the gap between adjacent electrodes. For the present application, the electrode width can range from less than 5 microns to more than 10 mm. Preferably, the electrode width is in the range between 10 micron and 1 mm. More preferably, the electrode width is in the range between 20 micron and 500 micron.

The electrode elements within an electrode structure can be connected with each other by any electrically-conducting connection traces. For example, the electrode elements 110a, 110b and 110c within the electrode structure 110 of FIG. 1A are connected to each other by the arc-shaped, electrically conducting connection traces or electrode buses (125). Since such electrically conducting connection traces (electrode buses) may have different geometries (thus having different electric field strength and distribution) from that of the electrode elements, molecular reactions on (or cell attachment to) these connection electrode buses may result in different impedance signals from molecular reactions on (or cell attachment to) electrode elements. Although not a limitation or requirement, in some applications it is preferred that molecular reactions do not occur on these electric connection traces (electrode buses). Similarly, it is preferred that cells do not attach to these electrode buses. Thus, such connection traces may have an electrically insulating coating so that molecular reactions on or cell attachment to these connection trace regions will not result in a change in impedance between or among electrodes. In some embodiments, the electrode buses or electrically-conducting connection traces (e.g., 125 and 225 in FIGS. 1A and 1B) to connect the electrode elements may be located outside the bottom surface of a fluidic container or well that comprise the electrode structure. In this way, when sample solutions are added into the fluidic container or well, molecular reactions (or cell attachment) will not occur on such electrical connection traces. Taking the electrode structure 110 in FIG. 1A as an example, the inner diameter of the arc-shaped, electrically conducting connection traces may have a diameter of 1.2 mm. This exemplary device is assembled to a plastic, cylinder shaped, fluidic container which has openings on both ends. The inner diameter of the cylinder-shaped fluidic container may be 1 mm. Using a double-sided adhesive (for example, a pressure-sensitive-adhesive), the electrode device can be bond to the fluidic container. The electrode area is concentrically aligned with and bond to a circular end of the fluidic container. Thus, the 1.2 mm diameter will be located outside of the bottom surface of the container.

Non-limiting examples of materials for electrodes or electrode elements are indium tin oxide (ITO), chromium, gold, copper, nickel, platinum, silver, steel, and aluminum. Electrodes can comprise more than one material. Choice of appropriate materials for making electrodes depends on several factors: whether the material is conductive enough, how difficult it is for patterning such material on a substrate, whether the material can be reliably used for performing molecular detection assay of the present invention.

Electrode or microelectrodes of the present invention can be of any electrically conductive material. For example, gold (Au), platinum (Pt) can be used. When substrates such as glass and/or plastics are used, an adhesion layer of metal such as Cr and Ti can be used. In order to reduce the electric resistance of the electrodes, electrodes with conductive thin films are desirable to have certain thickness. As a non-limiting example, electrodes can be made with a 300 Angstrom Cr layer overlaid by 2000 Angstrom Au. Since such electrode layers will be optically non-transparent, the molecular interactions occurring on this type of electrode surfaces cannot be monitored directly with optical means if the optical detection requires the light transmission through the substrate surface on which electrodes are incorporated into. Similarly, the cells attached or adhering to thus type of the electrodes cannot be monitored directly, either. For this reason, in some embodiments of multiwell plate comprising electrode structures for impedance monitoring of molecular reactions, some of the wells in the multiwell plates are electrode-free so that molecular reactions or cells attached or grown in these wells can be readily monitored by optical measurement methods. For molecular reactions to be monitored by optical measurement methods, molecules in the reactions may have to be labeled with certain optical labels such as fluorescent molecules or other optical-detectable molecules. The above thickness of gold (Au) and chromium (Cr) thin films for electrodes is used as an illustrative example. The thickness of the thin conductive films can be other values, provided that the resulting electrodes and/or electrode structures can be used for measuring molecular reactions. Similarly, the thin conductive films can comprise other conductive materials, e.g. platinum over titanium.

Alternatively, optically-transparent electrodes can be used in a device of the present invention so that the electrodes can not only monitor molecular reactions (and cell substrate impedance) but also permit optical evaluation and inspection of sample solutions under an optical microscope of any kind or by other optical detection means. Preferably, the substrate material on which optically-transparent electrodes are fabricated is also optically transparent, for example, a substrate material can be polycarbonate or polystyrene or polyester or glass. In addition, such electrodes and substrates have other important capabilities in which the electrodes and substrates can coordinate with other conventional optical detection means for molecules or cells. Thus, the present invention introduces the novel and surprising feature of substrates having optically-transparent electrodes that can allow optical observation and measurement of solutions whose constitute molecules can be electrically monitored or measured in the same assay plate, container, or well. Using such optically transparent electrodes, the present invention allows for optical observation of cells whose behavior can be electrically monitored in the same assay plate, container, or well. For example, cells can be cultured in a chamber or a well or plate comprising a device of the present invention having optically-transparent electrodes on the substrate. Cell growth or behavior can be monitored or assayed based on cell-substrate impedance. During or after electrical monitoring of cells, the still intact cells (either viable or non-viable) can then be used for further molecular, cellular, or biochemical assays. For example, gene expression assays can determine the identity of genes expressed (and the level of expression) for a particular cell-based assay, enzymatic assays can measure how many cells are viable or non-viable, and apoptosis assays can detect how many cells are in various stages of apoptosis.

Examples of optically transparent electrodes include indium-tin-oxide (ITO). With appropriate thickness of ITO layer, the transmittance of light through an ITO film electrode can be as high as 98%. In other cases, sufficiently thin conductive films (e.g. a very thin gold film) can be used as optically transparent electrodes.

Ordinarily, the present apparatuses should have a surface area sufficient for attachment or growth of multiple cells. In one example, the present apparatuses can have a surface area sufficient for attachment or growth of at least 10, and more preferably at least 50 cells. In another example, each pair of the electrodes or each pair of electrode arrays within a present apparatus (e.g. electrode array 110 and 120 in FIG. 1) that is connected to an impedance analyzer can have a surface area sufficient for attachment or growth of at least 10, and more preferably at least 50 cells.

The electrode elements, the electrodes, the electrode structures and the electrode structure units in the present apparatuses can have any suitable configurations, surface areas or surface modifications. In one example, at least one of the electrode structures can have at least two electrode elements. In still another example, the electrode or electrode structure surface area can be modified with a cell-adhesion promotion moiety. Any suitable cell-adhesion promotion moieties, such as a self-assembly-monomolecular (SAM) layer (e.g. alkanethiolates on gold and alkylsiloxanes on $SiO_2$ or $SiO_x$,), a protein (e.g., fibronectin, gelatin, collagen, laminin, proteins that promotes specific or non-specific cell attachment to the electrode or electrode array surface area), a peptide (e.g., poly-L-lysine), a polymer layer and a charged group, can be used in the present apparatuses. In yet another example, the non-electrode or non-electrode-array surface area can be modified with a cell-adhesion repelling moiety, e.g., certain polyethylene glycol formulations.

Preferably, the electrodes, electrode structures, and electrode elements are configured such that the electrode traces lead from the electrodes at the substrate surface to an edge or end of the substrate, where they can be connected with a line from an impedance measurement circuit or a signal source. Here the edge or the end of the substrate where the electrode traces end may correspond to the connection pads on the substrate. In preferred aspects of the present invention, the trace or traces from electrode elements of one electrode structure are insulated from the traces from electrode elements of another electrode structure. In one type of arrangement, electrode traces are located on separate regions of the substrate such that they do not contact each other where their paths cross. In another arrangement, where electrode traces need to cross each other, an insulating material layer can be sandwiched between the electrode traces. Fabrication of such apparatuses or device may involve multi-layer microfabrication processes.

Figure 17:
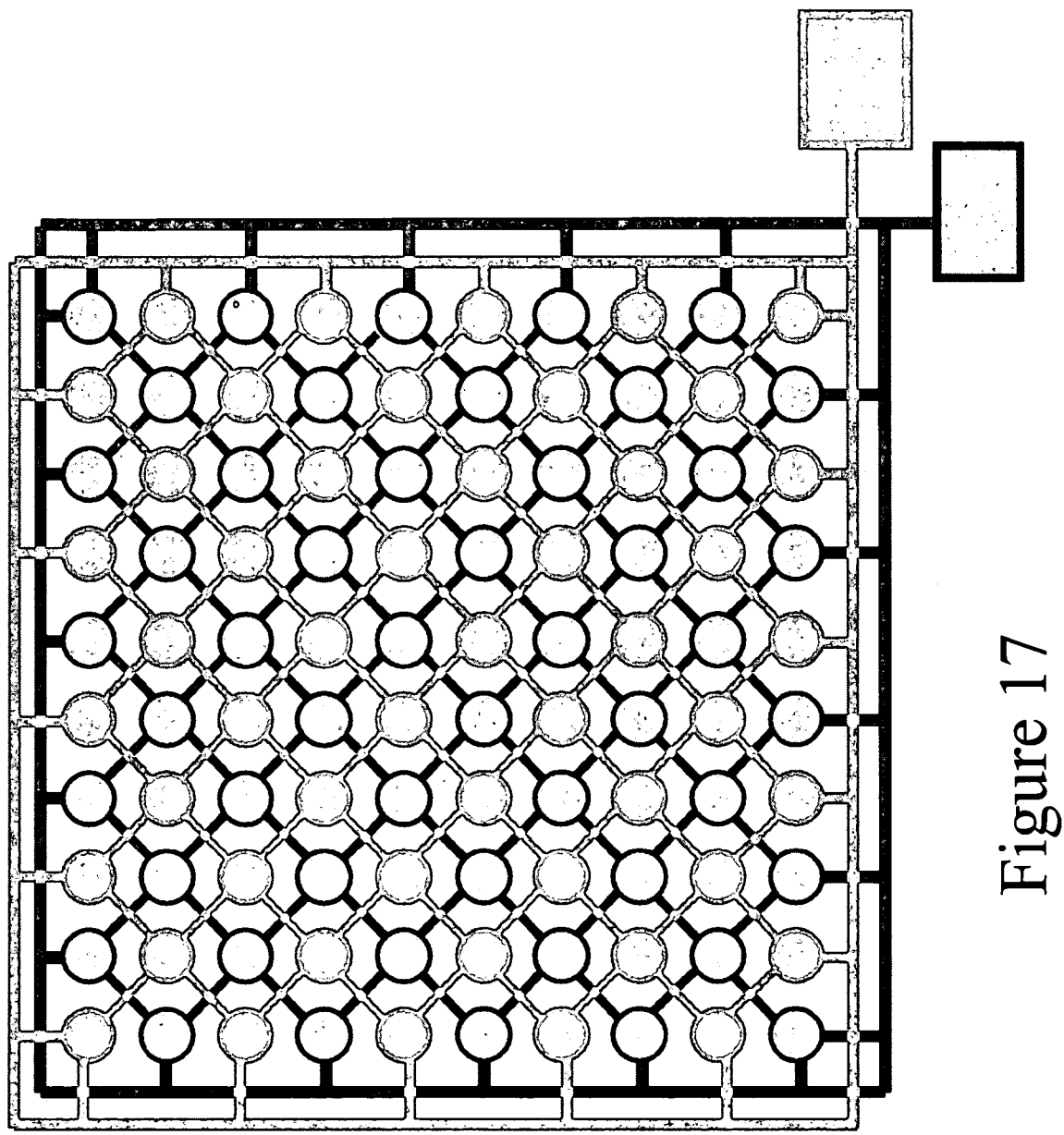
FIG. 17 shows a multi-layered electrode structure.

FIG. 17 shows an example, in which multiple-layered electrode structures are made on a substrate. Here the electrodes for monitoring molecular reactions on the electrode surfaces (and for monitoring cell attachment/growth) are an array of circle-shaped electrode elements with alternatively connected to two connection pads, which can be operatively connected to an impedance measuring circuit. Electrically conductive connections among the circle electrode elements within each of the two sets of electrode elements cross each other and are located on different layers between which layers an insulating or nonconductive layer exists to achieve electrical isolation between these two sets of circle electrodes. Similarly, electrode traces connecting the electrode elements to the connection pads also cross each other and are located on different layers between which layers an insulating layer exists. Other examples of multiple layer electrode structures can be found in the literature, for example in "Positioning and manipulation of cells and microparticles using microminiaturized electric filed traps and traveling waves", by Fuhr et al, in Sensors and Materials, Vol. 7, No. 2, pages 131-146, 1995 and in U.S. Pat. No. 6,448,794, entitled "Apparatus and method for high throughput electrorotation analysis.

The present apparatuses can further comprise one or more impedance analyzer connected to one or more connection pads. Electrode can directly or indirectly connect to a connection pad, where they connect to a line from a signal source. A connection pad is preferably at the edge or perimeter of a device of the present invention, but this is not a requirement of the present invention. The connection between electrodes and a connection pad can optionally be via a connecting path that can be localized to an end of the substrate. In most uses of an apparatus or device of the present invention, a device will be part of, attached to, or within a plate or a fluid container that can contain sample solutions. In these embodiments a connection pad can be situated on a fluid container or plate comprising one or more fluid containers, preferably near or at one or two ends of the substrate (see, for example, FIG. 15, 16).

Depending on the uses, the present apparatuses or devices can be in any suitable size. In one example, the present devices can have a size to be fitted into a single well of a multi-well microplate, e.g., a 6-, 12-, 24-, 48-, 96-, 192-, 384-, 768- and 1,536-well plate. In another example, the present apparatuses or devices can have a size compatible to a multi-well microplate and can have multiple pairs of electrodes spatially arranged according to wells of a multi-well microplate, e.g. a 6-, 12-, 24-, 48-, 96-, 192-, 384-, 768- and 1,536-well plate. In another example, the present devices can have a size compatible to a bottomless multi-well microplate and can have multiple pairs of electrodes spatially arranged according to wells of a multi-well microplate, e.g., a 6-, 12-, 24-, 48-, 96-, 192-, 384-, 768- and 1,536-well plate. The device can be reversibly or irreversibly attached to a bottomless multi-well microplate such that portions of the device form the bottoms of wells. In some embodiments, the electrode area for electrode structures comprised in a well of these multi-well plates is larger than the diameter of the well. Thus, after the present devices are bonded or attached to the bottomless multi-well plates, the electrode area covers the entire surface of the bottom surface of the well. In other embodiments, not all the wells have electrode structures for impedance-based monitoring of molecular reactions. This is particularly useful when the electrodes are made of optically non-transparent materials. For example, in FIG. 16(B), a 96 well plate has 92 wells comprising measuring electrode structures whilst the four corner wells are electrode-structure free so that the molecular reactions in these wells can serve as controls, and can be monitored using optical microscope or other optical detection means. Similarly, with the plate in FIG. 16(B), the 92 wells permit the impedance-based monitoring of the cells whilst the four corner wells are electrode-structure free so that the cells grown or cultured in these wells can serve as controls, and can be monitored using inverted, optical microscope.

The present apparatuses can have any suitable number of electrodes. For example, the present apparatuses can have at least four electrodes fabricated to substrate and wherein each of the electrodes has at least three neighboring electrodes and the electrode impedance is measured between one electrode and its at least three neighboring electrodes. Preferably, each of the electrodes has a surface area sufficient for attachment or growth of at least 10 cells.

In one embodiment, the electrodes or electrode arrays of the present apparatuses can comprise a built-in application-specific-integrated-circuit (ASIC). Preferably, the ASIC comprises a switching circuit, an impedance measurement circuit and a power source.

In another embodiment, the present apparatuses can comprise an impedance measurement circuit. The impedance measurement circuit is equivalent to an impedance analyzer that can measure the impedance between or among electrodes in the apparatuses of the present invention. Preferably, the present apparatuses can further comprise a switching circuit.

In still another embodiment, at least one pair of the electrodes or one pair of electrode arrays of the present apparatuses is individually addressed in terms of connecting to an impedance analyzer or an impedance measurement circuit. Impedances are measured between such a pair of the electrodes or such a pair of electrode structures with or without molecular reactions occurring on the surfaces of the electrode(s) or electrode structure(s). "Individually addressed" means that the electrode impedance can directly be connected to such a pair of electrodes or electrode structures.

In yet another embodiment, the sensor areas comprising electrodes or electrode structures or arrays of the present apparatuses occupy at least 1% of the entire surface of the apparatus. In another embodiment, the sensor areas of the present apparatuses occupy 2%, 5%, 10%, 30%, 50%, 70%, 80%, 90%, 95% or even 100% of the entire surface of the apparatuses exposed to sample solutions during an assay that uses the apparatuses.

In yet another aspect, the present invention is directed to a multi-well microplate for monitoring molecular reactions, which microplate comprises a plurality of wells, at least one of the wells comprising an above-described device for monitoring molecular reactions.

In yet another aspect, the present invention is directed to an above-described apparatus for impedance-based monitoring of cell behavior, which comprises at least 10 cells, and preferably at least 50 cells that are attached or grown on its surface.

In yet another aspect, the present invention is directed to a multi-well microplate for impedance-based monitoring of cell behavior, which microplate comprises a plurality of wells, at least one of the wells comprising an above-described device for monitoring cell-substrate impedance.

One well, multiple wells or all the wells of the present microplate can have one or more above-described device(s) for monitoring molecular reactions or cell behaviors. In one example, at least one of the wells comprises one above-described apparatus for monitoring molecular reactions (or cell behavior).

The electrodes or electrode structures comprised in the present microplate can be arranged in any suitable ways. In one example, at least one pair of the electrodes or one pair of electrode structures of at least one device is individually addressed in terms of connecting to an impedance analyzer or an impedance measurement circuit. In another example, the electrodes or electrode arrays of the apparatus(es) are arranged in a row-column configuration. Such multi-well microplate can be connected to a switching circuit or further comprise a switching circuit, e.g., an electronic switch circuit for each well. The switching circuit can also be arranged in a row-column configuration. In still another example, at least one of the electrodes or electrode structures from at least two wells can share common electrical connection pad(s) located on the microplate of the present invention. In yet another example, the connection pads in the apparatus(es) can be connected to a flex circuit. In this case, the flex circuit is a circuit board for electrical connection between an impedance measurement circuit or impedance analyzer to connection pads on the present microplate or the present apparatuses for monitoring molecular reactions and for monitoring cell behaviour. The flex circuit is made of flexible materials (e.g. a flex circuit is made of a thin copper layer sandwiched between two polyimide layers). The sensor area within a well of a microplate can cover any suitable percentage of the bottom surface area of the microplate well. For example, the sensor area comprising electrode elements, electrodes or electrode arrays can occupy at least 1% of the entire bottom surface of the microplate well. Preferably, the sensor area can occupy at least 5%, 10%, 20%, 30%, 40%, 50%, 60%, 70%, 80%, 90%, 95%, 99% or 100% of the entire bottom surface of the microplate well.

The present multi-well microplate can have any suitable number of wells, e.g., 6, 12, 24, 48, 96, 192, 384, 768 and 1,536 wells. To produce sensor electrodes in a multiwell plate configuration, various assembly approaches can be utilized.

In one approach a bottomless plate can be bonded to electrodes or electrode structures fabricated on a non-conducting substrate such as glass or plastic. Taking an example of 96 well plates, the substrate can be a single piece of plastic or glass on which all electrode structures can be fabricated. In another example the substrate can be assembled from multiple separated substrates (e.g., 2 substrates each corresponding to total 48 wells, 3 substrates each corresponding to 32 wells, 4 substrates each corresponding to 24 wells, 6 substrates each corresponding to 16 wells, 8 substrates each corresponding to 12 wells, 12 substrates each corresponding to 8 wells, etc). The substrate comprising electrode structures to be assembled to 96 well configuration can either same types of substrates or dissimilar types of plates. Dissimilar types of the substrates refer to that the substrates can be different in size and/or different in number of electrode structures.

Figure 15A:
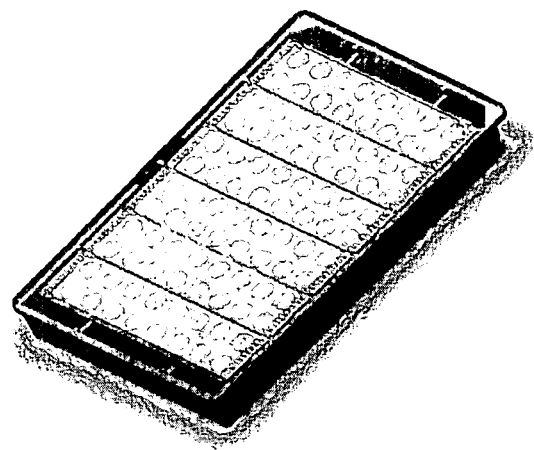
FIG. 15(A) shows a bottom view of a 96-well plate with six device assembled on the bottom. Each device has 16× electrode-structure units with connection pads located on the edges of the device.
Figure 15B:
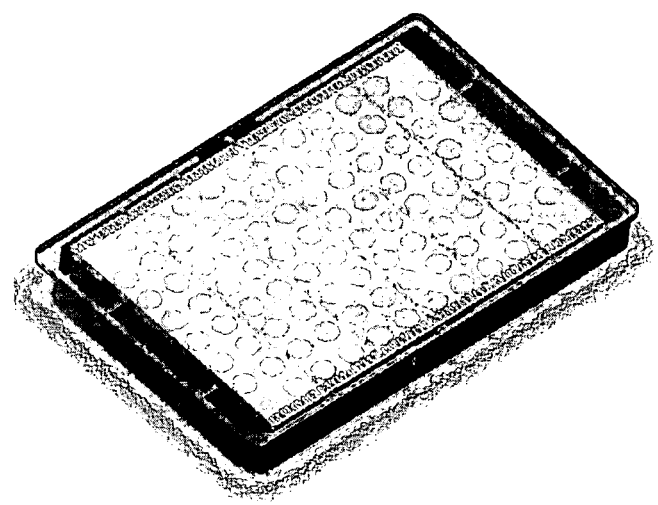
FIG. 15(B) shows a bottom view of a 96-well plate with six device assembled on the bottom. Each of the middle four devices has 16× electrode-structure units with connection pads located on the edges of the device. The two side devices have 14× electrode-structure units with connection pads also located on the edges of the device.

The following is an exemplary embodiment in which a 96× well plate is assembled by using bottomless plates bonded to six substrates on which microelectrodes are fabricated or incorporated. Each of six substrates may comprise up to 16 different electrode structures, each of which correspond to one of the 16 wells. FIG. 15A shows an individual substrate plate, on which 16 electrode structure units can be fabricated and incorporated. FIG. 15B shows an individual substrate plate, on which 15 electrode structure units can be fabricated and incorporated. The electrode structures on the substrates (e.g. a plastic substrate, a glass substrate) may be fabricated using various methods including, such as, photolithography method and laser ablation method. In one exemplary embodiment, the substrate dimension may be about 77.2 mm by 17.75 mm. The electrode structures are of thin gold film (~0.2 micron thick) over a thin Cr film (~0.03 micron thick). Electrode geometry may be a circle on line electrode configuration with dimension of 30/80/90 (microns) for electrode line width, electrode line gap and circle diameter) or other geometry.

Assembly of such electrode-containing substrates to a plastic, bottomless plate can be achieved by using liquid type of adhesive, PSA (pressure sensitive adhesive), or plastic ultrasonic welding, or any other suitable bonding methods.

For liquid adhesive to be used to assemble the electrode-containing substrate to the bottomless multi-well plate (or simply, well plate), the adhesive can be accurately dispensed on the bottom side around each well with, for example, an automatic liquid dispensing machine. In this operation for dispensing the liquid adhesive, the well plate may be positioned upside down. Then each substrate comprising up to 16 electrode structure units can be accurately positioned on the bottom-less well plate by, for example, a pick-and-place machine. After the liquid adhesive is cured, the substrates are bonded to the bottomless well plate. Another method for bonding these plates using liquid adhesive may take the following steps: (a) accurately positioning the electrode-containing substrates on the well plates with a small distance (e.g. 100 micron) between them; (b) applying liquid adhesive with appropriate viscosity to the edge of the electrode-containing substrates, with capillary force, the liquid adhesive may be automatically moved into the space between the electrode-containing substrates and well plate. The liquid adhesives filled in the gap between the electrode-containing substrate and the well plate may then be cured.

For the pressure sensitive adhesive (PSA) approach, the double-sided adhesive with supporting liners on both sides is first cut with holes that correspond to the well bottom size of the multi-well, bottomless microplate. Then after peeling off the liner on one side of the PSA, the PSA is accurately positioned over and pressed against the bottom-side of the multi-well plate. The other liner can be removed. The individual electrode-containing substrates can be positioned with aligning electrodes or electrode structures to individual wells in the multi-well plate.

FIGS. 16(A) and 16(B) show a bottom view of 96-well plates with six electrode-containing devices assembled on the bottom. For FIG. 16(A), each device has 16× electrode-structure units with connection pads located on the edges of the apparatus (attachment of the connection pads at opposing ends of the apparatus is preferred). For FIG. 16(B), each of the middle four devices has 16× electrode-structure units with connection pads located on the edges of the device. The two side devices have 14× electrode-structure units with connection pads also located on the edges of the device. For clarity, the details of electrode structures and electrical connection between the connection pads and electrode structures are not shown in these figures.

Figure 13:
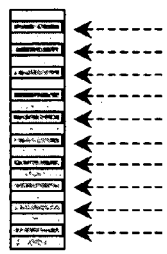
FIG. 13(A) shows a small PCB board that can be used for connecting to the connection pads on the edges of the substrate having 16× electrode-structure units shown on FIG. 12(A). The PCB board has 16 rectangular conductor lines that were arranged according to the spacing between the connections pads shown on FIG. 12(A).
FIG. 13(B) shows the assembly with two PCB boards bonded to the substrate having 16× electrode structure units.
FIG. 13(C) shows the assembly with two PCB boards bonded to the substrate having 6× electrode structure units, with needle shaped POGO-pin connection from underneath to connect to the conductor lines.
Figure 13:
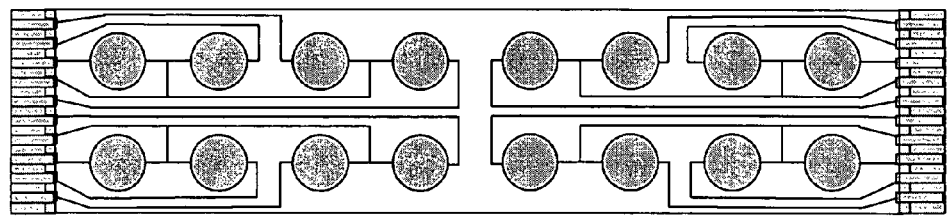
Figure 13:
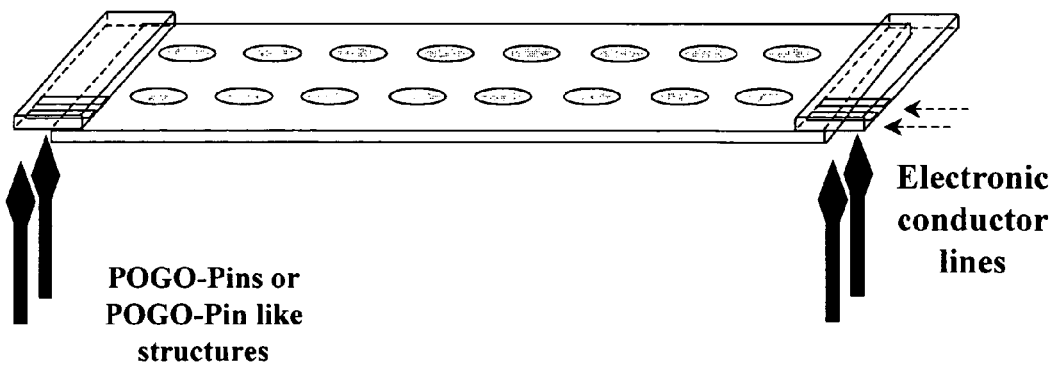
Figure 14:
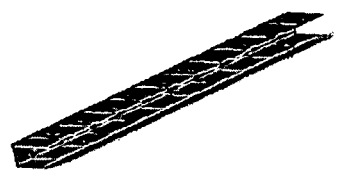
FIG. 14(A) shows a flex circuit that can be used for connecting to the edges of the sensor plates. The flex circuit has multiple, rectangular-shaped, electrical conductors on both sides where the electrically conductors on one side can be bonded to the connection pads on a device shown in FIG. 12(A) whilst the electrical conductors can be connected to an impedance measurement circuits. The corresponding electrical conductors on both sides of the flex circuit are connected.
FIG. 14(B) shows assembly of the flex circuit bonded to a device as shown in FIG. 12(A). The electrical conductors on one side of the flex circuit are bonded to the connection pads of the device.
FIG. 14(C) shows the assembly with two flex circuits bonded to the substrate having 6× electrode structure units, with needle shaped POGO-pin connection from underneath to connect to the conductor lines.
FIG. 14(D) shows one type of metal clip that is made of metal wires and can be used to connecting to connection pads on one side of substrate to the other side of the substrate.
FIG. 14(E) shows that a crossectional view of metal clips connected to the connection pads along edges of the substrate to the other side of the substrate (i.e., the bottom side of the substrate here). The substrate comprises electrode structures on the same side of the substrate as the connection pads are located on. Needle shaped POGO-pin connection structures that are electrically connected to an impedance analyzer (directly or through electronic switches) can then be used to connect to the metal clips on the bottom side so that the impedance analyzer is connected to the electrode structures on the substrate.
FIG. 14(F) shows another type of metal clip that is made of metal wires and can be used to connecting to connection pads on one side of substrate to the other side of the substrate. The extra-bend for this type of metal clips allows them to be connected to (for example, by soldering) to connection pads on a printed circuit board.
FIG. 14(G) shows that a crossectional view of metal clips connected to the connection pads along edges of the substrate to the other side of the substrate (i.e., the bottom side of the substrate here). The metal clips are then connected a printed circuit board to which an impedance analyzer can be connected to directly or indirectly (for example, via electronic switches).
Figure 14:
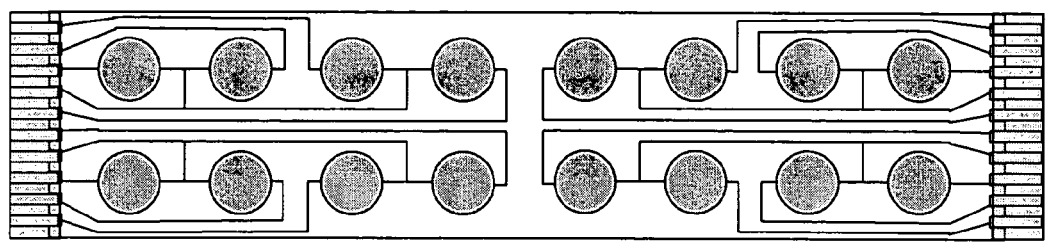
Figure 14:
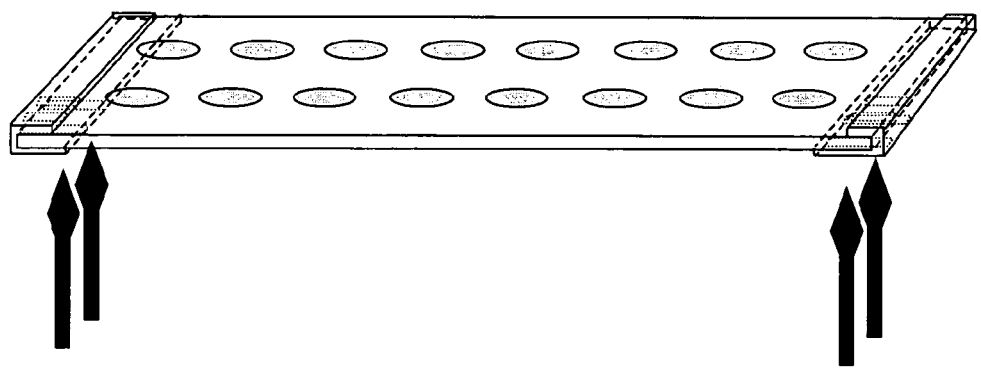
Figure 14:
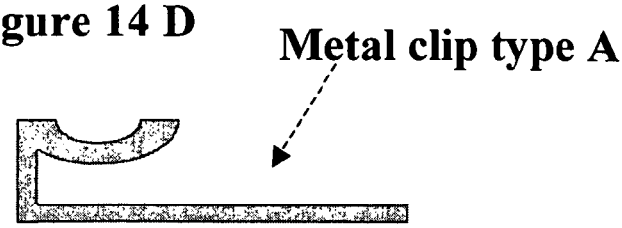
Figure 14:
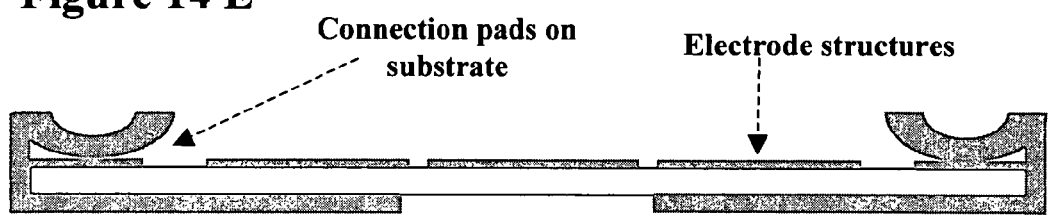
Figure 14:
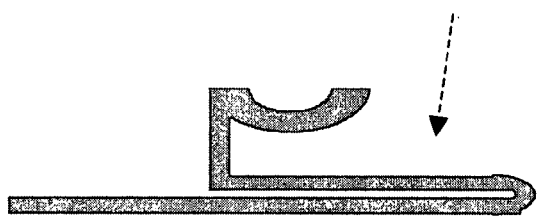
Figure 14:
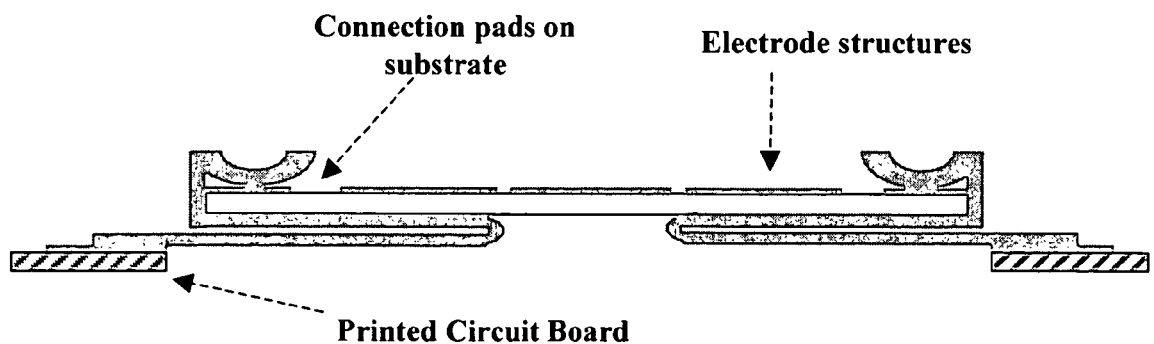
Figure 16:
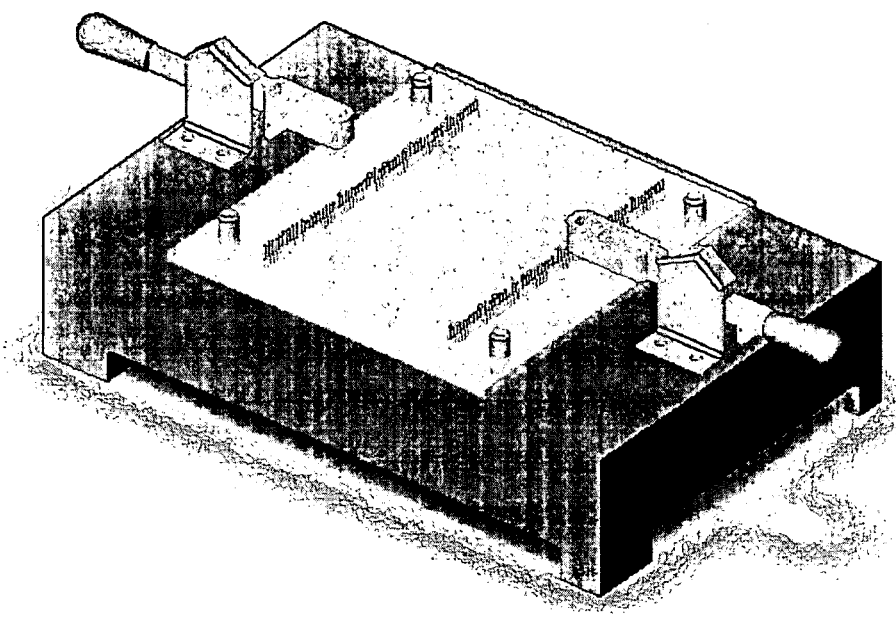
FIG. 16 shows a POGO-pin holder structure that can hold multiple POGO-pins. This structure can be used with the 96-well plates illustrated in FIGS. 15A and 15B.

Electronic connection from such multi-well plates to external impedance analyzer present a significant challenge because of limited space on the bottom side of these plates. The electrode structures are facing upwards in operation. In one exemplary embodiment for connecting electrode structures to external impedance analyzers, the electronic connection pads are located at the ends of the electrode-containing substrates (see, for example, FIGS. 12A and 12B). Because of very limited spaces available along the bottom edges of the multi-well plate, connectors used in the electronics industry cannot be directly used to such devices. In addition, because of the frame of the multi-well plate, there may not be space available for electronic connections from the top side to the connection pads at the ends of the electrode-containing substrates. For this reason, specific design is required for connecting the up-facing the connection pads to become bottom-facing. In one approach, a small PCB board (see FIG. 13A) with straight-line conductor lines is down-facing and one end of all the conductor lines is conductively-bonded to the connection pads (see FIGS. 13B and 13C). Then the other end of the conductor lines can be accessed from the bottom. For example, a long, conductive needle (e.g. a POGO pin, details may be found in website such as http://www.emulation.com/pogo/) pin can be used (see FIG. 13C). FIG. 16 shows a schematic drawing of a POGO-pin holder structure where POGO pins can contact-connect to the conductor lines of small PCB board shown in FIGS. 13(A) and 13(C). In another approach, a Flex circuit approach may also be used. In this case, one end of the flex circuit can have metal rectangular wires spaced at the corresponding distances and can be conductively bonded to the edge of the plate (FIG. 14A). The Flex circuit can be wrapped around the edges to the bottom side of the sensor plate (FIGS. 14B and 14C). The other end of the flex jumper is also metal line and can be accessed by needle structured conductors (FIG. 14C). The flex circuit shown in FIG. 14C is a certain number of metal wires (10 wires in FIG. 14C) assembled to a plastic sheet. In similar approach (FIG. 14D, 14E), metal wires (i.e., electrical connection pins) in the form of shorting clip (metal clips) can be used for similar purpose of connecting electrode pads on the top surface of the substrate to the bottom surface side. Details of an exemplary shorting clips can be found in http://www.nasinterplex.com/short_clips/short_set.html. In yet another approach, wire bonding could be used to connect the connection pads located on the electrode-containing substrate to a small PCB board. The PCB board has conductive vias on it so that the electrical connections can be made to the PCB board from bottom side.

In another exemplary embodiment, the connection pads are connected to conductive lines either along the edge of the wells, or between the wells, to the top side of the bottom-less plate. Then, the electronic connections can be performed from the top side.

Figure 4A:
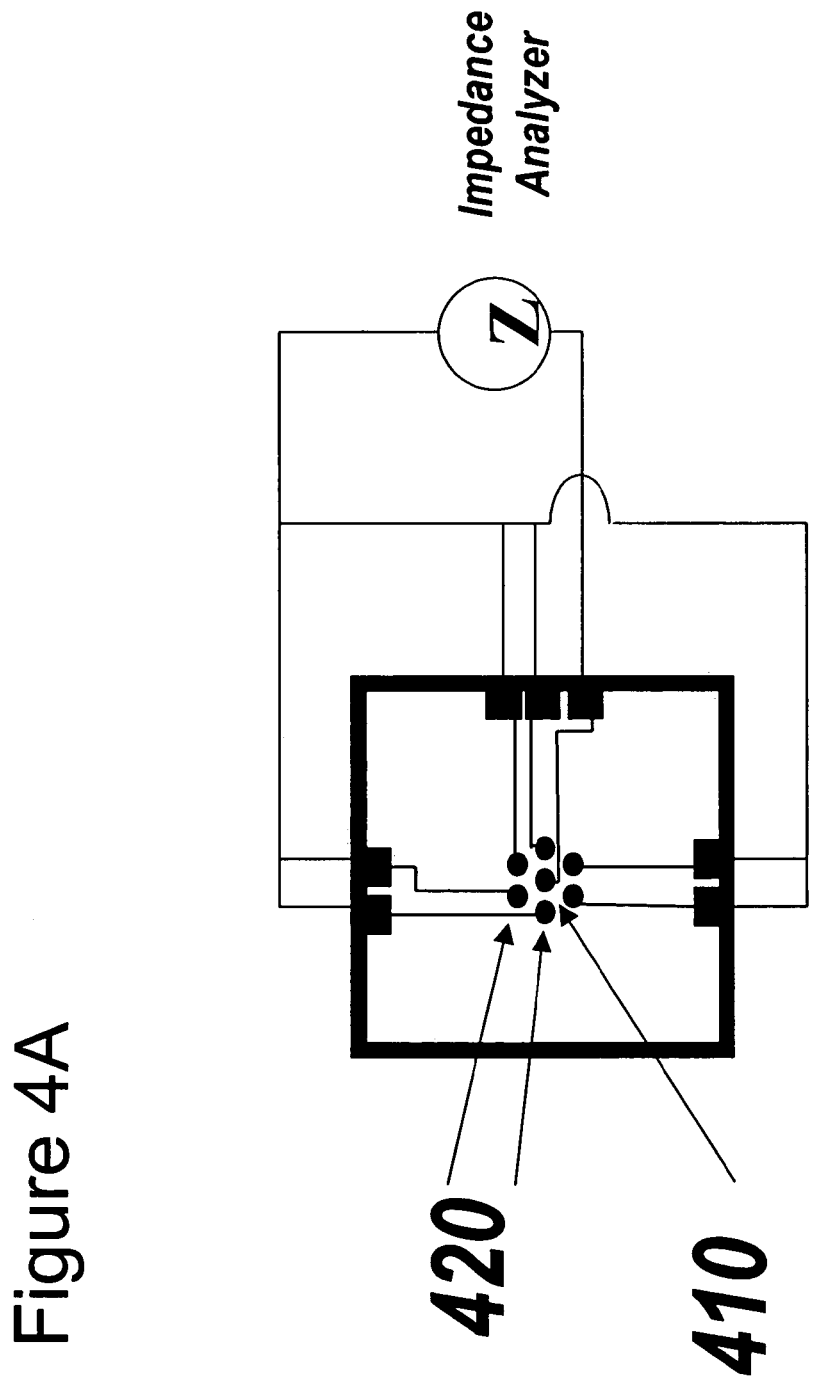
FIG. 4A is a schematic representation of a device for measuring the molecule-binding impedance between one single electrode and its neighboring electrodes. In the figure, the disc-shaped electrode 410 has six neighboring disc-shaped electrodes 520. The impedance between the disc-shaped electrode 410 and all electrodes 420 (that are connected together outside the device) is measured.
Figure 4B:
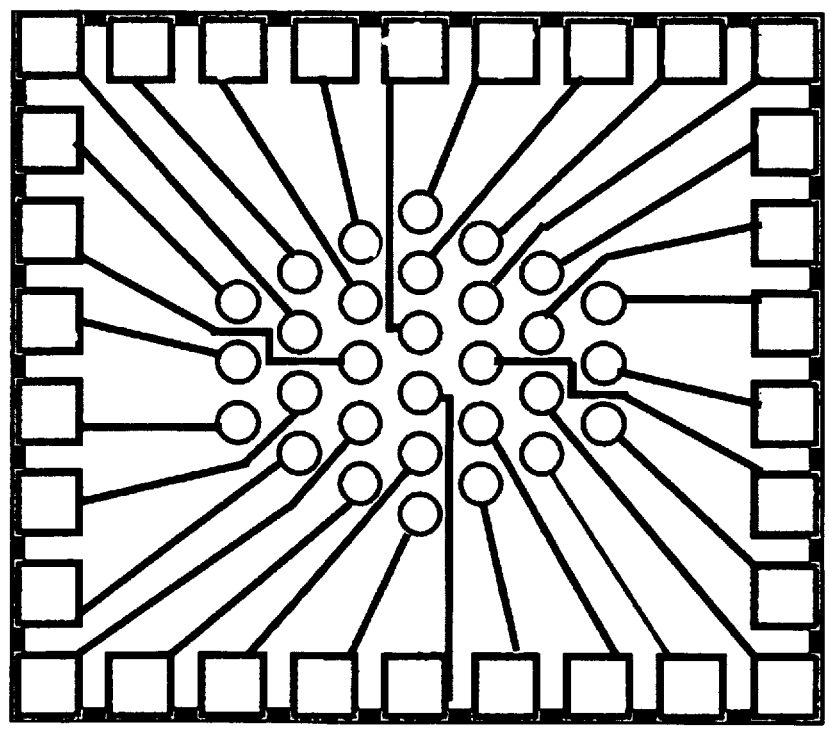
FIG. 4B is a schematic representation of a device with multiple disc-type shaped electrodes.
Figure 5:
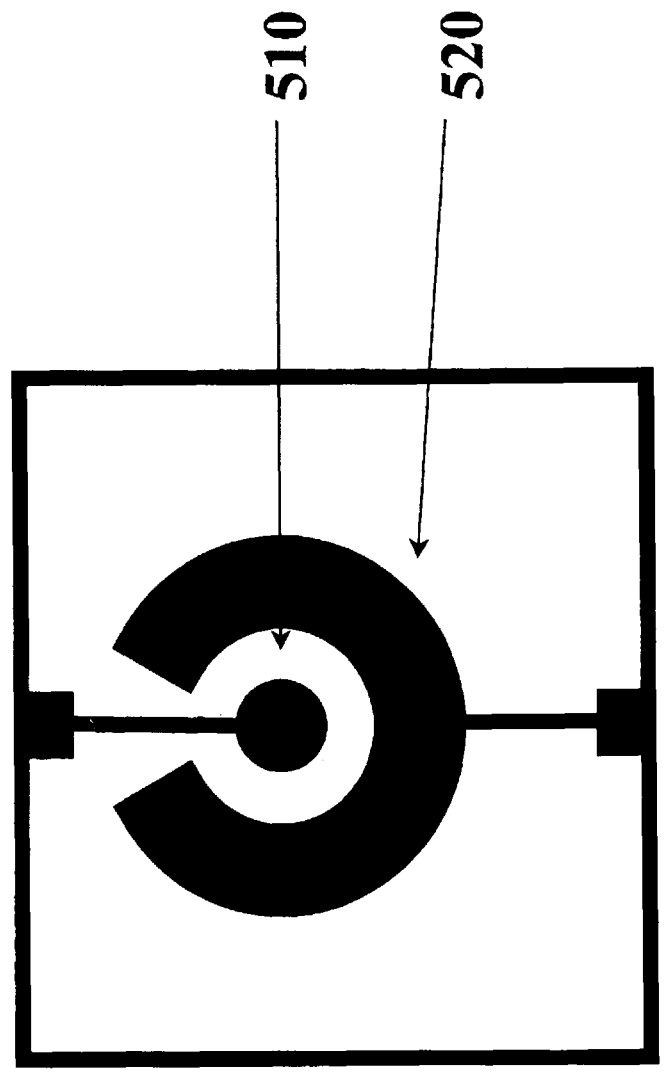
FIG. 5 is a schematic representation of a device with two electrodes of different areas 510 and 520.
Figure 6:
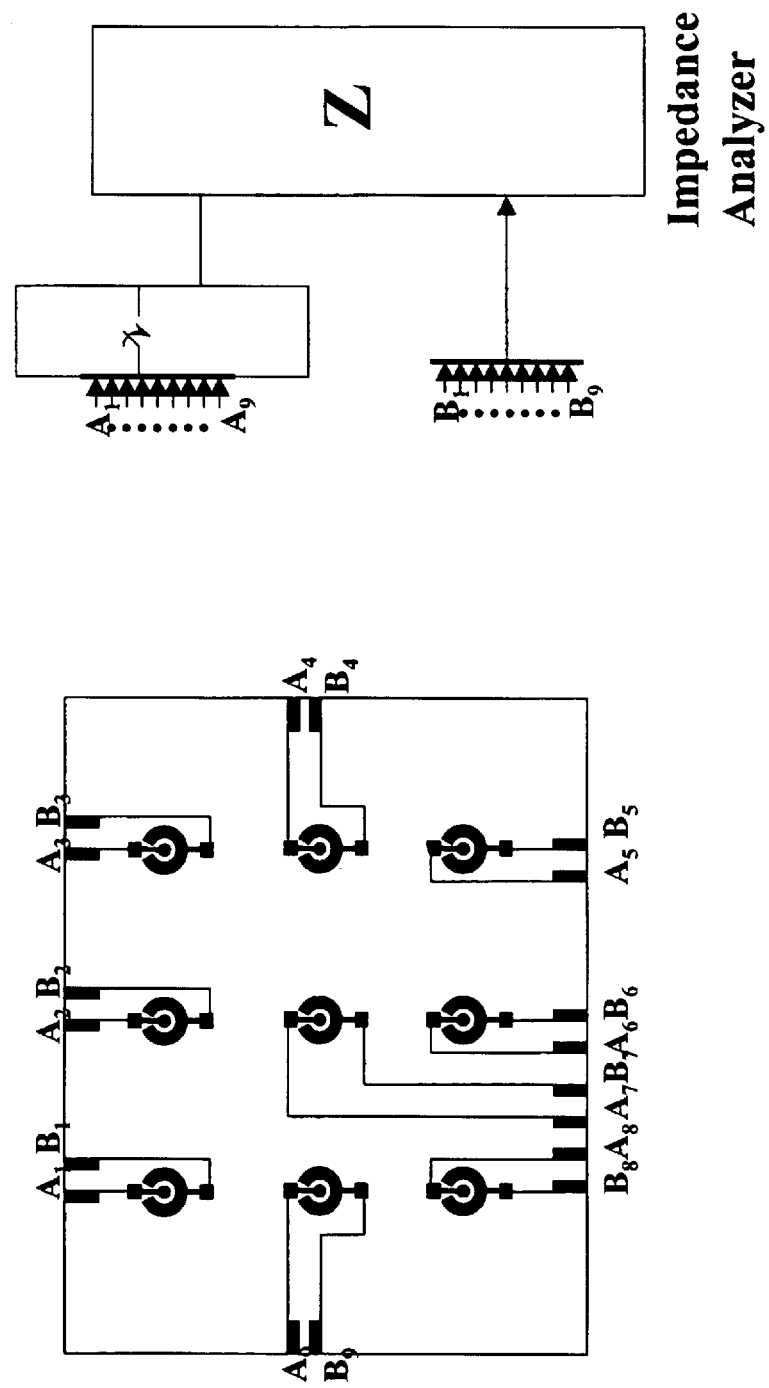
FIG. 6 is a schematic representation of a molecular assay plate with nine electrode structure units each having two electrodes. An impedance measurement analyzer is switched for the impedance measurement among the nine units.
Figure 12:
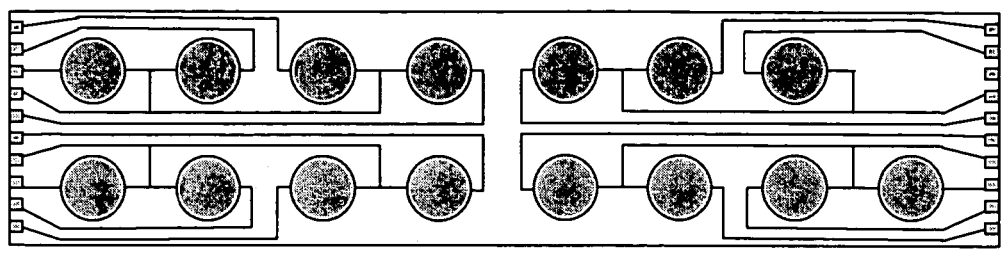
FIG. 12(A) shows a device having 15× electrode-structure units that were arranged in a 2-row by 8-column configuration on a substrate. The details of the electrode structures were not shown except for the two electrical connections (electrode traces) per electrode structure unit for connecting the electrode structures to connection pads located on the two ends of the substrate. One of the wells is a "null" well; that is, there is no active sensor associated with that well. The null well is utilized as a control well. Electrode structures may have various geometries such as those shown in FIGS. 1A, 1B, 1C, 5, 6, 7A-7F.
FIG. 12(B) shows a device having 16× electrode structure-units that were arranged on a substrate. The details of the electrode structures were not shown except for the two electrical connections (electrode traces) per electrode structure unit for connecting the electrode structures to connection pads located on the two ends of the substrate. Electrode structures may have various geometries such as those shown in FIGS. 1A, 1B, 1C, 5, 6, 7A-7F.
FIG. 12(C) shows a device having 16× electrode structure-units that were arranged on a substrate. Each electrode structure unit has an interdigitated electrode array.
Figure 12:
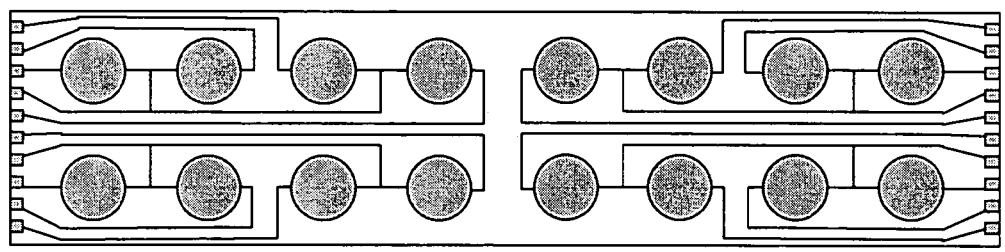
Figure 12:
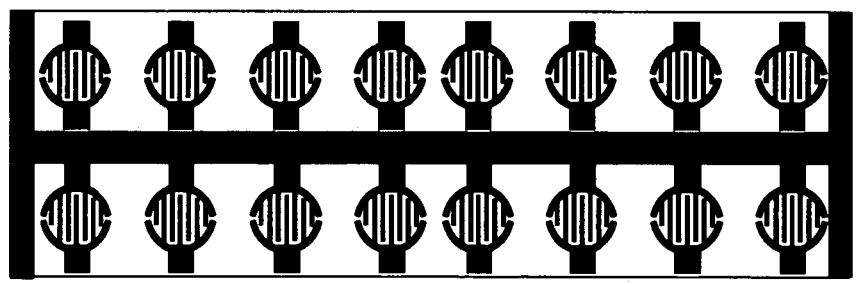

A preferred configuration for the device of the invention is one in which the connection pads are at opposing ends of the apparatus substrate. All traces extending from each electrode array at either end thereof form electrically conducting conduits to the connection pads without any intersection between any individual trace. FIGS. 4, 12A and 12B exemplifies the manner in which traces may be drawn from each electrode array to a connection pad.

In another exemplary embodiment, a fabrication or manufacturing method is used to produce holes at certain locations of the substrate. These holes are located at the positions where electronic connections to the electrode structures can be made. The holes can be gold-plated during the thin film deposition of the substrates. After the electrode structures are fabricated and patterned on the substrate and the holes on the substrates can be further filled with conductive pastes. After the electrode-containing substrate is attached and bonded to a multi-well plate, the electronic connection to an impedance measuring circuit or instrument can be achieved from the bottom side of the multi-well plate at the positions corresponding to conductive-paste-filled holes.

In another approach, bottom-less multi-well plates can be bound to the substrate that has a metal film layer, or microtiter or other plates having bottoms can be gold-deposited with a layer of metal on the bottom surfaces of the wells. Laser ablation may then be used to directly pattern electrode structures. The electronic connections to the electrode structures on these multi-well plates can use various connection methods described above.

In an example, a 16×-unit device can be constructed on a glass substrate using photolithography method. The final glass substrate dimension is 75 mm by 22 mm with gold thickness ~0.2 micron and Cr thickness ~0.03 micron. Different electrode geometry may be used with the 16×-unit device arranged in a 2 row by 8 column configuration. Electrode connection pads can be located along the longer edges of the substrate.

To construct a measurement device, a bottom-less 16× plastic well strip can be constructed with dimensions suitable for a 16× device. Each well is coned shaped so that the top diameter is about 6.5 mm whilst the bottom diameter is 5 mm. The 5 mm diameter at the bottom side ensures that sufficient spaces are left for the electronic connection pads, which can be connected to external impedance analyzers. The bottom side of the plastic well strip comprises a continuous channel which is connected to an opening port in the middle of 2 by 8 plastic wells. The bottom side of the plastic well strip is sufficiently flat with respect to the 16× glass slide device.

In order to bond the 16× plastic well strip to 16×-unit substrate, 16× well strip can be tightly secured over the 16×-unit substrate. A biocompatible, silicone based adhesive can be used to inject into the port in the plastic strip. The viscous adhesive can move through the channel on the bottom side of the plastic strip. After the adhesive is cured, the plastic strip is tightly bond to the 16× device. Another approach to bond the 16× plastic well strip to 16×-unit substrate is by using double-sided adhesives (for example, pressure sensitive adhesives). In this approach, the adhesive is processed or machined so that it has 16 holes that are located at corresponding positions to the 16 electrode units on the 16× substrate or to the 16 plastic wells on the 16× plastic well strip. The diameter of the 16 holes on the adhesives is same as, or similar to, the diameter of the wells on the plastic strip. In assembly, the supporting liners on one side of the adhesive is peeled off so that the adhesive is aligned to and bond to the plastic well strips with each hole on the adhesive corresponding to each well on the plastic strip. After that, the other side of the adhesive is also peeled off from the adhesive so that the 16× substrate can now be aligned and bond to the adhesive that is bonded to the plastic well strip.

In yet another aspect of the present invention, the present invention is directed to a method of making multi-well plates suitable for molecular assays based on electric impedance detection or for cell electroporation based on electrodes fabricated on substrates or for electric impedance-based monitoring of cell adhesion, cell growth or cell biological states. The method of the present invention comprises, (1) providing a non-conducting substrate, (2) depositing electric conductive films on said substrate, (3) patterning of electrically conductive films to make electrodes or electrode structures by using laser ablation of conductive film, (4) assembling the thin-film patterned substrates to bottomless multi-well plates to form electrode-containing multi-well plates. In a preferred embodiment of the methods of the present invention, the substrates are made of materials selected from glass, polymer, plastics, ceramics, fiber glass, or a combination of the above. The substrate can be cleaned by suitable procedures to be ready for deposition of electrical conductive thin films. Many laboratory procedure for cleaning glass, silicon wafer, plastic-ware can be used for cleaning of the substrate. In some cases, mechanical scrubbing of the substrate surfaces may be necessary to obtain clean-substrates.

In a preferred embodiment of the present methods, electric conductive films to be deposited on said substrates can be metal films, including gold, chromium, nickel, copper, platinum, aluminum, tungsten and others. It is possible to have two or more than two metal types being used as the thin conductive films. For example, chromium film can be used as an adhesion layer on glass or plastic substrate and gold or platinum film can be further deposited on the adhesion layer. Other electrical conductive films can also be used. For example, indium-tin-oxide can be used. In another example, electrically conductive polymer films can also be used. Electrically conductive films can be deposited by various methods such as thermal evaporation, electron-beam evaporation, sputtering, depending on the substrate materials and on the type of conductive films to be generated. Electrically conductive films can be different thickness, depending on conductivity of the electrical conductive film and on required conductance or resistance. The thickness of electrically conductive films can be as thin as less than 100 nanometer to as thick as over 1 micron.

In a preferred embodiment of the present methods, laser ablation masks will be used to pattern-generate required electrodes. Geometry of patterns on the laser ablation masks will be the same as the geometry of the electrodes or electrode structures to be made on the substrate. It is possible to have the geometry of patterns of the laser ablation masks being the same size as that of the electrodes or electrode structures to be generated. It is also possible to have the geometry of patterns of the laser ablation masks having larger sizes that that of the electrodes or electrode structures to be generated. For example, a 2×, or 3× mask, i.e., the patterns on the mask being twice or three times of that of the electrodes or electrode structures to be made, can be used. In using laser ablation mask for thin film patterning of the electrodes, the mask is placed between the thin film coated substrates on which the thin film patterning is taking place and laser source with appropriate optical paths.

The laser source will be a beam having a finite geometry (for example, 200 micron wide by 2 mm long) over which the intensity of the laser beam is relatively uniform. This laser beam scans over the mask and reaches the substrate through appropriate optical paths (for example, including lenses). The laser beam will ablate the thin conductive film at regions corresponding to the regions on the masks where the laser beam is transparent. The laser beam will be blocked at thin conductive film regions corresponding to the regions on the masks where the laser beam is not transparent or is blocked. While other lasers can be used for laser ablation of thin conductive films, UV excimer laser is particular suitable for patterning of thin metal films on either glass or polymer substrates. For example, excimer laser at 193 nm and 248 nm can be used.

Appropriate energy intensity is required for ablating thin conductive films. For example, an energy intensity of 0.5-1.5 J/cm$^2$ can be used to ablate thin gold films up to 0.2 micron thick on a glass substrate (with a 0.0075 micron-0.03 micron thick chromium seeding layer). Those who are skilled in laser ablation of thin films on substrates can readily determine appropriate laser wave length, energy intensity (fluence), laser pulse duration and laser pulse number needed for ablating off different thin films. Cited here are following articles or publications provides basic information for laser ablation of thin films on substrates: "Excimer laser ablation of thin gold films on a quartz crystal microbalance at various argon background pressures", by Zhang, X., S. S. Chu, J. R. Ho, C. P. Grigoropoulos, in *Appl. Phys. A: Material Science & Processing*, volume 64, pp 545-552, 1997; "Metal film removal and patterning using a XeCl laser", by Andrew J. E., Dyer P. E., Greenough R. D. and Key P. H., in *Appl. Phys. Letter*, Vol. 43 (11), pp 1076-1078, 1983; "Excimer laser processing of thin metallic films on dielectric substrates", by Sowada U., Kahlert H.-J., and Basting D., in *SPIE* (*High Power Lasers: Sources, Laser-Material Interactions, High Excitations, and Fast Dynamics*), vol. 801, pp 163-167, 1984.

The process parameters for laser ablation of thin gold/chromium film we were using are as follows: (1) a 3× mask, (2) laser energy intensity between 0.5 and 1 J/cm$^2$ and laser wavelength at 248 nm; (3) synchronized motion of the mask and the substrate with the substrate moving at speed up to 10 mm/sec. To ensure thorough removal of the gold film at electrode gaps, more than one laser ablations were used.

When laser ablation is used to pattern thin films of conductive materials on substrates for making electrodes or electrode structures of the devices of the present invention, because of large areas (for example, larger than 0.3 mm$^2$, 1 mm$^2$, even 5 mm$^2$, or even 20 mm$^2$) of electrodes (or electrode structures) of the devices of the present invention and because of relative fine electrode structures (for example, electrode elements having 100 micron width and 20 micron gap between them), the laser-ablated conductive materials may come back to the surfaces of the substrates and cause a re-deposition problem on the patterned substrate, affecting the quality of thin-film patterned substrates.

The quality issues here include how clean the surface of the substrates will be after processing, how reproducible the laser ablation process for patterning is, would there be re-deposits of ablated materials on the surface of conductive electrodes and would there be re-deposits of ablated materials on the surfaces at the gaps between the electrodes. The re-deposits would have to be cleaned or removed in order for the electrodes in the processed devices to perform properly in electric impedance measurements or to perform re-producibly from one device to another device.

An important aspect of the present invention includes how the "re-deposit problems" can be addressed. In one invented approach, a thin "sacrificial" film of material that can be readily removed by, for example, some solvents like water, or acetone is deposited or coated on the substrate prior to the laser ablation process. This sacrificial film preferably would have to be thin and uniform and can be readily removed by laser ablation process. The thickness of the sacrificial film may be any thickness. However, preferably, the sacrificial film thickness is less than 5 micron, or less than 1 micron, or less than 0.1 micron. The sacrificial films can be photoresist materials or deposits from a thick soap solution. So the laser ablation process is performed with this sacrificial film on the substrates. After laser patterning, the substrates will be subjected to a simple step to remove the sacrificial film by using some solvents. Use of sacrificial films would remove the re-deposition problems occurring on the patterned electrode surfaces. In another invented approach, after laser ablation of thin conductive films, the laser-processed substrates can be subjected to a thorough cleaning procedure to remove the re-deposits.

For example, the laser-processed substrates can be placed into cleaning solutions, for example, acid (as an example, 1 M HCl) and/or base (as an example 1M NaOH) solution, for a period of time (for example, 1 hour, 3 hours, 5 hours, 8 hours, 12 hours, or even 24 hours). The solution may be agitated when the laser processed substrates are placed inside. Agitation can be provided by ultrasonic waves or simply mechanical stirring bars. Some re-deposits can be removed by these processes. In another example of cleaning the laser processed substrates, the substrates can be cleaned by using mechanical scrubbing on their surfaces. Such scrubbing can be done with a cotton ball (or Q-tip, or a swab) soaked with water, or acid, or other solutions. In yet another example of cleaning the laser processed substrates, one could use the combination of the cleaning methods described in the above two examples of cleaning solutions and mechanical scrubbing (for example, with a Q-tip, or a swab).

In one exemplary embodiment, assembling the thin-film patterned substrates to bottomless multi-well plates to form electrode-containing multi-well plates can utilize double-sided pressure sensitive adhesives. In another embodiment, assembling the thin-film patterned substrates to bottomless multi-well plates can make use of liquid adhesives. Exemplary approaches of bonding the thin-film patterned substrates to bottomless multi-well plates by using liquid adhesive or double-sided pressure sensitive adhesives have been descried above.

In less preferred embodiments, other methods for forming electrodes on the substrates of the invention may be employed. For example, electrode elements, electrodes or electrode structures can be fabricated to the same side of the nonconductive substrate by any suitable methods, e.g., photolithography. Electrodes or electrode elements within an electrode array can be fabricated onto the substrate by suitable microfabrication or micromachining methods (see, for example, "Lithography", in *Fundamentals of Microfabrication*, 1997, Chapter 1, pp 1-50, edited by Marc Madou, CRC Press). One typical method is to use a photolithography method for making such electrodes. As a non-limiting example, a photolithography method to produce an electrode array on a solid substrate is as follows. The substrate may be any suitable material, e.g. glass. The process starts with a clean glass that is first deposited with a thin, adhesion layer of chromium or titanium (e.g. 10 nm) and followed by a deposition of 100-200 nm thick gold. The deposition may be achieved using a vacuum evaporation. Photoresist is then spin-coated on to the gold film to micron thickness and then exposed to UV light through a mask containing an image of a required electrode array. The exposed photoresist is developed using photoresist developer, and the gold and chrome layers are etched subsequently with $KI/I_2$ and $K_3Fe(CN)_6/NaOH$, respectively. Masks are produced commercially using electron-beam writing techniques on ultra-high resolution plates.

Other techniques can also be used for fabricating the electrodes on substrates. For example, an electrode pattern can be made using laser ablation. For laser ablation, one side of the substrate is first deposited with a thin layer metal film (for example, a gold film of about 0.2 µm over a seeding Cr layer of 25 nm) using methods such as vapor deposition and/or sputtering. The thin metal film is then exposed to a laser (e.g., an excimer laser at 248 nm) at appropriate intensity through a mask containing an image of required electrode array. At the regions where the mask is "transparent" to the laser, the laser hits on and interacts with the metal film and the metal film is ablated off from the substrate. Since the substrate (e.g. glass or plastics) reacts differently with the laser from the metal film, it is possible to choose appropriate laser condition (wave length, intensity, pulse width) so that the laser can ablate the metal film and has no effect or minimal effect on the substrate. At the regions where the mask is "blocking" the laser, the metal films remain on the substrate. Masks are produced commercially using electron-beam writing techniques on ultra-high resolution plates. Those who are skilled in laser ablation and thin film patterning with laser ablation can readily choose appropriate procedure and laser wave length, intensity, masks for producing electrodes on the polymer membranes.

There are other methods of microfabrication or micromachining that can be used for fabricating electrode or electrode elements on different substrates. For example, the methods such as screen-printing and the methods used for making printed circuits board (PCB) could also be used for making electrodes or electrode structures on various substrates. Those who are skilled in microfabrication and micromachining can readily choose appropriate fabrication methods according to required substrate material and electrode material, and required geometry resolution for electrodes or electrode elements.

Figure 11:
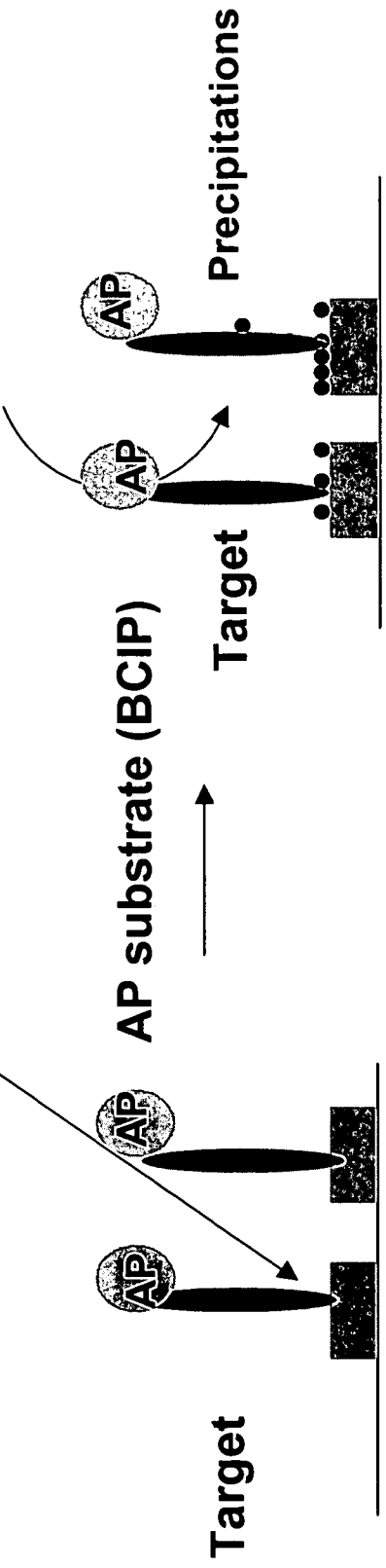
FIG. 11 illustrates a microelectrode strip (or electrode strip) for molecular detection. The microelectrode strip contains microelectrode structure units fabricated on a substrate strip. Non-limiting examples of the substrate materials include glass, plastic sheets or membrane, ceramics, polymer membranes, insulator-on-semiconductor (e.g., silicone-dioxide on silicone), fiber glass (like those for printed circuit board) or other insulating materials. A variety of microfabrication or micromachining methods can be used to fabricate or produce the microelectrode structure units on the substrate. On the surface of the microelectrode array, specific molecules are anchored or bound to or absorbed. The anchored molecule can be nucleic acid, peptides, protein and other molecules such as chemical compounds. The molecules can be anchored, bound, or absorbed onto the surface via different physical or chemical methods. Non-limiting examples of physical methods for coating may include passive absorption, spinning coating of molecule solution followed by drying, spotting of molecule solutions on designated electrode structure units. Non-limiting examples of chemical methods for surface modification may include molecular self assembly, chemical reactions on the surface. These physical or chemical methods are used to modify the electrode surfaces with anchoring chemical molecules. A single strip may have multiple electrode structure units. The surface of different electrode structure units may be modified or coated with different anchoring molecules so that each microelectrode structure unit is surface-modified with a unique type of molecules. The anchored, bound or absorbed or otherwise deposited molecules on the surface of microelectrode structure units serve as capturing molecules. Target molecules in a sample solution can bind to, or react with such capturing molecules. Upon binding of target molecules onto the capturing molecules, electric impedance between microelectrode structures within an electrode structure unit will be changed and such changes are measured or monitored by an impedance analyzer or impedance measuring circuits. In some cases, the target molecules are labeled with enzymes (for example, alkaline phosphatase, AP in FIG. 11). The label enzymes are then used for a catalytic reaction to convert enzyme substrates (for example. BCIP in FIG. 11) into products. The products are then be monitored by electric impedances between microelectrode structures. For example, the products may be insoluble and can precipitate onto the surface of the microelectrode structures. In other cases, the target molecules are labeled with certain "labeling" molecules. These labeling molecules may involve specific chemical reactions, which would result in products that can be monitored or measured by impedance detection across electrode structures. For example, the products may be insoluble and may precipitate onto the surfaces of electrode structures. The detection or measured of such products by electric impedance measurement can provide qualitative and quantitative information about target molecules in the sample solution.
Figure 18:
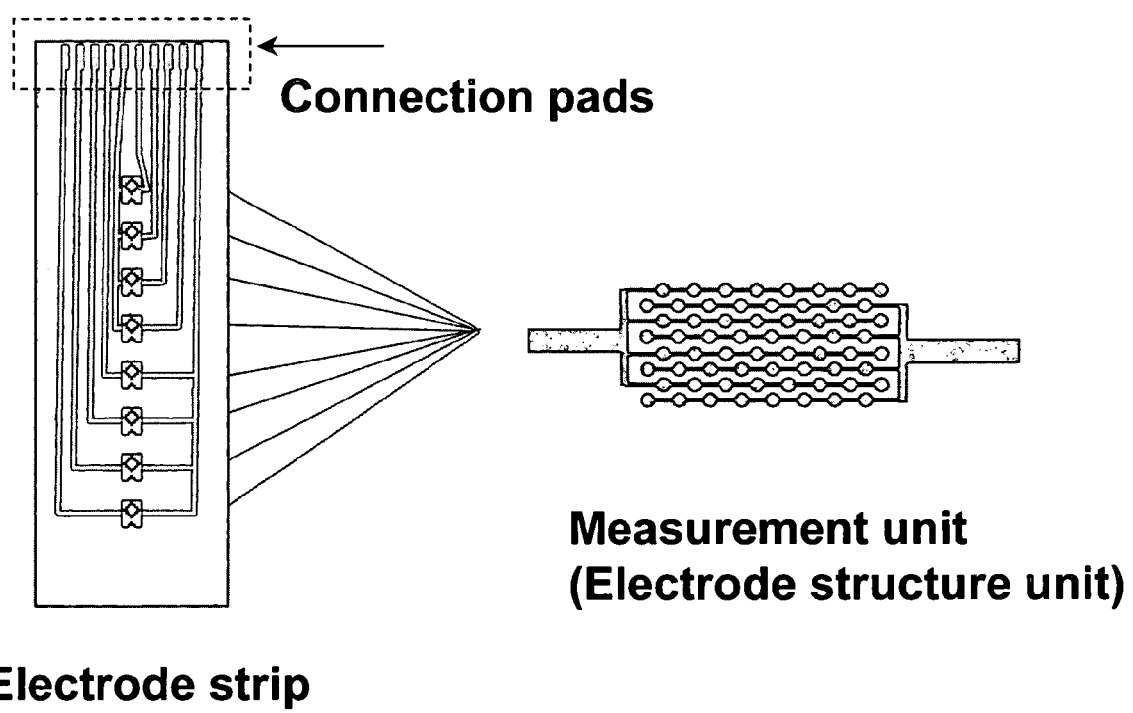
FIG. 18 shows an electrode strip based device for molecular assays.

In yet another exemplary embodiment of the device of the present invention, device takes the form of a microelectrode strip or electrode strip. Examples of such electrode strips or microelectrode strips are shown in FIGS. 11 and 18. In one embodiment of such electrode strips, a rectangular shaped, non-conducting substrate is used as the strip on which microelectrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. Alternatively, these dimensions can be described in terms of electrode width and electrode gaps. Thus, both electrode widths and electrode gaps can vary from as small as less than 5 micron, or less than 10 micron, to as large as over 200 micron, over 500 micron, over 1 mm.

The electrode strip (or microelectrode strip) can be of any geometry for the present invention. One exemplary geometry for the electrode strips is rectangular shape—having the width of the strip between less than 50 micron to over 10 mm, and having the length of the strip between less than 60 micron to over 15 mm. For example, an electrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm. In the example embodiment shown in FIG. 18, the electrode strip comprises 8 measurement units, each of which is a separate electrode structure unit that can be used for performing the measurement of molecular assay reaction. In this example, there are electrical connections coming out from each electrode structure units. It is between these two electrical connections that the impedance between the electrode structures within each electrode structure unit is measured. These two electrical connections are then connected to the connection pads located on the edges of the electrode strip. The external impedance analyzer or impedance measuring circuits are then used to connect these connection pads for the measurement of electrical impedance. Surfaces of electrode structure units may be coated or covered with capturing molecules, or anchoring molecules. Different capturing or anchoring molecules may be used for surfaces of different electrode structure units. In using such electrode strips, plastic housings having multiple openings may be used to bind to the electrode strips to form "electrode strip unit" or "electrode strip test unit" by using various binding methods including liquid adhesives, adhesive tapes (such as double-sided pressure sensitive adhesives). Each opening in the plastic housing is located at a position corresponding to a measurement unit (i.e. electrode structure unit) and serves as a measurement well for liquid samples. After binding the electrode strips to the plastic housings, sample solutions can be applied to each well for molecular assays. In another embodiment for using such electrode strips, each opening in plastic housing may enclose two or more measurement units.

There are other approaches for using the electrode strips. In one approach, porous materials, which allows liquid samples to move through, may be placed onto the electrode strips and then plastic housings are used to bind to the electrode strips and to enclose the porous materials. Plastic housings may have one or more openings. Each opening would enclose at least one measurement unit. Since porous materials allow liquid sample to move through, adding liquid sample into the porous materials would result in the introduction of sample to all regions of the electrode strip.

In yet another aspect of the present invention, the present invention is directed to a method of obtaining electrode strip unit (or electrode strip test unit) for molecular assays based on electric impedance detection or for cell electroporation based on electrodes or electrode structures fabricated on the strips or for electric impedance-based monitoring of cell adhesion, cell growth or cell biological states. The method of the present invention comprises, (1) providing a non-conducting substrate, (2) depositing electric conductive films on said substrate, (3) patterning of electrically conductive films to make electrodes or electrode structures by using laser ablation of conductive film to obtain thin-film patterned substrate, (4) optionally, cutting thin-film patterned substrates into electrode strips of certain geometry, or alternatively, said thin-film patterned substrate is used as an electrode strip, (5) assembling said electrode strip to a plastic housing that contains at least one opening to form an electrode strip unit, wherein said at least one opening is aligned with electrodes or electrode structures on the electrode strip. In a preferred embodiment of the methods of the present invention, the substrates are made of materials selected from polymer, plastics, glass, ceramics, fiber glass, or a combination of the above. The substrate can be cleaned by suitable procedures to be ready for deposition of electrical conductive thin films. Many laboratory procedure for cleaning glass, silicon wafer, plastic-ware can be used for cleaning of the substrate. In some cases, mechanical scrubbing of the substrate surfaces may be necessary to obtain clean-substrates.

In a preferred embodiment of the present methods, electric conductive films to be deposited on said substrates for making electrode strips are the same as or similar to those films suitable for making multi-well plates described above. Similarly, laser ablation method is the preferred approach for thin film patterning to fabricate required microelectrodes.

Thin-film patterned substrates may be cut into strips or electrode strips with appropriate or required geometry and dimension. For example, a thin-film patterned substrate may be a rectangular shape of 20 mm by 30 mm. With electrodes or electrode structures properly arranged on the substrate after thin-film patterning, the substrate can be cut into 15 electrode strips, each of which having 2 mm by 20 mm dimension and having appropriate electrodes or electrode structures that can be used.

In one exemplary embodiment, assembling an electrode strip to a plastic housing to form an electrode strip unit or electrode strip test unit can utilize double-sided pressure sensitive adhesives. In another embodiment, assembling an electrode strip to a plastic housing to form an electrode strip unit or electrode strip test unit can make use of liquid adhesives. Exemplary approaches of bonding the thin-film patterned substrates to bottomless multi-well plates by using liquid adhesive or double-sided pressure sensitive adhesives have been descried above.

In preferred embodiments of system of the present invention, the electrodes comprised in a device, apparatus or the system connect to an impedance analyzer or impedance measuring circuit at least two connection pads. Electrodes can directly or indirectly connect to a connection pad, where they connect to lines from impedance measuring circuit or impedance analyzer. A connection pad is preferably at the edge or perimeter of a device or apparatus of the present invention, but this is not a requirement of the present invention. The connection between electrodes and a connection pad can optionally be via a connecting path that can be localized to the edge of the device. In most uses of a device of the present invention, a device will be part of an apparatus and attached to, or within a plate or a fluid container that can contain solution samples. In these embodiments a connection pad can be situated on a fluid container or plate comprising one or more fluid containers, preferably near or at the edge or perimeter of a device.

In preferred embodiments of the present invention, a system that comprises a device of the present invention also includes interface electronics, including impedance measurement circuit and switches (e.g. electronic switches), to control and switch the impedance measurement circuits to different electrode structure units of the apparatuses of the present invention. Preferably, a system of the present invention also includes a computer having software programs that can enable real-time measurement or monitoring of impedance between the electrodes or electrode structures of the apparatuses of the present invention. The measured impedance data can be automatically analyzed and processed to derive appropriate parameters (e.g. molecular reaction index, or cell number index) and displayed on a monitor.

Preferably, the software program has one or more of the following functions: (1) electronically switching for connecting impedance measuring circuit (or analyzer) to one of multiple electrode units (electrode structure units) of the present apparatuses; (2) controlling impedance measurement circuit (or analyzer) for measurement of impedance between or among electrodes or electrode structures at one or multiple frequencies; (3) processing the acquired impedance data to derive appropriate biologically relevant parameters (e.g., molecular reaction index, or cell number index); (4) displaying the results on a monitor or storing results; (5) automatically performing above functions 1 through 4 at regular or irregular time intervals.

Methods for Using the Devices of the Invention

The present device and multi-well microplate can be used to measure impedance at a physiological ion concentration or at a non-physiological ion concentration. Further, the device and multi-well microplate can be used for electroporation of cells suspended in the wells or attached to the surfaces of the wells containing electrodes or electrode structures. Electroporation protocols with appropriate voltage amplitude, waveform, time duration, number of pulses can be used so that voltage pluses are applied to the electrodes or electrode structure units to generate electric field sufficient strong to electroporate the membrane of cells. While the present devices or microplates can be used for electroporating both suspension cells and adherent cells, the present devices or microplates are particular suited for electroporating adherent cells.

The methods for electroporating adherent cells using the present device or multi-well microplates comprise the following, (1) providing an above-described multi-well microplate, at least one well of which microplate contains electrodes or electrode structure units on the bottom surface, (2) attaching or growing cells in the electrodes-containing wells, (3) applying electrical voltages pulses to the electrodes to result in electroporation of the membrane of the cells adhered to the bottom surface of the wells. The methods for electroporating suspension cells using the present device or multi-well microplates comprise the following, (1) providing an above-described multi-well microplate, at least one well of which microplate contains electrodes or electrode structure units on the bottom surface, (2) adding the cells in the electrodes-containing wells, (3) applying electrical voltages pulses to the electrodes to result in electroporation of the membrane of the cells in the wells. Electroporation conditions with appropriate voltage amplitude, waveform, time duration and number of pulses can be determined with experiments for a good electroporation efficiency and a number of articles and publication also provides general guideline and possible specific conditions for electroporations. Some of these publications are cited here, including, "Cell electropermeabilization: a new tool for biochemical and pharmalogical studies", by Orlowski, S. and M. Lluis, in *Biochim. Biophys. Acta*, Vol: 1154, pp 51-63, 1993; "Electroporation of cell membranes", by Tsong, T. Y., *Biophys. J.* Volume 60: pp 297-306, 1990; "Electroporation of adherent cells in situ.", by Raptis, L. and K. L. Firth in *DNA Cell Biology*, Vol. 9, pp 615-621, 1990; "Electroporation of adherent cells in situ for the introduction of nonpermeant molecules", by Raptis L H, Firth K L, Brownell H L, Todd A, Simon W C, Bennett B M, MacKenzie L W, Zannis-Hadjopoulos M., in Methods Molecular Biology, Vol. 48, pp 93-113, 1995; "Recovery of Adherent cells after in situ electroporation monitored electrically", by Wegner J., Keese C. R., Giaver I., in Bio Techniques, Vol. 33, pp 348-357, 2002.

In yet another aspect, the present invention is directed to a method for monitoring target molecules, which method comprises: a) providing an above-described devices or multi-well microplate for monitoring molecular reactions; b) adding sample solution comprising target molecules or suspected of comprising target molecules to said device; c) incubating sample in the device to allow the capture of target molecules to capture molecules; and d) monitoring a change of impedance between or among the electrodes to monitor the presence or quantity of target molecules in a solution.

In yet another aspect, the present invention is directed to a method for assaying molecules in a sample solution, which method comprises: a) providing a device comprising: 1) a non-conducting substrate, 2) at least two electrodes fabricated to the same side of the substrate, 3) at least two connection pads on said substrate, wherein said at least two electrodes are connected respectively to said at least two connection pads; b) adding sample solution comprising target molecules to said device; c) incubating the sample solution in the device to allow target molecules to be bound to the electrode surfaces; d) adding reporting molecules in a solution to the device; e) incubating the solution in step d) in the device to allow the reporting molecules to bind to the target molecules; f) monitoring a change of impedance between or among the electrodes to monitor the presence or quantity of target molecules in a solution.

The present methods can be used to monitor any suitable parameters that are related to molecular reactions occurring on the electrode surfaces. For example, the present methods can further comprise determining the amount or number of target molecules that are present in a sample solution.

In yet another aspect, the present invention is directed to a method for monitoring cell attachment or growth, which method comprises: a) providing an above-described apparatus or multi-well microplate for monitoring cell-substrate impedance; b) attaching or growing cells to or on the surface of said apparatus or in a well of said multi-well microplate; and c) monitoring impedance between or among the electrodes or electrode arrays to monitor said cell attachment or growth on said apparatus or multi-well microplate.

The present methods can be used to monitor any suitable parameters that are related to cell attachment or growth. For example, the present methods can further comprise determining the amount or number of cells that are attached to or grown on the apparatus or multi-well microplate from the monitored impedance.

The present methods can be used to determine whether a test compound can modulate, i.e., increase or decrease, cell attachment or growth, or to screen for such a modulator. For example, the present methods can be conducted wherein the cell attachment or growth is monitored in the presence and absence of a test compound and the method is used to determine whether said test compound modulates attachment or growth of the cells. Generally, if a presence of a test compound results in increased cell attachment or growth, such a compound is considered as a cell attachment or growth stimulator. Conversely, if a presence of a test compound results in decreased cell attachment or growth, such a compound is considered as a cell attachment or growth inhibitor.

The present methods can be used to monitor viable cell attachment or growth. For example, the present methods can be conducted wherein only viable cells can attach to or grow on the surface of the apparatus or in a well of the multi-well microplate of the present invention, and the method is used to monitor the cell attachment or growth of viable or detachment of non-viable cells. The present methods can further comprise determining the amount or number of viable or non-viable cells. The present methods can also be conducted wherein the cell attachment or growth is monitored in the presence and absence of a test compound and the method is used to determine whether said test compound modulates viability of the cells. In another example, the present methods can be conducted wherein the cell attachment or growth is stimulated by a growth factor and the method is used to screen the test compound for a growth factor antagonist.

Conditions that affect such cell attachment and growth can be monitored and analyzed by the impedance measurement. Generally, for adherent cells, viable cells attach or adhere to the substrate. As cells die off, they start to lose adherence to the substrate and the detachment can then be monitored by cell-substrate impedance. For example, the present invention can be used for cytotoxicity assays and for monitoring and determining cell physiological and health statues. Chemical compounds having toxic effects on the cells or suspected of having toxic effects on the cells can be added into the culture chamber/well in which cells are present. The chemical compounds may lead to cell death via different mechanisms such as apoptosis and necrosis. As cells die off from their initial viable states, the cell attachment condition changes. Typically, they would be losing attachment to the surface. Such loss of attachment can be readily monitored by the impedance change of the present invention. Thus, cytotoxic process can be monitored in real time by the present invention.

In another example, the present assay can be used for monitor cell proliferation. As cells proceed to division, more and more cells grow on the electrode surfaces. This will lead to a larger impedance change or alteration in respect to electrode impedance baseline when no cells are present or no cells are attached to the electrode surfaces.

The present methods can be used to monitor attachment or growth of any suitable cells. Exemplary cells include animal cells, plant cells, fungal cells, bacterial cells, recombinant cells and cultured cells.

In yet another aspect, the present invention is directed to a method for monitoring cell attachment or growth, which method comprises: a) providing an above-described multi-well microplate; b) attaching or growing cells in a well of said multi-well microplate wherein each well contains substantially same number of same type of cells and serially different concentration of a test compound; and c) monitoring impedance between or among the electrodes or electrode arrays as a function of time to monitor the effect of said test compound on cell attachment or growth.

In one embodiment, the present method can further comprise determining the number of viable cells in each well. In another embodiment, the present method can further comprise determining whether the test compound is an antagonist to the growth of the cells. In still another embodiment, the present method can further comprise determining the dose-response curve of the test compound.

The present apparatuses, microplates and methods can be used to monitor cell, tissue, or organ biological, physiological and pathological processes such as cell growth, cell death, toxicity and cell division, etc.

The important considerations for a cell toxicity, cell death, and cell survival assay include determination as to how many cells died and how many cells are still viable. Current methods for cell toxicity, cell death, and cell survival assay include: 1) measuring concentration of intracellular ATP concentration to determine cell viability (fluorescence based detection system); 2) MTT assay, measuring intracellular enzymatic activity to determine cell viability (color metric measurement); and 3) apoptotic cell specific staining, e.g., TUNEL assay; dead cells are determined by fluorescence stained cells. All the current or conventional methods for cell toxicity, cell death, and cell survival assay have limitations in which they are labor intensive, require the use of expensive chemical reagents, and is a end-point assay that does not provide kinetic information.

For a cell survival assay, growth factors are essential for cell survival. Accordingly, treatment with a growth factor antagonists results in cell death by interfering with the growth factor signal transduction pathways. The following illustrates a procedure for cell plating and growth: 1) plating $1 \times 10^6$ cells in 3 T75 tissue culture flasks with 12 ml of EGM media (growth media) per flask; 2) allowing the cells to attach overnight and changing the growth media; and 3) changing the growth media once again after 3 days and allowing cell growth for another two days.

The following illustrates a procedure for cell survival assay: 1) trypsinizing cells in T75 flasks and seed $1 \times 10^4$ cells per well in 96 well plates in 100 ul of volume and cultivating the cells in the growth medium for overnight; 2) removing growth media and replacing with growth factor free media to starve the cells for 24 hours; 3) adding serial diluted growth factor antagonists to each well and incubating the culture for 1 hour; and 4) adding a corresponding growth factor or factors to each well and continuing to cultivating the cells for 3 days.

The following illustrates a procedure for MTT assay: 1) after 72 hours (three days), adding 15 ul of MTT dye solution to each well; 2) incubating for 4.5 hours at 37° C. in 95% air/5% $CO_2$ incubator; 3) adding 100 ul of stop solution and incubating the plates overnight at 37° C. 95% air, 5% $CO_2$ incubator; and 4) reading the plates at 570/630 nm on the ELISA plate reader. The data from the plate reader are analyzed using an Excel-based statistical data analyzing template and the dose-response curves or even $IC_{50}$ (50% inhibitory concentration) values are generated.

The present apparatuses, microplates and methods, in combination with the above-described procedures, can be used to measure total number of cells by measuring the electrode impedance change. A correlation can be established between the change in the impedance and the cell number on the electrodes. Such a correlation may be linear or may be non-linear. The advantages of the present apparatuses, microplates and methods over conventional methods for cell toxicity, cell death, and cell survival assay are: (1) the assays performed using the present invention to monitor cell conditions can be fully automated after cells are seeded into the wells and/or after the chemical compounds have been added to the wells); (2) the assays performed using the present invention to monitor cell conditions do not need reagents for detecting cell condition; (3) the assays performed using the present invention to monitor cell conditions can provide kinetic information.

The following example illustrates a cell survival assay using the present apparatuses, microplates and methods: 1) providing an microplate of the present invention for monitoring cell-substrate impedance where the electrode surface has been coated with specific adhesion-promotion molecules: 2) trypsinizing cells in T75 flasks; 3) seeding cells into the wells of the microplate according to surface density comparable to $1 \times 10^4$ cells per well in 96 well plates in 100 ul of volume, and cultivating the cells in the growth medium for overnight; 4) removing growth media and replacing with growth factor free media to starve the cells for 24 hours; 5) adding serial diluted growth factor antagonists to each well in the microplate and incubating the culture for 1 hour; 6) adding a corresponding growth factor or factors to each well of the microplate; 7) continuing to cultivating the cells for 3 days and monitoring change in impedance between (or among) electrodes or electrode arrays in each well with time over 3-days period; and 8) analyzing the impedance change and derive cell-number or cell-number index from the impedance change.

The present apparatuses or multi-well microplates can be used independently in the present methods. Alternatively, the present apparatuses or multi-well microplates can be used as a part of a larger device or system.

The present methods can be conducted manually. The present methods can also be conducted in a high-throughput mode. In one example, the present method can be automated. In another example, the present methods can be conducted wherein the molecular reactions are monitored.

Figure 19:
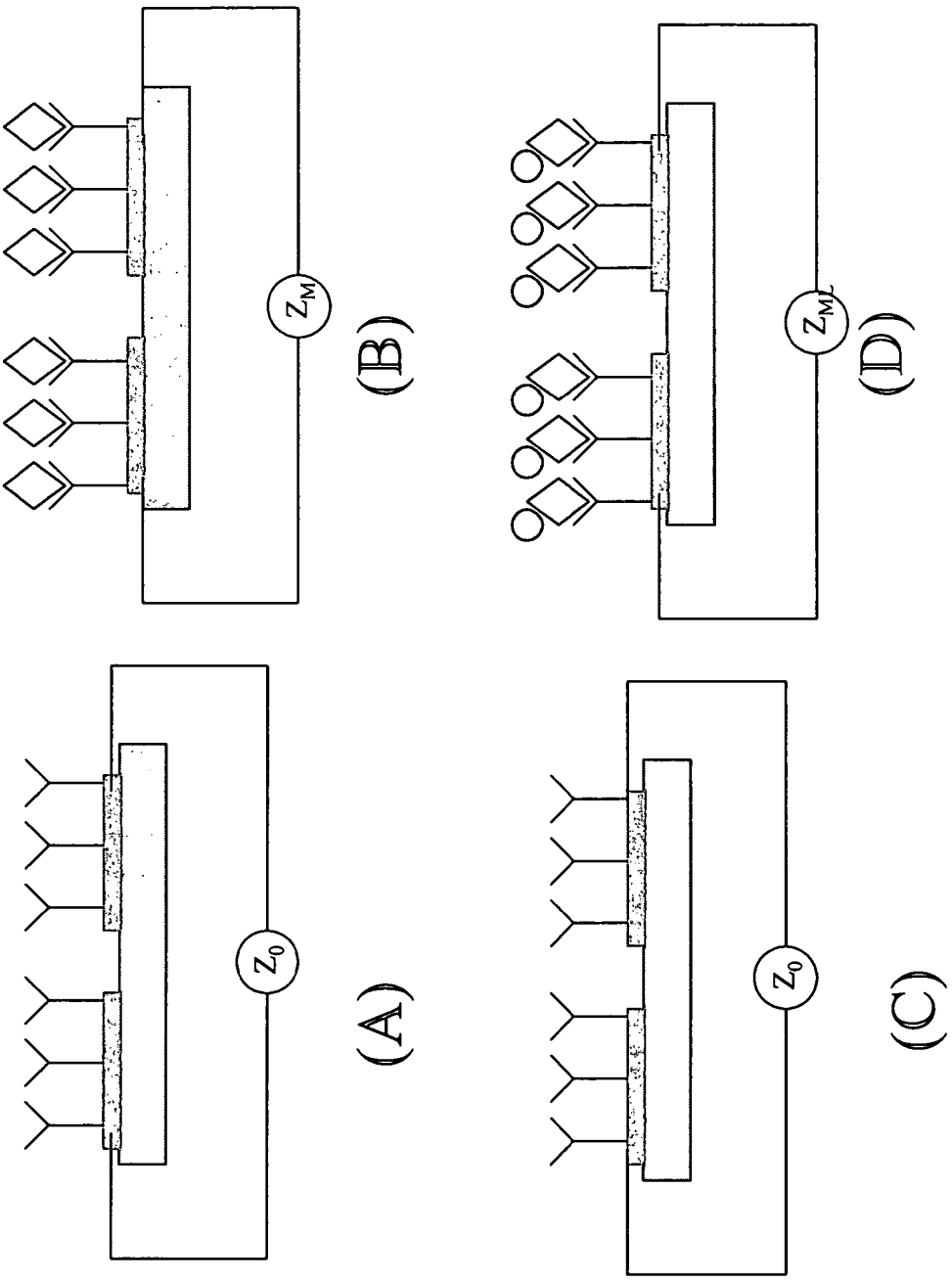
FIG. 19 illustrates operational principles of the monitoring of molecular reaction of bindings based on impedance measurement.
Figure 19:
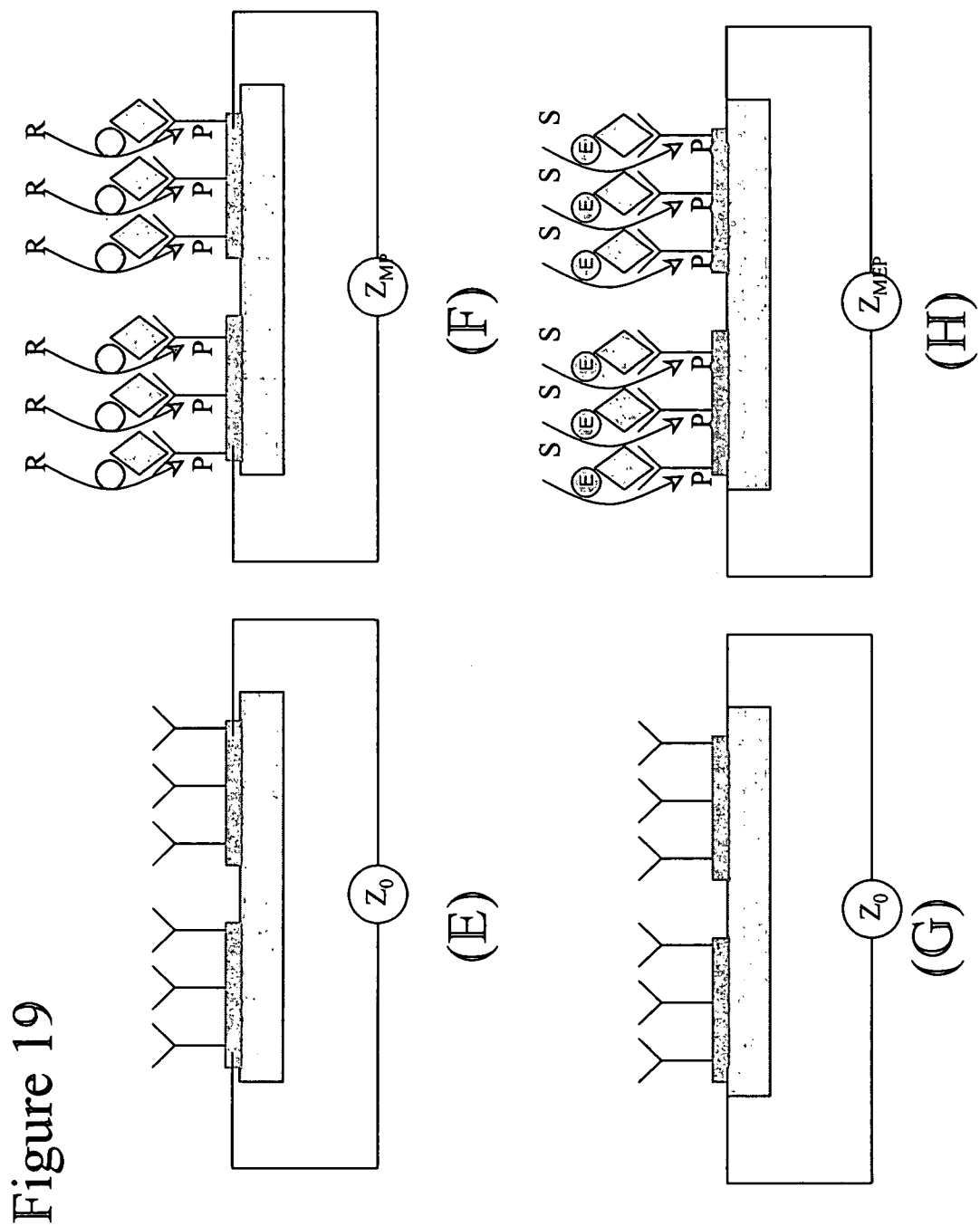

FIG. 19 illustrates operational principles of the monitoring of molecular reaction of bindings based on impedance measurement.

FIGS. 19(A, C, E and G) are cross-sectional drawing of a device of the present invention showing two electrodes. Capturing molecules, depicted with "Y" symbols, are anchored, placed, introduced, or bound to surface of the electrodes. Capturing molecules may be any molecules that may interact with target molecules to be measured or monitored in a sample solution. Capturing molecules may be antibodies, peptides, ligands, receptors, proteins, nucleic acids, nucleotides, oligonucleotides, or any molecules that can interact with or bind to target molecules. As an example, antibodies against DNA/RNA hybrid molecules are used as capturing molecules. Such antibodies may be directed absorbed onto the electrode surfaces. Alternatively, such antibodies may be labeled with biotin-molecules so that biotin-modified antibodies can be immobilized on the avidin-modified electrode surfaces through avidin-biotin binding. As an example, straptoavidin molecules are used as capturing molecules. In this case, target molecules to be monitored or assayed may be labeled with biotin molecules so that biotin-labeled target molecules can bind to capturing molecules—straptoavidin molecules—on the electrode surfaces through biotin-avidin interaction.

Illustrated in FIG. 19(A) is a measurement of background impedance $Z_0$ as measured for the electrodes coated with or covered with or modified with capturing molecules. Capturing molecules can be anchored to placed to, absorbed to, or bound to the surface of the electrodes by any suitable physical or chemical methods. Non-limiting examples of physical methods for coating may include passive absorption, spinning coating of molecule solution followed by drying, spotting of molecule solutions on designated electrode structure units. Non-limiting examples of chemical methods for surface modification may include molecular self assembly, chemical reactions on the surface. These physical or chemical methods are used to modify the electrode surfaces with anchoring chemical molecules.

FIG. 19(B) is Cross-sectional drawing of a device of the present invention showing two electrodes with capturing molecules, depicted with "Y" symbols, on the surfaces of the electrodes and with target molecules, depicted with "♦" symbols and binding to the capture molecules. Capturing molecules and target molecules form a molecular interaction or molecular binding pairs so that target molecules can bind to the capturing molecules. Target molecules may be any molecules that may interact with capturing molecules. Target molecules in a sample solution or suspected to be in a sample solution are molecules of interest to be measured or monitored. Like capturing molecules, target molecules may be antibodies, antigens, peptides, ligands, receptors, proteins, nucleic acids, nucleotides, oligonucleotides, or any molecules that can interact with or bind to capturing molecules. Illustrated in FIG. 19(B) is a measurement of impedance $Z_M$ as measured for the electrodes modified with capturing molecules to which target molecules bind. FIGS. 19(A) and 19(B) are a pair and show that the impedance between electrodes will be changed from $Z_0$ to $Z_M$, corresponding to a condition that electrodes are modified with capturing molecules (FIG. 19A) and to a condition that target molecules bind to the capturing molecules (FIG. 19B).

FIG. 19(D) is a cross-sectional drawing of a device of the present invention showing two electrodes with capturing molecules, depicted with "Y" symbols, on the surfaces of the electrodes and with target molecules, depicted with "♦" symbols and binding to the capture molecules. Different from FIG. 19(B), target molecules here are labeled with labeling molecules or labeling particles, depicted with "●" symbols. Capturing molecules and target molecules form a molecular interaction or molecular binding pairs so that target molecules can bind to the capturing molecules. Labeling molecules or particles are the molecules or particles that would increase the impedance change of ($Z_{ML}-Z_0$) in another word, to amplify the detection signal. Target molecules may be any molecules that may interact with capturing molecules. Target molecules in a sample solution or suspected to be in a sample solution are molecules of interest to be measured or monitored. Like capturing molecules, target molecules may be antibodies, antigens, peptides, ligands, receptors, proteins, nucleic acids, nucleotides, oligonucleotides, or any molecules that can interact with or bind to capturing molecules. Illustrated in FIG. 19(D) is a measurement of impedance $Z_{ML}$ as measured for the electrodes modified with capturing molecules to which target molecules bind, wherein target molecules are labeled with labeling molecules or particles. FIGS. 19(C) and 19(D) are a pair and show that the impedance between electrodes will be changed from $Z_0$ to $Z_{ML}$, corresponding to a condition that electrodes are modified with capturing molecules (FIG. 19C) and to a condition that target molecules bind to the capturing molecules (FIG. 19D). Labeling molecules or particles in FIG. 19(D) are used to amplify or further increase the impedance change of ($Z_{ML}-Z_0$). One non-limiting example of the labeling molecules may be certain large organic molecules whose presence on the electrode will affect the passage of the ions or electrons at the electrode surfaces and will result in a large change in impedance as measured between electrodes. One example of labeling particles may be nano-sized, electrically non-conducing, or semiconducting, or even conducing particles. The presence of such nano-sized particles will affect the passage of the ions or electrons at the electrode surfaces and will result in a large change in impedance as measured between electrodes. Here, the labeling molecules or particles may be attached to target molecules directly via covalent-bonding (or any other types of bonding) or indirectly via a recognition molecule couple such as biotin-avidin, sugar-lecithin, antibody-antigen and receptor-ligand.

FIG. 19(F) is a cross-sectional drawing of a device of the present invention showing two electrodes with capturing molecules, depicted with "Y" symbols, on the surfaces of the electrodes and with target molecules depicted with "♦" symbols and binding to the capture molecules. Different from FIG. 19(B), target molecules here are labeled with labeling molecules or labeling particles, depicted with "●" symbols. Capturing molecules and target molecules form a molecular interaction or molecular binding pairs so that target molecules can bind to the capturing molecules. Labeling molecules or particles are the molecules or particles that would increase the impedance change of ($Z_{ML}-Z_0$), in another word, to amplify detection signal. In this case, the signal amplification of the labeling molecules or particles is achieved through certain reaction between labeling molecules or particles with some reaction (R) molecules in solution. The reaction product (P) is deposited or precipitated on the electrode surfaces, resulting the impedance $Z_{MP}$ between electrodes. Target molecules may be any molecules that may interact with capturing molecules. Target molecules in a sample solution or suspected to be in a sample solution are molecules of interest to be measured or monitored. Like capturing molecules, target molecules may be antibodies, antigens, peptides, ligands, receptors, proteins, nucleic acids, nucleotides, oligonucleotides, or any molecules that can interact with or bind to capturing molecules. Illustrated in FIG. 19(F) is a measurement of impedance $Z_{MP}$ as measured for the electrodes modified with capturing molecules to which target molecules bind, wherein target molecules are labeled with labeling molecules or particles. FIGS. 19(E) and 19(F) are a pair and show that the impedance between electrodes will be changed from $Z_0$ to $Z_{MP}$, corresponding to a condition that electrodes are modified with capturing molecules (FIG. 19(E)) and to a condition that target molecules bind to the capturing molecules (FIG. 19(F)). Labeling molecules or particles in FIG. 19(F) are used to amplify or further increase the impedance change of ($Z_{MP}-Z_0$). The signal amplification of the labeling molecules or particles in FIG. 19(F) is achieved through certain reaction between labeling molecules or particles with some reaction (R) molecules in solution. The reaction product (P) is deposited or precipitated on the electrode surfaces and will affect the passage of electrons and/or ions at the electrode surfaces, leading to a large impedance change. Here, the labeling molecules or particles may be attached to target molecules directly via covalent-bonding (or any other types of bonding) or indirectly via a recognition molecule couple such as biotin-avidin, sugar-lecithin, antibody-antigen and receptor-ligand. The condition show in FIG. 19(F) can be regarded as a particular example of FIG. 19(D).

FIG. 19(H) is a cross-sectional drawing of a device of the present invention showing two electrodes with capturing molecules, depicted with "Y" symbols, on the surfaces of the electrodes and with target molecules, depicted with "♦" symbols and binding to the capture molecules. Different from FIG. 19(B), target molecules here are labeled with labeling molecules, depicted with "●" symbols. Capturing molecules and target molecules form a molecular interaction or molecular binding pairs so that target molecules can bind to the capturing molecules. Labeling molecules are the molecules that would increase the impedance change of ($Z_{MEP}-Z_0$) in another word, to amplify detection signal. In this case the labeling molecules are enzymes and signal amplification of the labeling molecules is achieved through enzyme-mediated or catalyzed reactions of substrate molecules (S) in a solution. The product (P) of the enzyme-mediated reaction is deposited or precipitated on the electrode surfaces resulting impedance ($Z_{MEP}$) of the electrodes is measured. Target molecules may be any molecules that may interact with capturing molecules. Target molecules in a sample solution or suspected to be in a sample solution are molecules of interest to be measured or monitored. Like capturing molecules, target molecules may be antibodies, antigens, peptides, ligands, receptors, proteins, nucleic acids, nucleotides, oligonucleotides, or any molecules that can interact with or bind to capturing molecules. Illustrated in FIG. 19(H) is a measurement of impedance $Z_{MEP}$ as measured for the electrodes modified with capturing molecules to which target molecules bind, wherein target molecules are labeled with labeling molecules or particles. FIGS. 19(G) and 19(H) are a pair and show that the impedance between electrodes will be changed from $Z_0$ to $Z_{MEP}$, corresponding to a condition that electrodes are modified with capturing molecules (FIG. 19G) and to a condition that target molecules bind to the capturing molecules (FIG. 19H). Labeling molecules in FIG. 19(G) are used to amplify or further increase the impedance change of ($Z_{MEP}-Z_0$). In this case, the labeling molecules are enzymes and signal amplification of the labeling molecules is achieved through enzyme-mediated or catalyzed reactions of substrate molecules (S) in a solution. The product (P) of the enzyme-mediated reaction is deposited or precipitated on the electrode surfaces, resulting impedance ($Z_{MEP}$) of the electrodes is measured. The reaction product (P) is deposited or precipitated on the electrode surfaces and will affect the passage of electrons and/or ions at the electrode surfaces, leading to a large impedance change. Here, the labeling molecules or particles may be attached to target molecules directly via covalent-bonding (or any other types of bonding) or indirectly via a recognition molecule couple such as biotin-avidin, sugar-lecithin, antibody-antigen and receptor-ligand. The condition show in FIG. 19(H) can be regarded as a particular example of FIG. 19(F). Some examples of such enzyme-based signal amplification are described in FIG. 8.

Examples of Calculation Methods and Applications

I. Impedance Frequency Spectrum for Molecular Assays

As mentioned earlier, the impedance (Z) has two components, namely the resistance Rs and reactance Xs. Mathematically, the impedance Z is expressed as follows, $$Z=Rs+jXs,$$

where $j=\sqrt{-1}$, depicting that for the (serial) reactance component Xs, the voltage applied over it is 90 degree phased-out from the current going through it. For the (serial) resistance, the voltage applied over it is in phase with the current going through it. As it is well-known in electronic and electrical engineering, the impedance can also be expressed in terms of parallel resistance Rp and parallel reactance Xp, as follows, $$Z=Rp*(jXp)/(Rp+jXp).$$

where $j=\sqrt{-1}$. Nevertheless, these expressions (serial resistance and serial reactance, or parallel resistance and parallel reactance) are equivalent. Those who are skilled in electrical and electronic engineering can readily derive one form of expression from the parameter values in the other expression. For the sake of clarity and consistency, the description and discussion in the present invention utilizes the expression of serial resistance and serial reactance. For simplicity, serial resistance and serial reactance are simply called resistance and reactance.

Figure 20:
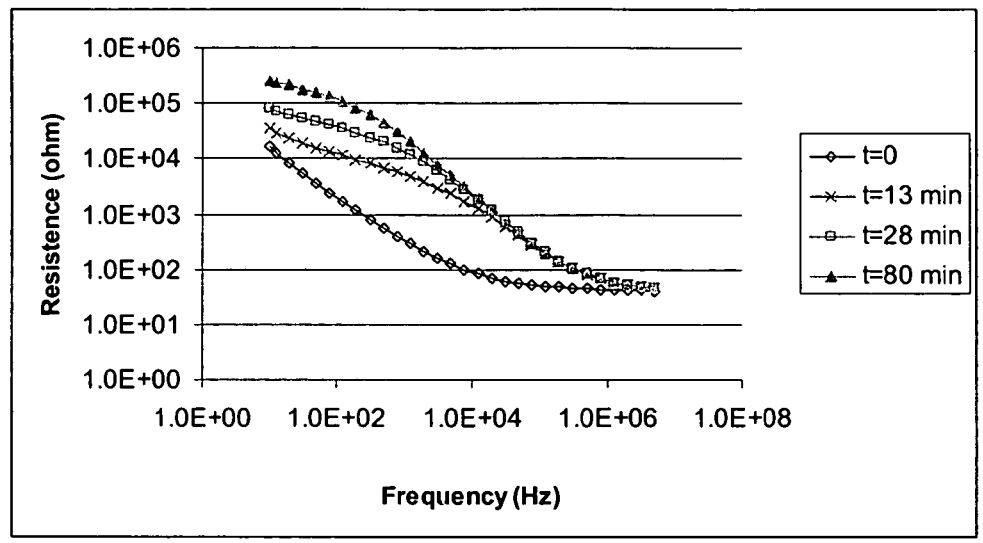
FIG. 20(A) shows typical frequency spectra of measured resistance for circle-on-line electrode structures (line width=30 micron line gap=80 micron, circle diameter=90 micron) fabricated on glass substrates under various conditions. The glass substrates containing electrode structures are electrode devices. Plastic wells were assembled over electrode structures to form a test device. The surface of the electrode structures was immobilized with alkaline phosphate molecules by first coating the electrodes with biotin-labeled bovine serum albumin and followed by incubating the electrodes in streptavidin modified alkaline phosphate to allow streptavidin-modified alkaline phosphate (AP) to bind to biotin on the electrode surfaces. After streptavidin-modified AP was coated onto the electrode surfaces, the well was washed extensively with Tris buffer (pH=7.6). Tris solution containing BCIP (17 ul BCIP stock in 1.5 ml Tris, BCIP stock was prepared in DMSO having a 25 mg/ml concentration) and NBT (33 ul in 1.5 ml Tris, NBT stock was prepared in de-ionized water having a 25 mg/ml concentration) was then added into the well. Impedance measurement was performed immediately after and at different time points after addition of the solution, (a) symbol ◇, immediately after addition of the solution, (b) symbols of X, □, ▲ for 13 (X), 28 (□) and 80 (▲) minutes after the solution was added.
FIG. 20(B) shows a frequency spectrum of measured reactance for the same electrode structures under the same conditions as in FIG. 20(A): (a) symbol ◇, immediately after addition of the solution, (b) symbols of X, □, ▲ for 13 (X), 28 (□) and 80 (▲) minutes after the solution was added. Note that the reactance shown in FIG. 20(B) is the absolute value of the reactance, in another word, the magnitude of the reactance. For the measurement taken immediately after the addition of the solution, the reactance was capacitive in nature between 10 Hz and 500 kHz and inductive in nature between 792 kHz and 5 MHz. For other measurements, the reactance was capacitive in nature between 10 Hz and 3.155 MHz and inductive in nature at 5 MHz.
FIG. 20(C) the ratio of the resistance measured at different time points after the solution was added into the well to the resistance measured immediately after the solution was added into the well.
FIG. 20(D) the ratio of the reactance measured at different time points after the solution was added into the well to the reactance measured immediately after the solution was added into the well.
Figure 20:
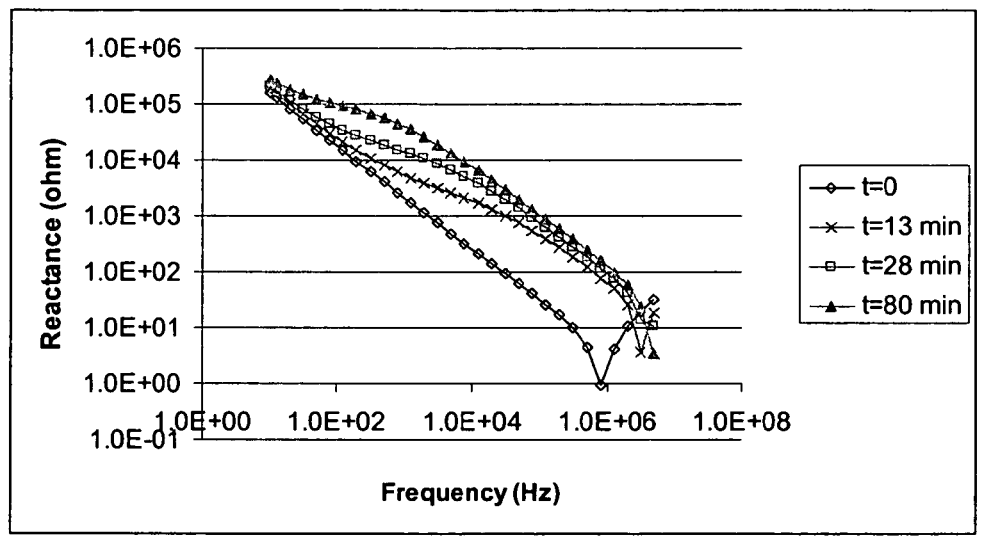

FIG. 20(A) shows typical frequency spectra of measured resistance for circle-on-line electrode structures (line width=30 micron, line gap=80 micron, circle diameter=90 micron) fabricated on glass substrates under various conditions. The glass substrates containing electrode structures are electrode devices. Plastic wells were assembled over electrode structures to form a test device. The surface of the electrode structures was immobilized with alkaline phosphate molecules by first coating the electrodes with biotin-labeled bovine serum albumin and followed by incubating the electrodes in streptavidin modified alkaline phosphate to allow streptavidin-modified alkaline phosphate (AP) to bind to biotin on the electrode surfaces. After streptavidin-modified AP was coated onto the electrode surfaces, the well was washed extensively with Tris buffer (pH=7.6). Tris solution containing BCIP (17 ul BCIP stock in 1.5 ml Tris, BCIP stock was prepared in DMSO having a 25 mg/ml concentration) and NBT (33 ul in 1.5 ml Tris, NBT stock was prepared in de-ionized water having a 25 mg/ml concentration) was then added into the well. Impedance measurement was performed immediately after and at different time points after addition of the solution, (a) symbol ◊, immediately after addition of the solution, (b) symbols of X, □, ▲ for 13 (X), 28 (□) and 80 (▲) minutes after the solution was added. With enzyme-mediated reaction occurring on the electrode surfaces, the product of this reaction precipitated on the electrode surfaces and resulted in an increase of series resistance of the electrodes. For the impedance measurement taken immediately (less than 1 minute) after addition of the solution, the enzyme-mediated reaction did not produce much precipitation on the electrode surfaces, typically, the high frequency (e.g., around 1 MHz and above) impedance (resistance and reactance) is mainly determined by the electrode geometry and electrical property of the medium (electrical conductivity and dielectric permittivity) of the solution that is introduced over the electrode structure. At lower frequencies, there exists a so-called "electrode polarization" effect, leading to the frequency dependent resistance and capacitance ((see, for example, Schwan, H. P., "Linear and nonlinear electrode polarization and biological materials", in Ann. Biomed. Eng., Vol. 20, pp 269-288, 1992; Jaron. D., Schwan, H P and Geselowitz., "A mathematical model for the polarization impedance of cardiac pacemaker electrodes", in Med. Biol. Eng., Vol. 6, pp 579-594). For the condition of 13 minutes after the solution was introduced to the well, precipitation of the product of the enzyme mediated reactions caused a large change in the impedance between the electrodes. Because of the non-conducting or little-conducting nature of the precipitation product on the electrode surfaces, the frequency spectrum of the resistance of the electrode structures was altered. Typically, there was an increase in resistance for frequencies below MHz. There was small change in the higher frequency region.

FIG. 20(B) shows a frequency spectrum of measured reactance for the same electrode structures under the same conditions as in FIG. 20(A): (a) symbol ◊, immediately after addition of the solution, (b) symbols of X, □, ▲ for 13 (X), 28 (□) and 80 (▲) minutes after the solution was added. Note that the reactance shown in FIG. 20(B) is the absolute value of the reactance, in another word, the magnitude of the reactance. For the measurement taken immediately after the addition of the solution, the reactance was capacitive in nature between 10 Hz and 500 kHz and inductive in nature between 792 kHz and 5 MHz. For other measurements, the reactance was capacitive in nature between 10 Hz and 3.155 MHz and inductive in nature at 5 MHz. With enzyme-mediated reaction occurring on the electrode surfaces, the product of this reaction precipitated on the electrode surfaces and resulted in an increase of series reactance of the electrodes. For the impedance measurement taken immediately (less than 1 minute) after addition of the solution, the enzyme-mediated reaction did not produce much precipitation on the electrode surfaces, typically, the high frequency (e.g. around 1 MHz and above) impedance (resistance and reactance) is mainly determined by the electrode geometry and electrical property of the medium (electrical conductivity and dielectric permittivity) of the solution that is introduced over the electrode structure. At lower frequencies, there exists a so-called "electrode polarization" effect, leading to the frequency dependent resistance and capacitance (see, for example, Schwan, H. P., "Linear and nonlinear electrode polarization and biological materials", in Ann. Biomed. Eng., Vol. 20, pp 269-288, 1992; Jaron, D., Schwan, H P and Geselowitz., "A mathematical model for the polarization impedance of cardiac pacemaker electrodes", in Med. Biol. Eng., Vol. 6, pp 579-594). For the condition of 13 minutes after the solution was introduced to the well, precipitation of the product of the enzyme mediated reactions caused a large change in the impedance between the electrodes. Because of the non-conducting or little-conducting nature of the precipitation product on the electrode surfaces, the frequency spectrum of the reactance of the electrode structures was also altered. Different from the changes occurred to the measured resistance, large relative change in reactance occurred for high frequencies. Relatively, small changes in reactance occurred for low frequencies (for example, less than 100 Hz).

Figure 20C:
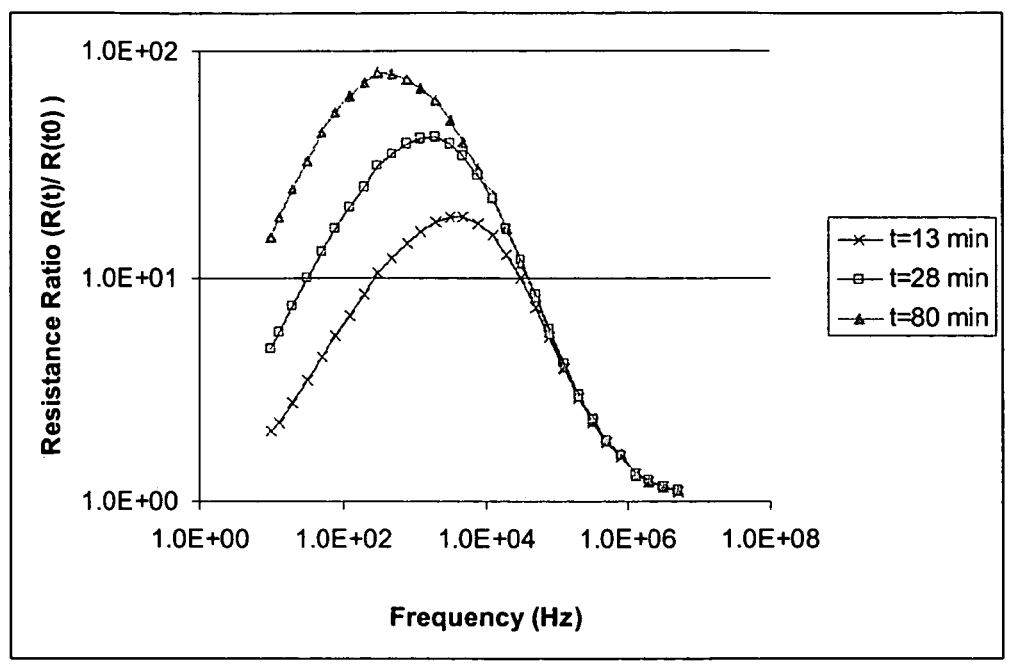

If the ratio of resistance is measured at different time points of molecular reaction (i.e. at different time points after the addition of the solution), compared to the resistance measured immediately after the addition of the solution, and the resulting ratio plotted (namely, relative change in resistance or serial resistance) as a function of the frequency, typically, a peak-shaped curve is obtained (FIG. 20(C)). At high frequency, there is small or no change in the impedance (in this case, the serial resistance), the ratio is close to one. With decreasing frequency, this ratio increases until it reaches a peak-value. With decreasing the frequency further, the ratio decreases. Even at 10 Hz, the ratio is still significantly higher than one.

Figure 20D:
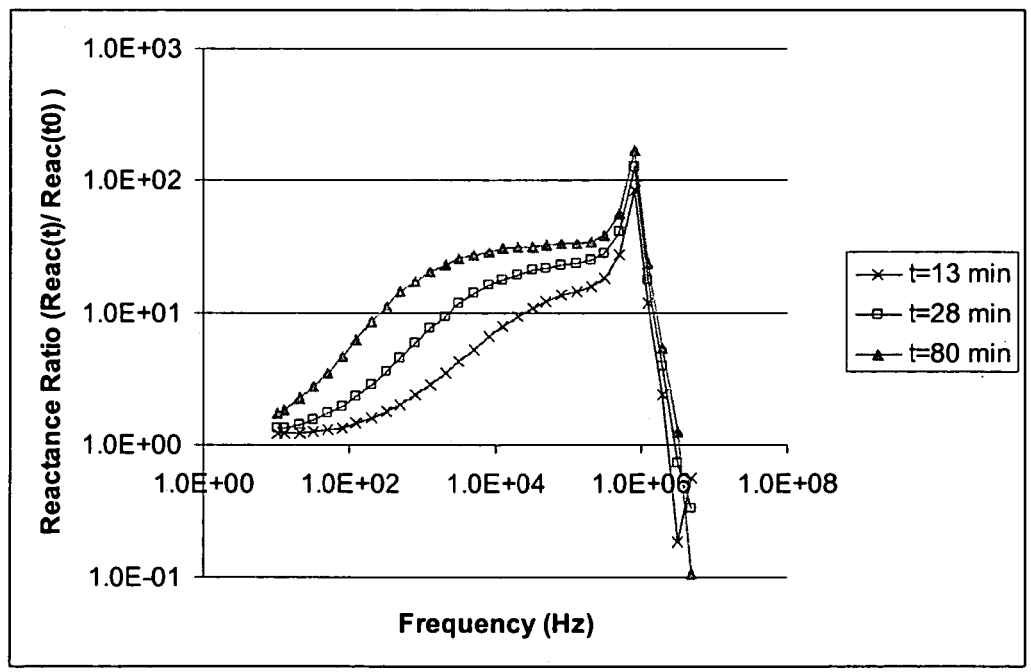
Figure 21:
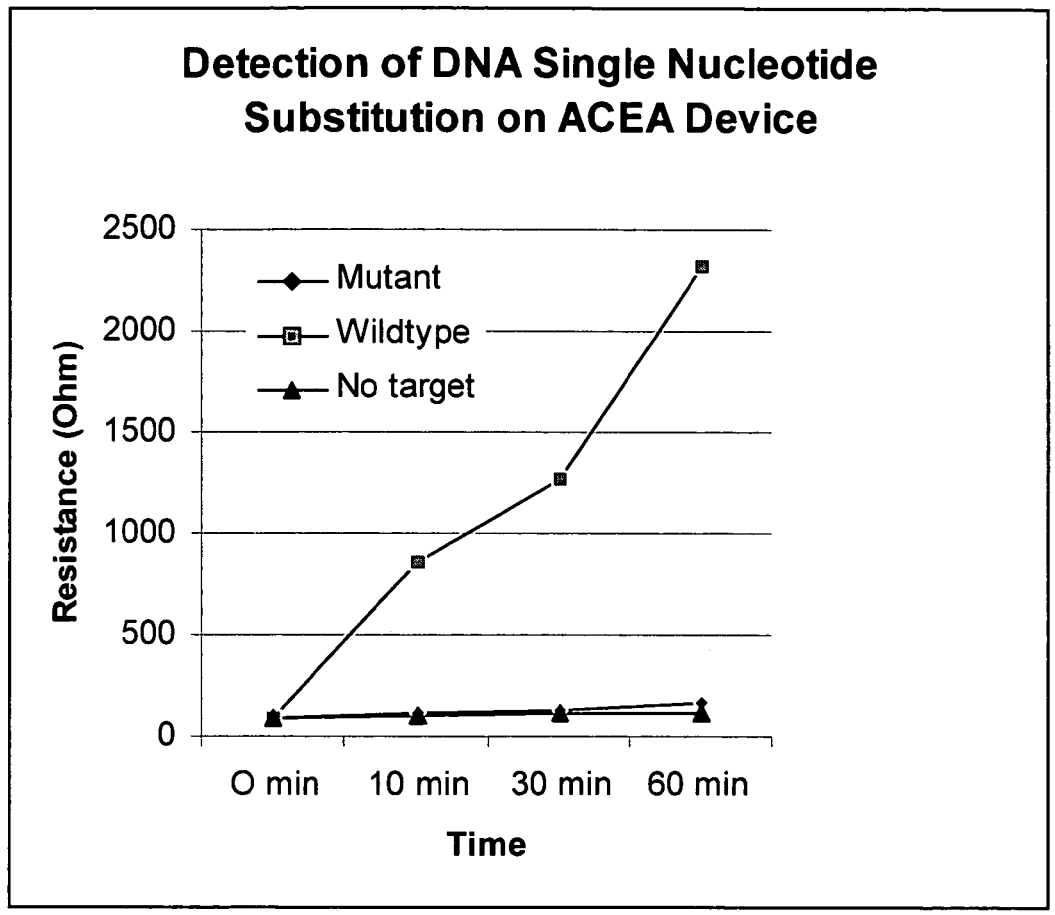
FIG. 21 illustrates the results for specific detection and discrimination of DNA nucleotide substitutions on an ACEA device. The ACEA device is a glass substrate (~18 mm by 78 mm) on which 16 electrode structure units were fabricated arranged in a 2 by 8 configuration where the unit-to-unit spacing is 9 mm. Gold (~0.2 micron) over Cr (~0.03 micron) film was deposited on the glass substrate. The electrode structure unit having a circle-on-a-line electrode geometry (line width 30 micron; circle diameter: 90 micron, line gap: 80 micron) was patterned and fabricated using thin-film photolithography technique (photoresist deposition, mask-covered UV or other light source exposure, photoresist curing, photoresist develop, wet etching of gold metal, removal of remaining gold or other metals). To use the device, a hollow plastic well strip having 16 cylinder shaped, bottomless wells was bonded to the electrode device so that the electrode structure units were exposed to experiment liquid sample when the sample was added to the plastic wells. The sensor area diameter is about 3 mm and the diameter of the plastic wells is about 6.5 mm. Before use, the device surface was treated with 1N HCl for 15 min, followed by rinsing with deionized water. Three oligonucleotide sequences specific for *Chlamydia trachomatis* 16S ribosome RNA (accession No. D85722) were synthesized for the test. They are (1) a 40 mer 5' end phophothiol-modified capture oligonucleotide sequence (5'-ZZZZGATTTGAGCGTACCAGGTAAA-GAAGCACCGGCTAACTCCG), (2) a 20 mer wildtype 5' end biotinylated target sequence (5' bio-CGGTGCTTCTT-TACCTGGTA) and (3) a 20 mer mutant 5' end biotinylated target sequence with a single nucleotide substitution (C to A at the position 9). In this experiment, the capture oligonucleotide was dissolved in deionized water at concentration of 2 μM. A better DNA coating efficiency in 1 M $KH_2PO_4$ than in $H_2O$ was reported by Tonya M. Herne and Michael J. Tarlov (Herne T M and Tarlov M J, Characterization of DAN Probes Immobilized on Gold Surfaces. J. Am. Chem. Soc. 1997, 119, 8916-8920). For coating the sensor surface with the capture oligonucleotide sequence, 100 μl of 2 μM capture oligonucleotide were added to each sensor and incubated at room temperature for 2 hours, followed by wash with phosphate buffered saline (PBS). After wash, the sensor surface was blocked with 0.3% BSA for 30 min followed by wash with PBS. For DNA hybridization, 100 μl of either 1 nM wildtype or 1 nM mutant oligonucleotide sequences in hybridization buffer (1.0 M NaCl with 10 mM Tris buffer, pH 7.4 and 1 mM EDTA) were added to the capture oligonucleotide-coated sensors. For negative control, no DNA target was added. Hybridization was carried out at 42° C. for 30 min followed by wash with phosphate buffer with 50 mM NaCl. For detection of DNA hybridization and discrimination of single nucleotide substitution, 100 μl of streptavidin labeled alkaline phosphotase (1:2000 dilution in Tris buffer) was added to each sensor and incubated for 30 min at room temperature followed by wash with Tris buffer. After wash, 100 μl of an alkaline phosphotase substrate mix, BCIP/BNT was added and the reaction was monitored on the impedance analyzer in real time. As shown in the figure, the specific hybridization between the capture sequence and the wildtype target sequence can be steady detected on the electronic device, the signal for which is 92.6 fold higher than the signal generated from the negative control sensor at 60 min. Here the signal is the resistance measured 5 kHz between electrode structures in each well. Notably, the mutant sequence with single nucleotide substitution generated very weak signal compared to its wildtype sequence. The signal difference at 60 min between the wildtype sequence and the mutant sequence is 30 fold.
Figure 23:
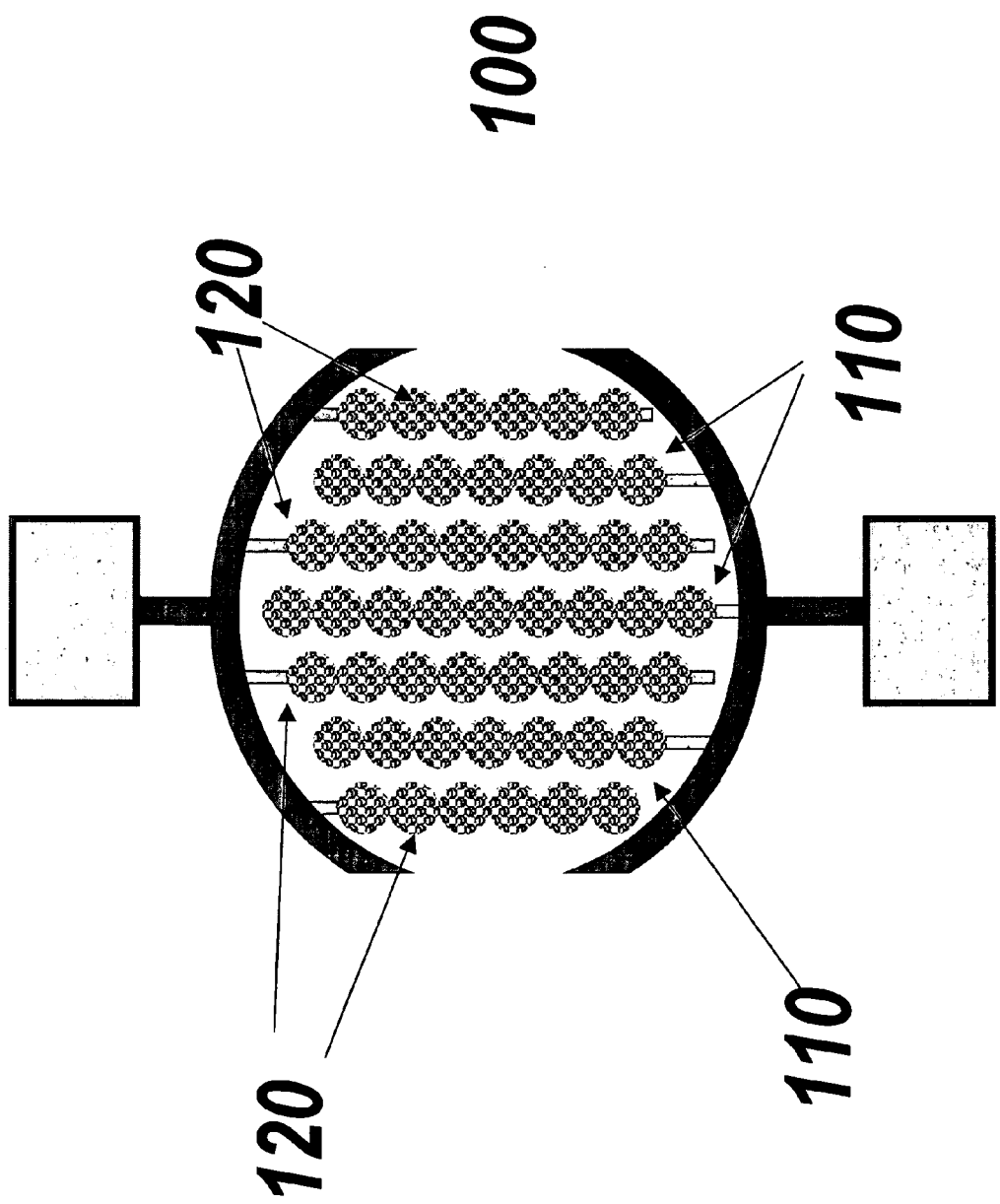
FIG. 23 is a schematic representation of an apparatus where the electrode surface has been modified with molecules that promote cell adhesions.

It is also possible to plot a relative change in the reactance or capacitance value and use the change in the reactance to monitor and reflect the molecular reaction taking place on the electrode surfaces or to monitor the enzyme-mediated reaction that causes precipitation of the reaction product on the electrode surfaces (see FIG. 20(D)). Furthermore, expression of impedance in terms of parallel resistance and reactance can also be used for describing the change in impedance due to molecular reactions occurring on the electrode surfaces.

II. Impedance Frequency Spectrum for Cell Assays

Figure 38A:
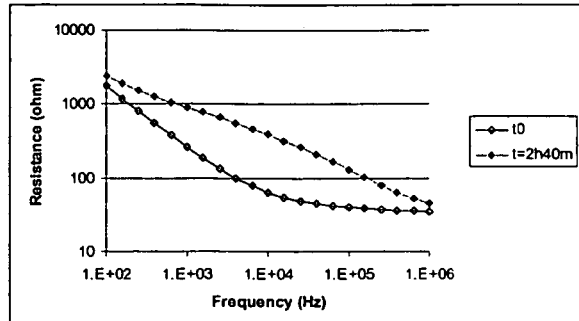
FIG. 38(A) shows typical frequency spectra of measured resistance for circle-on-line electrode structures fabricated on glass substrates under two conditions: (a), open symbol, shortly after (within 10 minutes, cells had not attached yet to the electrode and substrate surfaces) the tissue culture medium containing HT1080 cells was added to a well containing the electrode structure; (b) solid symbol, 2 h 40 minutes (cells were attached to the electrode and substrate surfaces) after the culture medium containing HT1080 cells were added to the wells containing the electrode structures on the well bottom surface. During the 2 h 40 minutes period, the well was placed into a tissue culture incubator that was set at 37° C. and 5% $CO_2$ level. The electrode structure is of 3B design where the line width is 30 micron, the gap between lines is 80 micron and the continuous circles on the lines have 90 micron in diameter. In this example, the total area covered the electrodes and the gaps between the electrodes correspond to a circle of 3 mm in diameter. The electrode structure on the glass substrate forms a bottom of a conical shaped well where the top diameter of the well is about 6.5 mm in diameter whereas the bottom diameter is about 5 mm. For the experiment, total 100 microliter volume of the tissue culture medium containing about 7000 HT 1080 cells was added to the wells comprising the electrode structure on the bottom of the well.

FIG. 38(A) shows typical frequency spectra of measured resistance for circle-on-line electrode structures fabricated on glass substrates under two conditions: (a), open symbol, shortly after (within 10 minutes, cells had not attached yet to the electrode and substrate surfaces) the tissue culture medium containing HT1080 cells was added to a well containing the electrode structure, (b) solid symbol, 2 h 40 minutes (cells were attached to the electrode and substrate surfaces) after the culture medium containing HT1080 cells were added to the wells containing the electrode structures on the well bottom surface. Shortly after (within 10 minutes) cell-containing medium was added the well, the cells did not have enough time to attach to the electrodes. This was confirmed by that the measured impedance (resistance and reactance) for the electrode structure with the cell-containing medium was the same, or almost the same, as that obtained for the cell-free medium added to the well. For the condition when the cell-free culture medium was introduced over the electrodes, or when the cell-containing medium was introduced over the electrodes but the cells did not have enough time to attach to the electrode structures, typically, the high frequency (e.g., around 1 MHz and above) impedance (resistance and reactance) is mainly determined by the electrode geometry and electrical property of the medium (electrical conductivity and dielectric permittivity) of the solution that is introduced over the electrode structure. At lower frequencies, there exists a so-called "electrode polarization" effect, leading to the frequency dependent resistance and capacitance ((see, for example, Schwan, H. P., "Linear and nonlinear electrode polarization and biological materials", in Ann. Biomed. Eng., Vol. 20, pp 269-288, 1992; Jaron. D. Schwan, H P and Geselowitz., "A mathematical model for the polarization impedance of cardiac pacemaker electrodes", in Med. Biol. Eng., Vol. 6, pp 579-594). For the condition of 2 h 40 minutes after the cell-containing medium was introduced to the well which was placed into a tissue culture incubator for over 2 h 40 minutes, the cells were given enough time to attach and spread (as confirmed by microscope examination of the cells in the region not covered by the electrodes). Because of the non-conducting nature of the cell membrane, the frequency spectrum of the resistance of the electrode structures was altered. Typically, there was an increase in the inter-mediate frequencies (1 kHz to 100 kHz). There was small change in either lower or higher frequency regions.

Figure 38B:
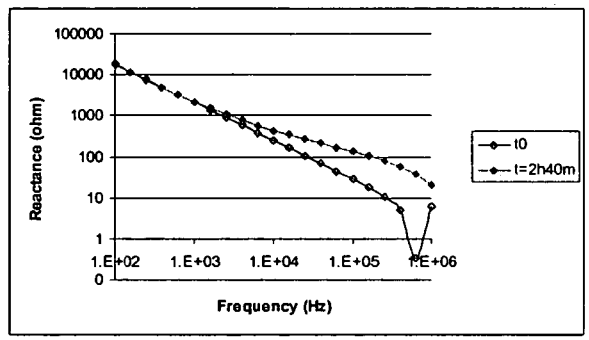
FIG. 38(B) shows a frequency spectrum of measured reactance for the same electrode structures under two same conditions as in FIG. 38(A). Note that the absolute magnitude of the reactance was plotted in log scale (in the same way as the curves in FIG. 26). Except for high frequencies of 1 MHz and about 580 kHz, the reactance was negative (capacitance reactance) for the electrode structures measured shortly after (within 10 minutes) the tissue culture medium containing HT1080 cells was added to the well containing the electrode structures. For the reactance measured at 2 h 40 minutes after cell suspension was added into the well containing the electrode structures, the reactance was negative throughout the frequency range measured between 100 Hz and 1 MHz.

FIG. 38(B) shows a frequency spectrum of measured reactance for the same electrode structures under two same conditions as in FIG. 38(A): (a), open symbol, shortly after (within 10 minutes, cells had not attached yet to the electrode and substrate surfaces) the tissue culture medium containing HT1080 cells was added to a well containing the electrode structure; (b) solid symbol, 2 h 40 minutes (cells were attached to the electrode and substrate surfaces) after the culture medium containing HT1080 cells were added to the wells containing the electrode structures on the well bottom surface. Shortly after (e.g., within 10 minutes) cell-containing medium was added the well, the cells did not have enough time to attach to the electrodes. This was confirmed by that the measured impedance (resistance and reactance) for the electrode structure with the cell-containing medium was the same, or almost the same, as that obtained for the cell-free medium added to the well. As described above, for the condition when the cell-free culture medium was introduced over the electrodes, or when the cell-containing medium was introduced over the electrodes but the cells did not have enough time to attach to the electrode structures typically, the high frequency (e.g., around 1 MHz and above) resistance is mainly determined by the electrode geometry and electrical conductivity of the solution that is introduced over the electrode structure. At lower frequencies, there exists a so-called "electrode polarization" effect, leading to the frequency dependent resistance and capacitance (see, for example, Schwan, H. P., "Linear and nonlinear electrode polarization and biological materials", in Ann. Biomed. Eng., Vol. 20, pp 269-288, 1992; Jaron, D., Schwan, H P and Geselowitz., "A mathematical model for the polarization impedance of cardiac pacemaker electrodes", in Med. Biol. Eng., Vol. 6, pp 579-594). For the condition of 2 h 40 minutes after the cell-containing medium was introduced to the well, which was placed in a tissue culture incubator for 2 h 40 minutes, the cells were given enough time to attach and spread (as confirmed by microscope examination of the cells in the region not covered by the electrodes). Under such a condition, because of the non-conducting nature of the cell membrane, the frequency spectrum of the reactance of the electrode structures was altered. Different from the change in the resistance, the major relative change occurred in the higher frequencies where the overall magnitude of the reactance was also increased significantly because of the cells attached onto the electrodes.

Figure 38C:
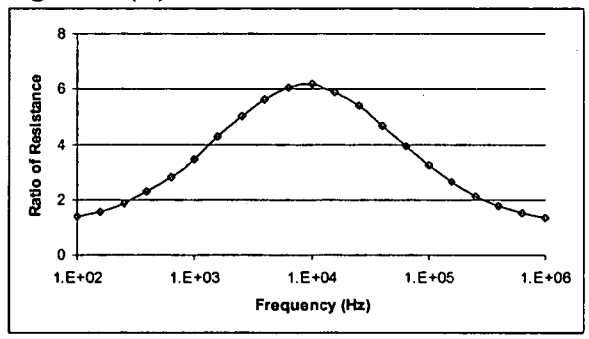
FIG. 38(C) shows the frequency spectrum of the ratio of resistance measured with cell-attached onto the electrode surfaces to the resistance measured without cells-attached for the results illustrated in FIG. 38(A).
Figure 38D:
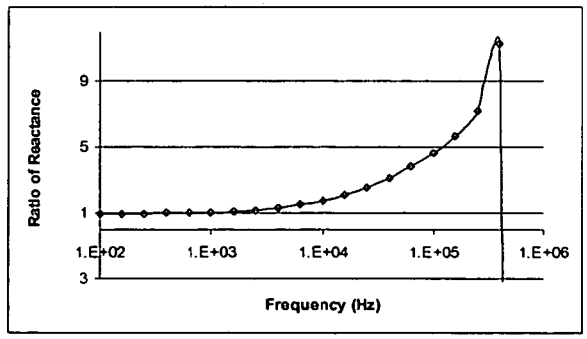
FIG. 38(D) shows the frequency spectrum of the ratio of reactance measured with cell-attached onto the electrode surfaces to the resistance measured without cells-attached for the results illustrated in FIG. 38(A). Note that for this calculation of reactance ratio, the polarity of the reactance (i.e., capacitance and inductive reactance) was taken into account.
Figure 39A:
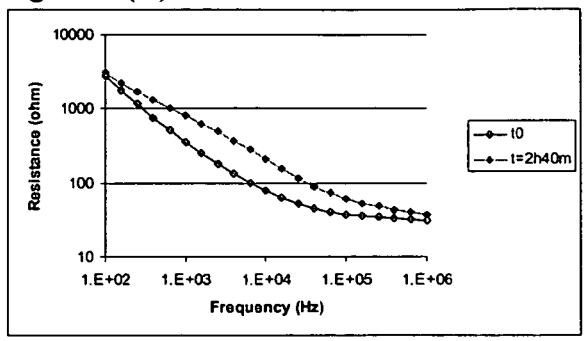
FIG. 39(A) shows typical frequency spectra of measured resistance for circle-on-line electrode structures fabricated on glass substrates under two conditions: (a), open symbol, shortly after (within 10 minutes, cells had not attached yet to the electrode and substrate surfaces) the tissue culture medium containing HT1080 cells was added to a well containing the electrode structure; (b) solid symbol, 2 h 40 minutes (cells were attached to the electrode and substrate surfaces) after the culture medium containing HT1080 cells were added to the wells containing the electrode structures on the well bottom surface. During the 2 h 40 minutes period, the well was placed into a tissue culture incubator that was set at 37° C. and 5% $CO_2$ level. The electrode structure is of 3B design where the line width is 30 micron, the gap between lines is 80 micron and the continuous circles on the lines have 90 micron in diameter. In this example, the total area covered the electrodes and the gaps between the electrodes correspond to a circle of 3 mm in diameter. The electrode structure on the glass substrate forms a bottom of a conical shaped well where the top diameter of the well is about 6.5 mm in diameter whereas the bottom diameter is about 5 mm. For the experiment, total 100 microliter volume of the tissue culture medium containing about 3200 HT 1080 cells was added to the wells comprising the electrode structure on the bottom of the well.
Figure 39B:
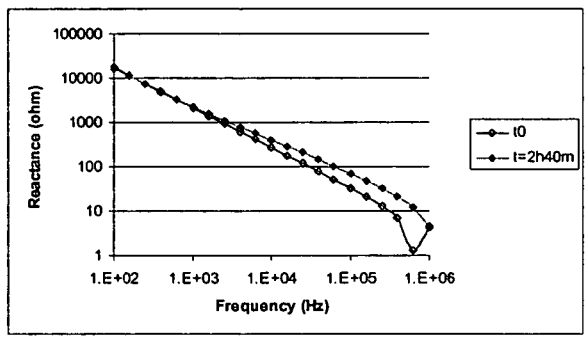
FIG. 39(B) shows a frequency spectrum of measured reactance for the same electrode structures under two same conditions as in FIG. 38(A). Note that the absolute magnitude of the reactance was plotted in log scale (in the same way as the curves in FIG. 26). Except for high frequencies of 1 MHz and about 580 kHz, the reactance was negative (capacitance reactance) for the electrode structures measured shortly after (within 10 minutes) the tissue culture medium containing HT1080 cells was added to the well containing the electrode structures. For the reactance measured at 2 h 40 minutes after cell suspension was added into the well containing the electrode structures, the reactance was negative throughout the frequency range measured between 100 Hz and 1 MHz.
Figure 39C:
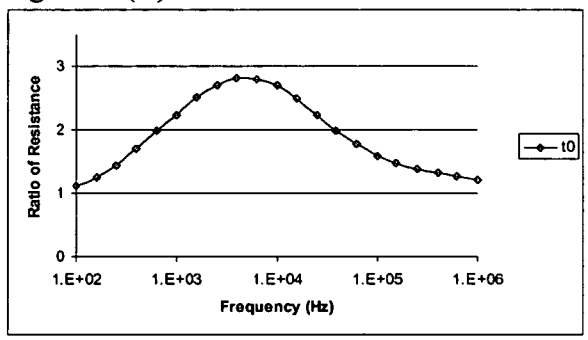
FIG. 39(C) shows the frequency spectrum of the ratio of resistance measured with cell-attached onto the electrode surfaces to the resistance measured without cells-attached for the results illustrated in FIG. 39(A).
Figure 39D:
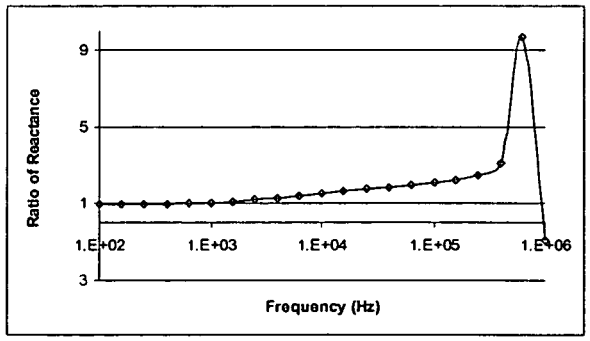
FIG. 39(D) shows the frequency spectrum of the ratio of reactance measured with cell-attached onto the electrode surfaces to the resistance measured without cells-attached for the results illustrated in FIG. 39(A). Note that for this calculation of reactance ratio, the polarity of the reactance (i.e., capacitance and inductive reactance) was taken into account.

If we take the ratio of resistance measured with cell-attached to the resistance measured without cells-attached and plot this ratio (namely, relative change in resistance or serial resistance) as a function of the frequency, typically, we observe a peak-shaped curve (FIG. 38(C)). At lower frequency, there is small or no change in the impedance (in this case, the serial resistance), the ratio is approximately one. With increasing frequency, this ratio increases until it reaches a peak-value. With increasing the frequency further, the ratio decreases to about one at high frequencies. It should be pointed out that it is also possible to plot a relative change in the reactance or capacitance value and use the change in the reactance to monitor and reflect the cell attachment to the electrode surfaces (see FIG. 38(D)). Furthermore, expression of impedance in terms of parallel resistance and reactance can also be used for describing the change in impedance due to cell attachment to the electrode surfaces.

The peak value of the resistance ratio (i.e., the ratio of the resistance with cell-attached to the electrodes to the resistance when no-cell-attached to the electrodes) and the frequency at which the peak value occurs depend on, among other things, how many cells attached on the electrode surface, how tight such attachment is, the size of the cells, what dielectric properties the cells have for their plasma membrane and intracellular components. For a number of the cell types we have tested, we found that more cells attached to the electrode surface result in higher peak value for the ratio and the higher frequency value at which the peak occurs, for the cells of the same type and under similar physiological conditions (e.g. in exponential growth phase).

Figure 40A:
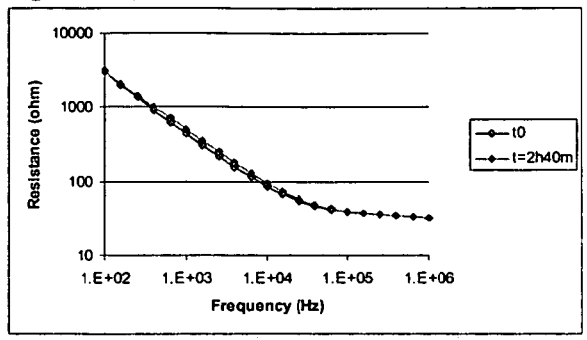
FIG. 40(A) shows typical frequency spectra of measured resistance for circle-on-line electrode structures fabricated on glass substrates under two conditions: (a), open symbol, shortly after (within 10 minutes, cells had not attached yet to the electrode and substrate surfaces) the tissue culture medium containing HT1080 cells was added to a well containing the electrode structure; (b) solid symbol, 2 h 40 minutes (cells were attached to the electrode and substrate surfaces) after the culture medium containing HT1080 cells were added to the wells containing the electrode structures on the well bottom surface. During the 2 h 40 minutes period, the well was placed into a tissue culture incubator that was set at 37° C. and 5% $CO_2$ level. The electrode structure is of 3B design where the line width is 30 micron, the gap between lines is 80 micron and the continuous circles on the lines have 90 micron in diameter. In this example, the total area covered the electrodes and the gaps between the electrodes correspond to a circle of 3 mm in diameter. The electrode structure on the glass substrate forms a bottom of a conical shaped well where the top diameter of the well is about 6.5 mm in diameter whereas the bottom diameter is about 5 mm. For the experiment, total 100 microliter volume of the tissue culture medium containing about 500 HT 1080 cells was added to the wells comprising the electrode structure on the bottom of the well.
Figure 40B:
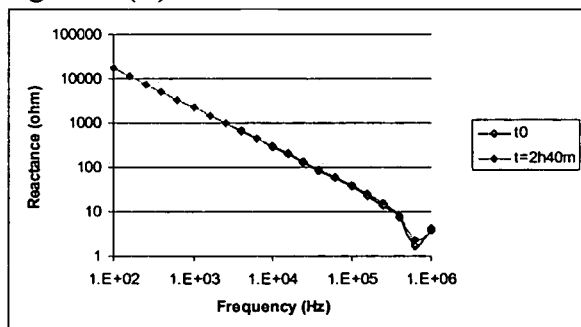
FIG. 40(B) shows a frequency spectrum of measured reactance for the same electrode structures under two same conditions as in FIG. 40(A). Note that the absolute magnitude of the reactance was plotted in log scale (in the same way as the curves in FIG. 26). Except for high frequencies of 1 MHz and about 580 kHz, the reactance was negative (capacitance reactance) for the electrode structures measured under both conditions.
Figure 40C:
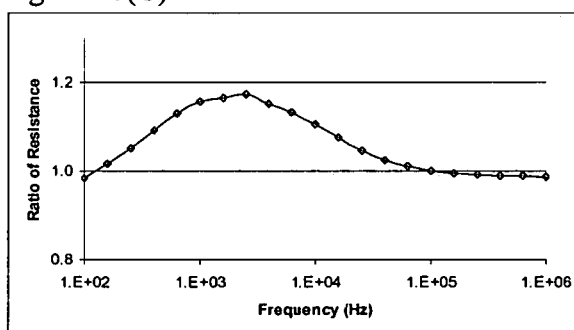
FIG. 40(C) shows the frequency spectrum of the ratio of resistance measured with cell-attached onto the electrode surfaces to the resistance measured without cells-attached for the results illustrated in FIG. 40(A).
Figure 40D:
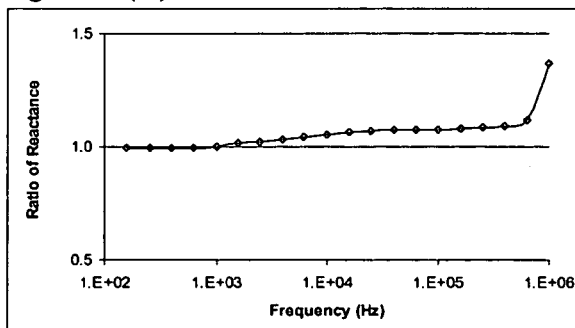
FIG. 40(D) shows the frequency spectrum of the ratio of reactance measured with cell-attached onto the electrode surfaces to the resistance measured without cells-attached for the results illustrated in FIG. 40(A). Note that for this calculation of reactance ratio, the polarity of the reactance (i.e., capacitance and inductive reactance) was taken into account.

In comparison with the results in FIGS. 38(A), 38(B) and 38(C), FIG. 39(A), 39(B), 39(C) shows the frequency spectra of the resistance, reactance and resistance ratio for a similar circle-on-line electrode with more cells applied to the wells comprising the circle-on-line electrode structures on the bottom well, FIGS. 40(A), 40(B), 40(C) shows the results for less-number of cells attached to the electrodes.

Figure 41A:
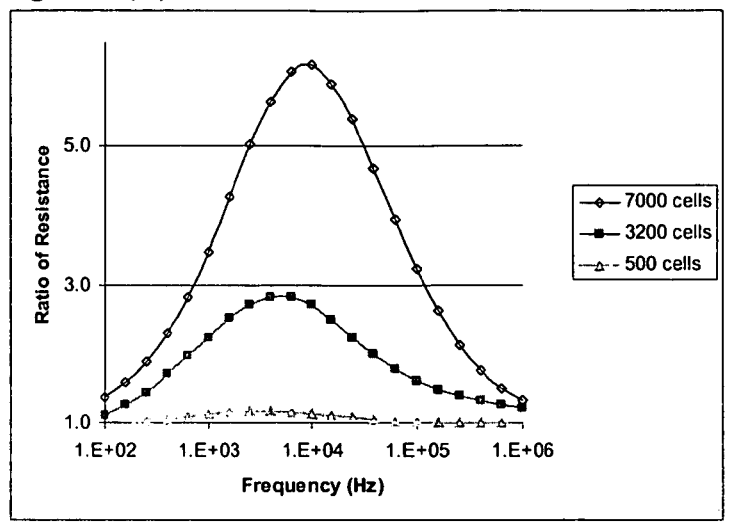
FIG. 41(A) shows the frequency spectra of resistance-ratio for different numbers of cells added into the wells comprising the same types of circle-on-line electrode structures (electrode geometry 3B).
Figure 41B:
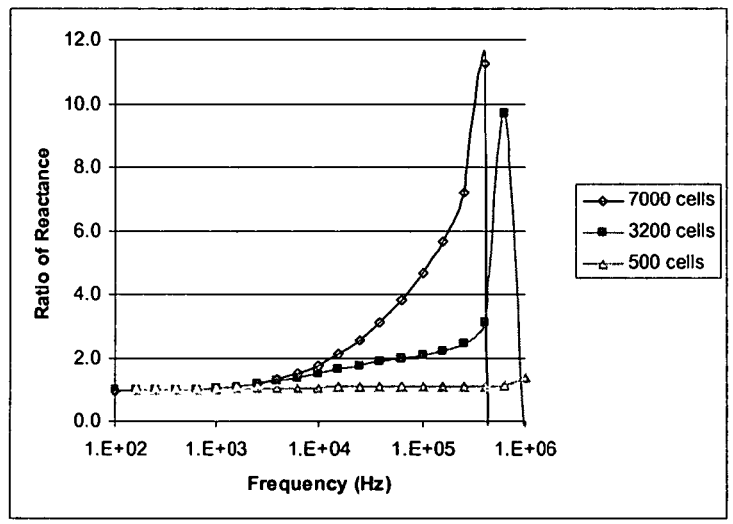
FIG. 41(B) shows the frequency spectra of reactance-ratio for different numbers of cells added into the wells comprising the same types of circle-on-line electrodes (electrode geometry 3B).
Figure 42:
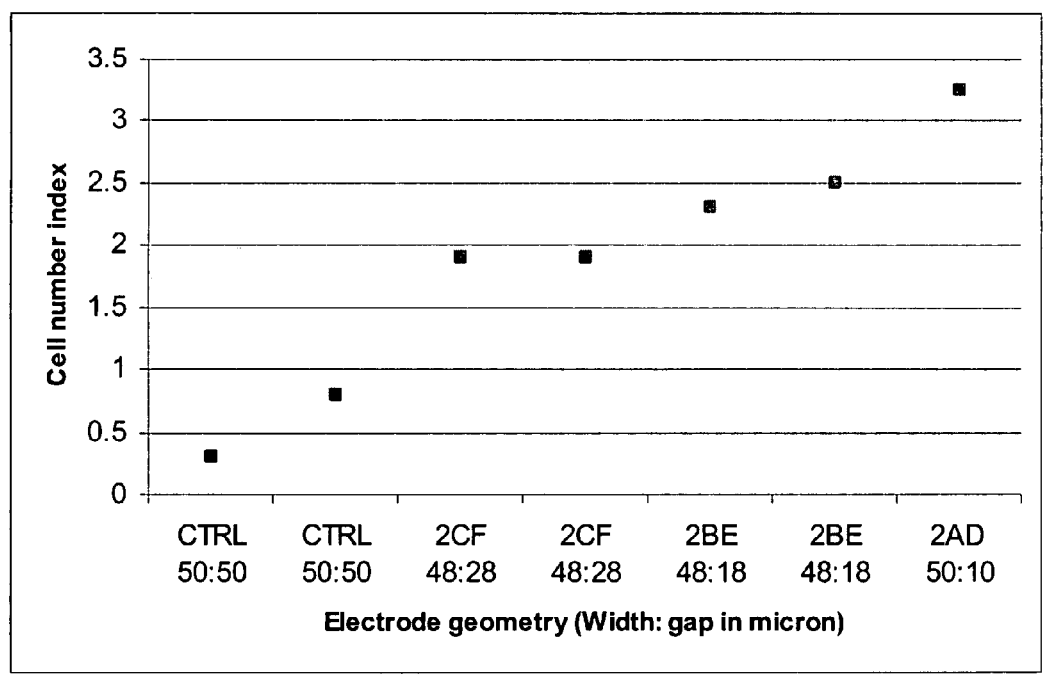
FIG. 42(A) shows comparison of frequency spectra of measured resistance and reactance for four interdigitated electrode structures of different geometry having different ratio between electrode width and electrode gaps with or without 3T3 cells attached to the electrode surfaces. The resistance and reactance spectra for the electrode structures without cells attached were measured shortly after (within 10 minutes, cells had not attached yet to the electrode and substrate surfaces) the tissue culture medium containing 3T3 cells was added to wells containing the electrode structures. The resistance and reactance spectra for the electrode structures without cells attached were measured at 3 hrs after the culture medium containing 3T3 cells were added to the wells containing the electrode structures on the well bottom surface. During the 3 h period, the wells were placed into a tissue culture incubator that was set at 37° C. and 5% $CO_2$ level. The electrode structures of 2AD geometry, 2BE geometry and 2CF geometry were fabricated on a 1 cm by 1 cm glass substrate, having electrode width of 50, 48 and 48 micron, and having electrode gap of 10, 18 and 28 micron, respectively. The area covered the electrodes and the gaps between the electrodes for 2AD, 2BE and 2CF geometry correspond to a circle of 1 mm, 3 mm and 6 mm diameter. The fourth electrode structures having electrode width and gap being both 50 micron were fabricated on a Kapton (polyimide) substrate. The area covered the electrodes and the gap between the electrodes were of a rectangular shape having 6 mm by 5 mm in dimension. In these experiments, conical shaped plastic wells having 4.5 mm in diameter at the bottom were glued to the glass substrates and Kapton substrate, which comprise different interdigitated electrodes. For the electrode structures of 2AD and 2BE geometry, the electrode structured were located at the central regions of the well bottom. For the electrode structures of 2CF geometry and the Kapton substrate, the bottom wells were covered with the electrodes and gaps between the electrodes. Prior to the experiments, the electrode and substrate surfaces were thoroughly cleaned and were coated with fibronectin. Evidently, for a nearly constant electrode width of 50 micron and for same number (about $10^4$ cells) of 3T3 cells added into the wells, reducing the gap size between the neighboring electrodes resulted in increase in the magnitude of impedance change after cell attachment relative to those of no cell attachment on electrodes.
FIG. 42(B) shows the relationship of cell number indexes for different, interdigitated electrode geometry having different ratio of electrode width to electrode gaps. The cell number index was calculated by subtracting one from the maximum ratio of resistance (the resistance measured when cells are attached to the electrode surfaces to the resistance measured when no cells are attached to the electrode surfaces at corresponding frequencies). Evidently, for a nearly constant electrode width of 50 micron and for same number (about $10^4$ cells) of 3T3 cells added into the wells, reducing the gap size between the neighboring electrodes resulted in increase in cell number index. As indicated by the data, a significant increase in the cell number index is achieved with width/gap ratio of about 1.5 or higher.
Figure 43:
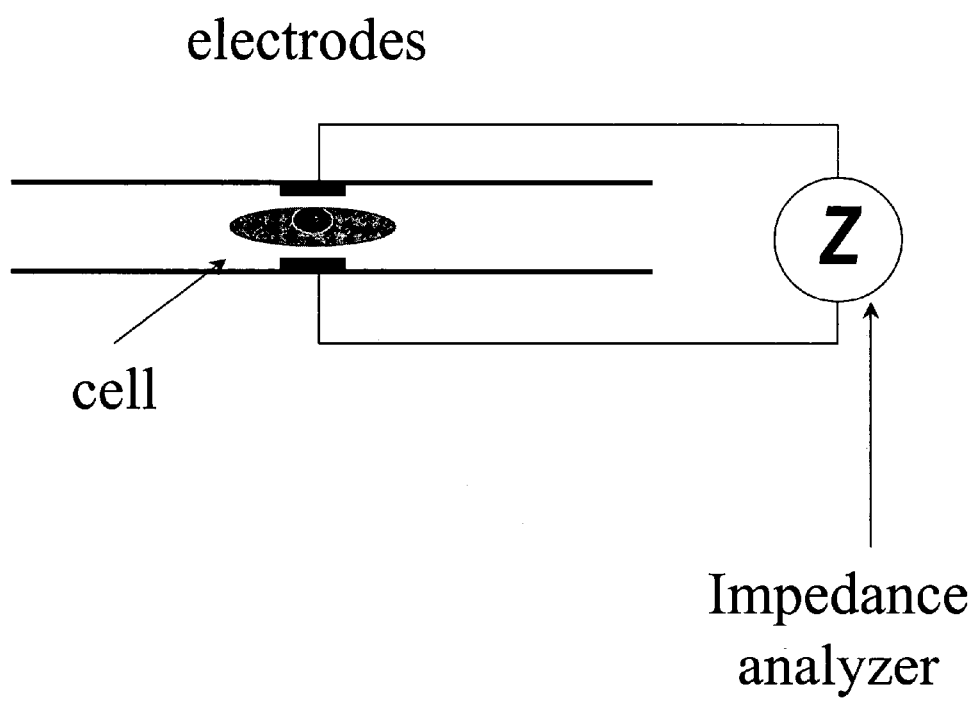
FIG. 43 is a schematic diagram for microfluidic channel-based two-electrode sensing.
Figure 44:
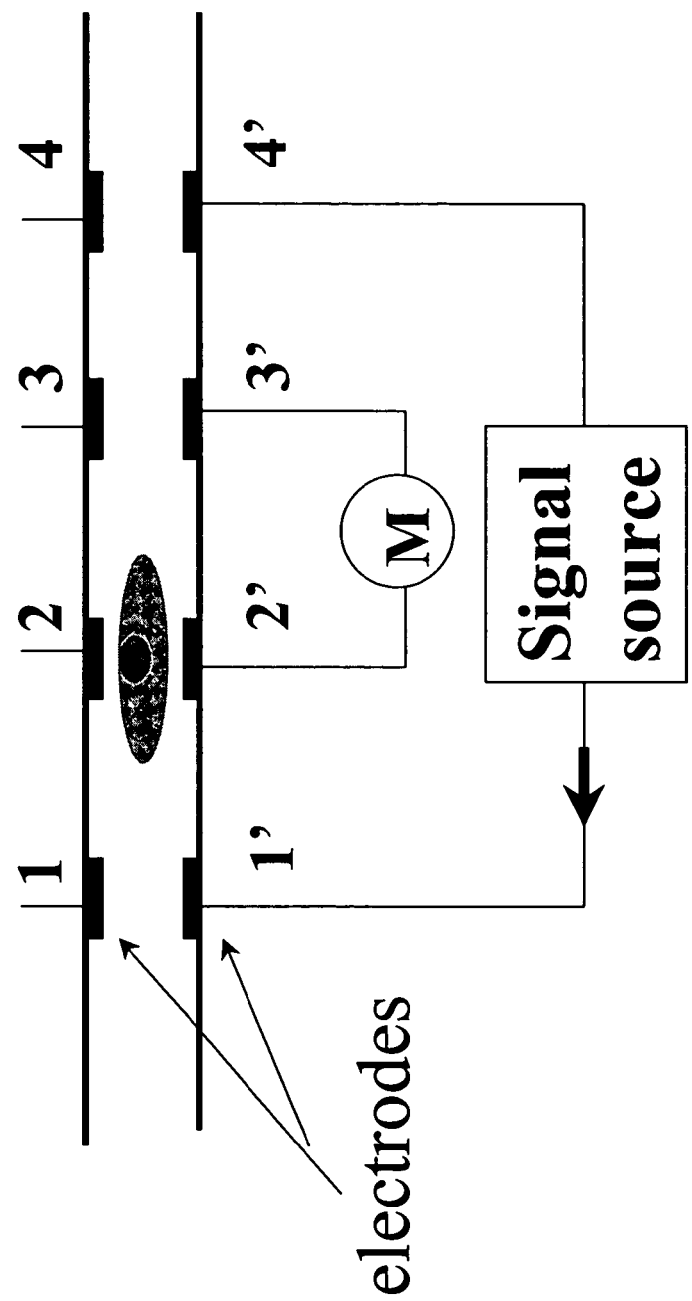
FIG. 44 is a schematic diagram for microfluidic channel-based multiple-electrode sensing. Electrodes 1 (1' and 1 are connected together) and 4 (4' and 4 are connected together) are used for supplying a constant current through the channel whilst the electrodes 2 (2' and 2 are connected together) and 3 (3' and 3 are connected together) are used for monitoring the voltage. When the cells are passing through the region defined by electrodes 2 (2') and 3 (3'), the impedance will change, leading to a change in the voltage between electrodes 2 (2') and 3 (3').
Figure 46:
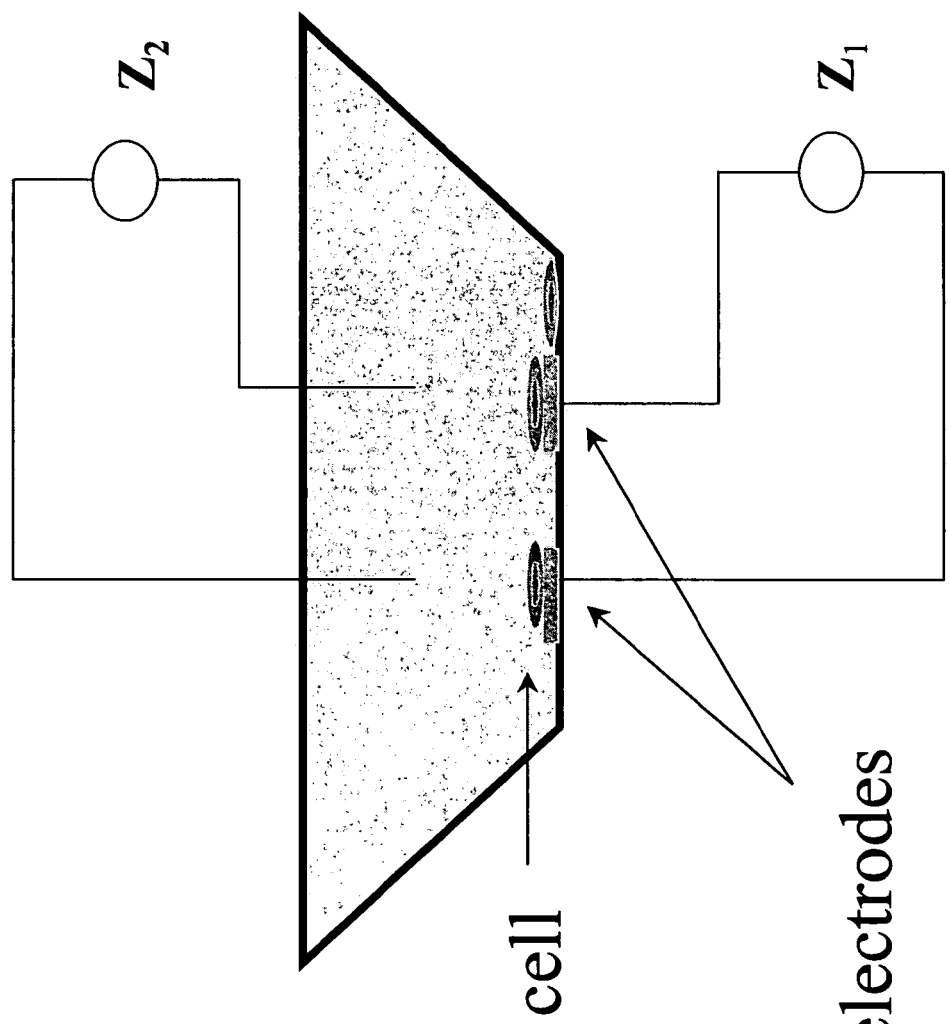
FIG. 46 is a schematic diagram showing the simultaneous measurement of impedance change ($Z_1$) to monitor cell attachment and adhesion to the electrodes and the conductivity change (as reflected in the change of impedance measured at $Z_2$) in the solution.

FIG. 41A shows the frequency spectra of resistance-ratio for different numbers of cells added into the wells comprising the same types of circle-on-line electrodes. For example, seeding about 500 cells results a maximum of 17% change in the serial resistance occurring at ~2 kHz, whilst seeding 3200 and 7000 cells resulted 182% and 517% change in serial resistance occurring at ~5 and 30 kHz, respectively. Again, the change in the serial reactance can also be used for demonstrating such relationship between the cell number and the magnitude of the change in reactance (see FIG. 41B, for example, the reactance values at 250 kHz may be used to illustrate relationship between the cell number and the magnitude of the change in reactance). Furthermore, if parallel resistance and parallel reactance are used to express the measured impedance, it is also possible demonstrate the dependent relationship between the cell number and the magnitude of the changes in parallel resistance and/or parallel reactance.

III. Derivation of Molecular Interaction Index

Based on the dependent relationship between the measured impedance and molecular interaction index, it is possible to derive a so-called "molecular interaction index" from the measured impedance frequency spectra. Various methods for calculating such a molecular interaction index can be used. In the following, we illustrate several methods for calculating such a molecular interaction index based on the change in resistance or reactance when molecular interactions occur on the electrode surfaces with respect to that of the electrode surfaces prior to the mentioned molecular interaction. The impedance (resistance and reactance) of the electrode structures prior to the molecular reaction taking place but with same sample solutions over the electrode structures is sometimes referred as baseline impedance. Thus, one approach to obtain the baseline impedance is by measuring the impedance of the electrodes or electrode structures with a solution introduced into the well containing the electrode structures, wherein the solution is the same as that used for the impedance measurements for the condition where the molecular binding reaction is monitored except without the target molecules, here the surface of the electrodes or electrode structures is also anchored with or covered with or immobilized with capturing molecules.

In one example, the molecular interaction index can be calculated by:

at each measured frequency, calculating the resistance ratio by dividing the measured resistance (when molecular interaction take place on the electrode surfaces) by the baseline resistance, finding or determining the maximum value in the resistance ratio over the frequency spectrum, and subtracting one from the maximum value in the resistance ratio.

In this case, a zero or near-zero "molecular interaction index" indicates that no molecular reaction occurs on the electrode surfaces. A higher value of "molecular interaction index" indicates that, for similar type of molecular reactions, more reactions occurred to the electrode surfaces.

In another example, the molecular interaction index can be calculated by:

at each measured frequency, calculating the resistance ratio by dividing the measured resistance (when molecular interaction take place on the electrode surfaces) to the baseline resistance, finding or determining the maximum value in the resistance ratio over the frequency spectrum and taking a log-value (e.g., based on 10 or e=2.718) of the maximum value in the In this case, a zero or near-zero "molecular interaction index" indicates that no molecular reaction occurs on the electrode surfaces. A higher value of "molecular interaction index" indicates that, for similar type of molecular reactions, more reactions occurred to the electrode surfaces.

In one example, the molecular interaction index can be calculated by:

at each measured frequency, calculating the reactance ratio by dividing the measured reactance (when molecular interaction take place on the electrode surfaces) to the baseline reactance, finding or determining the maximum value in the reactance ratio over the frequency spectrum and subtracting one from the maximum value in the resistance ratio.

In this case, a zero or near-zero "molecular interaction index" indicates that no molecular reaction occurs on the electrode surfaces. A higher value of "molecular interaction index" indicates that, for similar type of molecular reactions, more reactions occurred to the electrode surfaces.

In yet another example, the index can be calculated by:

at each measured frequency, calculating the resistance ratio by dividing the measured resistance ((when molecular interaction take place on the electrode surfaces) to the baseline resistance, then calculating the relative change in resistance in each measured frequency by subtracting one from the resistance ratio.

then integrating all the relative-change value.

In this case, a zero or near-zero "molecular interaction index" indicates that no molecular reaction occurs on the electrode surfaces. A higher value of "molecular interaction index" indicates that, for similar type of molecular reactions, more reactions occurred to the electrode surfaces.

It is worthwhile to point out that it is not necessary to derive such a "molecular interaction index" for utilizing the impedance information for monitoring molecular reaction conditions over the electrodes. Actually, one may choose to directly use impedance values (e.g., at a single fixed frequency; or at a maximum relative-change frequency, or at multiple frequencies) as an indicator of molecular interactions occurring on the electrode surfaces.

IV. Derivation of Cell Number Index

Based on the dependent relationship between the measured impedance, cell number (more accurately, the viable cell number, or attached cell number) and cell attachment status, it is possible to derive a so-called "cell number index" (or cell index) from the measured impedance frequency spectra. Various methods for calculating such a cell number index can be used. In the following, we illustrate several methods for calculating such cell number index based on the change in resistance or reactance when cells are attached to the electrode structure with respect to the cells not attached to the electrode structure. The impedance (resistance and reactance) of the electrode structures with no cell attached but with same cell culture medium over the electrode structures is sometimes referred as baseline impedance. The baseline impedance may be obtained by one or more of the following ways: (1) the impedance measured for the electrode structures with a cell-free culture medium introduced into the well containing the electrode structures, wherein the culture medium is the same as that used for the impedance measurements for the condition where the cell attachment is monitored; (2) the impedance measured shortly (e.g. 10 minutes) after the cell-containing medium was applied to the wells comprising the electrode structures on the well bottom (during the short period after cell-containing medium addition, cells do not have enough time to attach to the electrode surfaces. The length of this short-period may depend on cell type and/or surface treatment or modification on the electrode surfaces); (3) the impedance measured for the electrode structures when all the cells in the well were killed by certain treatment (e.g. high-temperature treatment) and/or reagents (e.g. detergent) (for this method to be used, the treatment and/or reagents should not affect the dielectric property of the medium which is over the electrodes).

In one example, the cell number index can be calculated by:
(1) at each measured frequency, calculating the resistance ratio by dividing the measured resistance (when cells are attached to the electrodes) by the baseline resistance.
(2) finding or determining the maximum value in the resistance ratio over the frequency spectrum
(3) and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In another example, the cell number index can be calculated by:
(1) at each measured frequency, calculating the resistance ratio by dividing the measured resistance (when cells are attached to the electrodes) to the baseline resistance,
(2) finding or determining the maximum value in the resistance ratio over the frequency spectrum
(3) and taking a log-value (e.g. based on 10 or e=2.718) of the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In one example, the cell number index can be calculated by:
(1) at each measured frequency, calculating the reactance ratio by dividing the measured reactance (when cells are attached to the electrodes) to the baseline reactance,
(2) finding or determining the maximum value in the reactance ratio over the frequency spectrum
(3) and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In yet another example, the index can be calculated by:
(1) at each measured frequency, calculating the resistance ratio by dividing the measured resistance (when cells are attached to the electrodes) to the baseline resistance,
(2) then calculating the relative change in resistance in each measured frequency by subtracting one from the resistance ratio,
(3) then integrating all the relative-change value.

In this case, "cell-number index" is derived based on multiple-frequency points, instead of single peak-frequency like above examples. Again, a zero or near-zero "cell number index" indicates that on cells are present on the electrodes. A higher value of "cell number index" indicates that, for same type of the cells and cells under similar physiological conditions, more cells are attached to the electrodes.

It is worthwhile to point out that it is not necessary to derive such a "cell number index" for utilizing the impedance information for monitoring cell conditions over the electrodes. Actually, one may choose to directly use impedance values (e.g., at a single fixed frequency; or at a maximum relative-change frequency, or at multiple frequencies) as an indicator of cell conditions.

Still, it is preferred for the present invention to derive "cell number index" and use such index to monitor cell conditions. There are several advantages of using "cell number index" to monitor cell growth and/or attachment and/or viability conditions.

First, one can compare the performance of different electrode geometries by utilizing such cell number index.

Secondly, for a given electrode geometry, it is possible to construct "calibration curve" for depicting the relationship between the cell number and the cell number index by performing impedance measurements for different number of cells added to the electrodes (in such an experiment, it is important to make sure that the seeded cells have well-attached to the electrode surfaces). With such a calibration curve, when a new impedance measurement is performed, it is then possible to estimate cell number from the newly-measured cell number index.

Thirdly, cell number index can also be used to compare different surface conditions. For the same electrode geometry and same number of cells, a surface treatment given a larger cell number index indicates a better attachment for the cells to the electrode surface and/or better surface for cell attachment.

C. Devices and Methods for Monitoring Cell Migration or Growth

In yet another aspect, the present invention is directed to a device for monitoring cell migration or growth, which device comprises an nonconducting substrate comprising, on the surface of said substrate, a first area for cell attachment, surrounded by a second electrode area comprising at least two electrodes, wherein said first cell attachment area is separated from said second electrode area by a cell migration barrier, wherein removal of said barrier allows cell migration or growth from said first cell attachment area into said second electrode area, and said cell migration or growth results in a change of impedance between or among electrodes in said second electrode area.

The first cell attachment area can have any surface suitable for cell attachment. In addition, the first cell attachment area is modified with a cell-adhesion promotion moiety to increase the efficiency of cell attachment. Any suitable cell-adhesion promotion moieties, including the ones described in the above Section B, can be used in the present devices.

Figure 24:
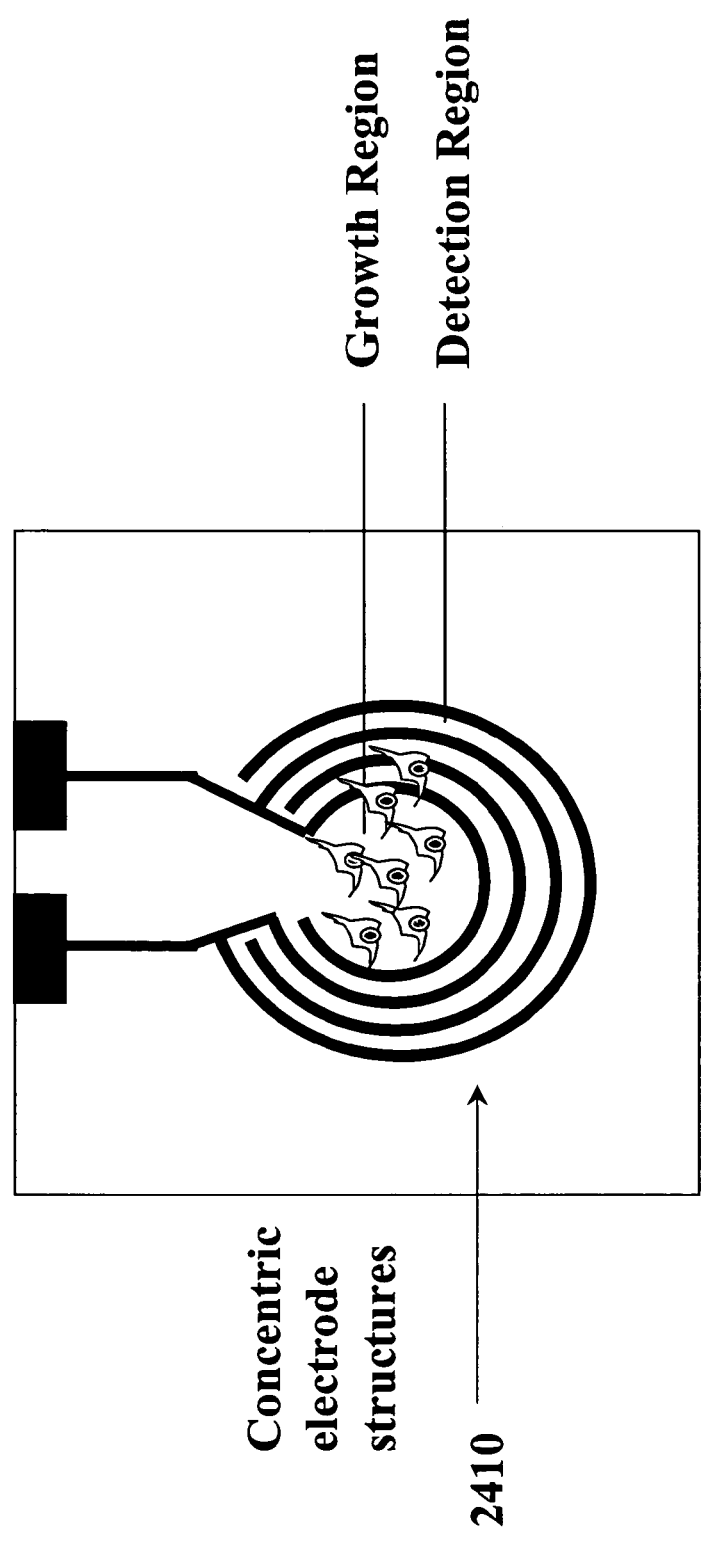
FIG. 24 is a schematic diagram for cell migration assay where the cells are initially grow on a growth region defined by a removable well plate (not shown on the Figure). The wall of the well in the plate is initially located either over the detection region or within the detection region. The plate is then removed. Cells are allowed to spread and migrate over to the detection region defined by the concentric electrode structures 2410.

The first cell attachment area and the second electrode area of present devices can have any suitable configurations. For example, as shown in FIG. 24, the first cell attachment area and the second electrode area are concentric.

Any suitable cell migration barrier can be used in the present devices. For example, the cell migration barrier can be a well that is made of polymer materials.

The impedance can be measured or analyzed in any suitable frequency range, e.g., in a frequency range between about 1 Hz and about 100 MHz, or between 10 Hz and 5 MHz.

In yet another aspect, the present invention is directed to a method for monitoring cell migration or growth, which method comprises: a) providing an above-described device for monitoring cell migration or growth; b) placing cells to be monitored on the first cell attachment area; c) removing the cell migration barrier and allowing migration or growth of said cells from the first cell attachment area into the second electrode area; and d) monitoring a change of impedance between or among electrodes in said second electrode area to monitor migration or growth of said cells.

The present methods can be used to monitor any suitable parameters that are related to migration or growth. For example, the present methods can further comprise determining the amount or number of cells that migrate or grow into the second electrode area.

The present methods can be used to determine weather a test compound can modulate, i.e., increase or decrease, migration or growth, or to screen for such a modulator. For example, the present methods can be conducted wherein the cell migration or growth is monitored in the presence and absence of a test compound and the method is used to determine whether said test compound modulates migration or growth of the cells. In another example, the present methods can be conducted wherein the cell migration or growth is stimulated by a migration or growth stimulator and the method is used to screen the test compound for an antagonist of said stimulator.

Measurement of length and numbers of neurites in cultivated neurons (cell lines or primary neuronal cell culture) under microscope is the only means by which neurite outgrowth has been studied. This measurement is very slow and subjective. By integrating the fluorescence labeling with fluorescent confocal microscopy and computational technology, the accuracy of the measurement has been significantly improved. However, the system is very expensive and fluorescent labeling is required. In addition, because of the slow workflow, this system is unable to meet large-scale studies.

The devices as described below allows for single neuron positioning and neurite outgrowth real-time measurement. The scale of the device or apparatus can be designed based on the requirement. For example, an apparatus for research purposes will be the low-density arrays and the assay will be semi-automated. An apparatus for high throughput screening for drug leads will be the high-density arrays, which fit the current screening system, and the assays will be fully automated. The software package allows basic measurement, calculation, and statistical analysis.

Accordingly, in yet another aspect, the present invention is directed to a device for monitoring neurite outgrowth, which apparatus comprises an nonconducting substrate comprising, on its surface, a center neuron anchoring area surrounded by a neurite growth detection area, wherein neurite growth detection area comprises at least two electrodes that are capable of generating a change of impedance between or among said electrodes when at least one of said electrodes is at least partially covered by said growing neuron. For example, a change of impedance can be generated when at least 1%, 5%, 10%, 20%, 30%, 40%, 50%, 60%, 70%, 80%, 90%, 95%, 99% or 100% of at least one of said electrodes is covered by said growing neuron.

The neuron anchoring area can have any surface suitable for cell attachment. In addition, the neuron anchoring area can be modified with a cell-adhesion promotion moiety to increase the efficiency of neuron anchoring. Any suitable cell-adhesion promotion moieties, including the ones described in the above Section B, can be used in the present apparatuses for monitoring neurite outgrowth.

Figure 25:
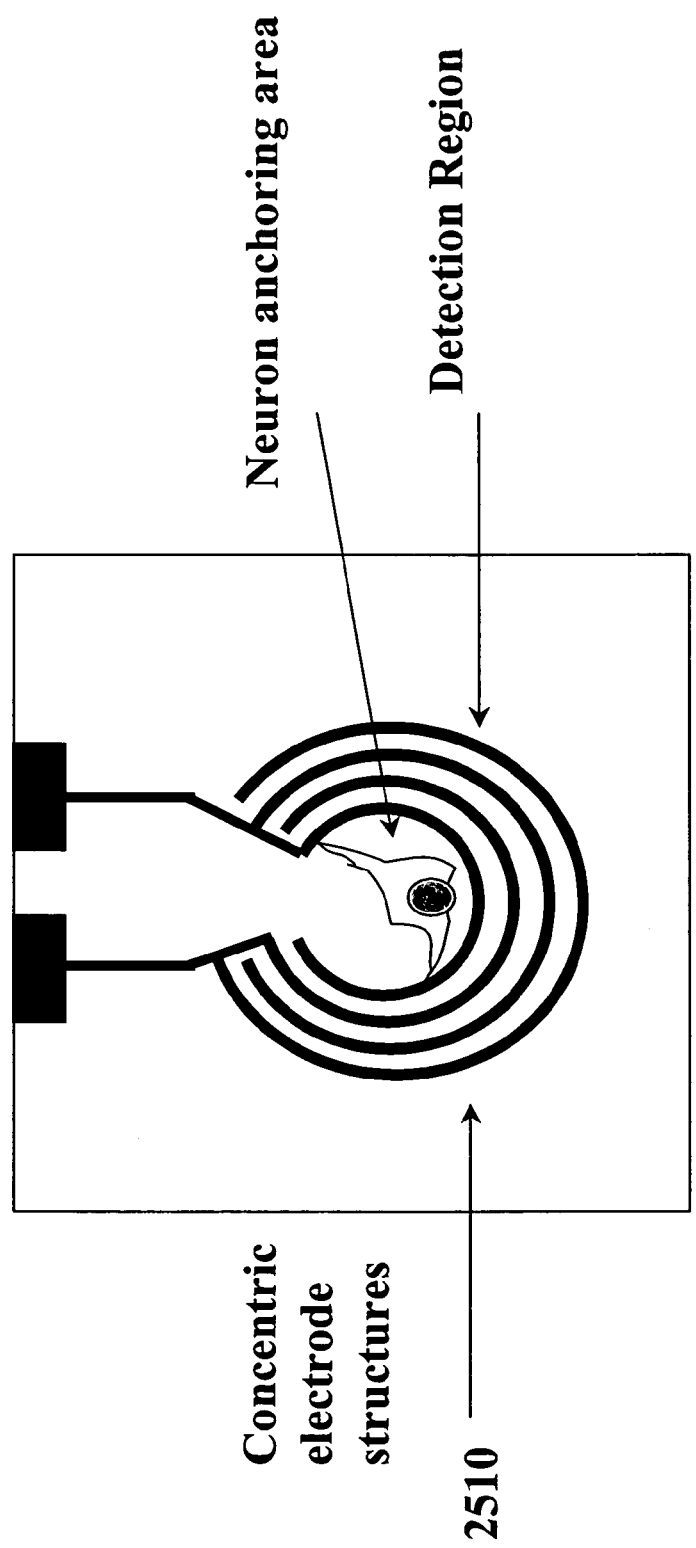
FIG. 25 is a schematic diagram for neurite outgrowth detection. A single neuron is initially located in the neuron anchoring area. The neuron outgrowth is monitored by impedance change between the concentric electrode structures 2510 in the detection region.

The neuron anchoring area and the neurite outgrowth detection area of the present apparatuses can have any suitable configurations. For example, as shown in FIG. 25, the neuron anchoring area and the neurite outgrowth detection area can be concentric. In another example, the neuron anchoring area can be a center circular region and the neurite outgrowth detection areas comprise multiple circular or segment electrodes. In another example, the neuron anchoring area can be a center square region and the neurite outgrowth detection areas comprise multiple linear segment electrodes.

The present apparatuses can further comprise an impedance analyzer capable of monitoring a change of impedance between or among any two or more electrodes.

In yet another aspect, the present invention is directed to a method for monitoring neurite outgrowth, which method comprises: a) providing an above-described apparatus for monitoring neurite outgrowth, b) positioning a neuron to be monitored on the neuron anchoring area; c) allowing growth of said neuron from the neuron anchoring area into the neurite outgrowth detection area; and d) monitoring a change of impedance between or among electrodes in the neurite outgrowth detection area to monitor growth of said neuron.

The present methods can be used to monitor any suitable parameters that are related to neurite outgrowth. For example, the present methods can be used to monitor length and numbers of neurites in cultivated neurons. Although the present methods can be used to monitor neurite outgrowth of a single neuron, it is preferable to be used in high-throughput mode, e.g., to be used to monitor the outgrowth of a plurality of neurons simultaneously.

The present methods can be used to determine weather a test compound can modulate, i.e., increase or decrease, neurite outgrowth, or to screen for such a modulator. For example, the present methods can be conducted wherein the neurite outgrowth is monitored in the presence and absence of a test compound and the method is used to determine whether said test compound modulates the neurite outgrowth. In another example, the present methods can be conducted wherein the neurite outgrowth is stimulated by a neurite outgrowth stimulator and the method is used to screen the test compound for an antagonist of said stimulator.

The following illustrates an example of the present apparatus and its operation. The apparatus comprises a solid substrate, on which a plurality of measurement units is incorporated. Each measurement unit comprises multiple electrodes, having appropriate geometrical relationships. The electrodes are capable of positioning individual neuron cells onto desired locations on the substrate surfaces when appropriate electrical signals are applied to the electrodes to produce positioning dielectrophoretic forces (e.g., see review by Wang X-B and Cheng J. "Electronic manipulation of cells on microchip-based devices" in Biochip Technology (eds: Cheng J and Kricka L), Harwood Academic Publishers, PA, U.S.A., pp 135-139). In one embodiment, the measurement unit comprises a center circular electrode, surrounded by multiple circular, segment electrodes. In another embodiment, the measurement unit comprises a center square electrode, surrounded by multiple linear segment electrodes. The apparatus may further comprise an impedance analyzer that is capable of determining the impedance between two sets of electrodes.

In use, the neuron cells at suitable concentrations are introduced onto the chip surface. Individual cells are positioned onto the center of measurement units with applying suitable electrical voltage signals. After the neuron cells landed and adhered onto the chip surface, electrical impedance between the electrodes within the microelectrode array is determined. The measured impedance values are used to derive information about the neurite outgrowth. When the axons and dendrites grown from the positioned neurons reach on to a particular electrode element, the electrical impedance at that electrode element is altered.

D. Apparatuses and Methods for Analyzing a Particle in a Microchannel

In yet another aspect, the present invention is directed to an apparatus for analyzing a particle, which apparatus comprises a substrate comprising a microchannel and a pair of electrodes located on opposite sides along said microchannel, each of said electrodes having a surface area that equals to or is less than twice the largest cross-sectional area of a particle to be analyzed, wherein passage of said particle through said electrode pair in said microchannel generates a change of impedance between said electrodes that can be used to analyze said particle.

The electrodes of the present apparatuses for analyzing a particle in a microchannel can have any suitable surface area, length or height. In one example, each of the electrodes can have a surface area that equals to or is less than the same, a half, or ten percent the largest cross-sectional area of a particle to be analyzed. In another example, each of the microelectrodes can have, along the length of the microchannel, a length that is substantially less than the largest single-dimension of a particle to be analyzed. In still another example, the electrodes can span the entire height of the microchannel.

The present apparatuses can have any suitable number of electrodes. In one example, the present apparatuses comprise two pairs of the electrodes, said two pairs are separated from each other along the length of the microchannel by a distance that equals to or is less than the largest single-dimension of a particle to be analyzed. Preferably, a change of impedance between the two pairs of the microelectrodes is measured.

In another example, the present apparatuses comprise three pairs of the electrodes, said three pairs separated from each other along the length of the microchannel, wherein the pairs of the electrodes on both ends are used to supply voltages and the pair of the electrodes in the middle is used to generate a change of electrode impedance. Preferably, the change of voltage between the middle pair and an end pair is monitored.

In still another example, the present apparatuses comprise four pairs of the microelectrodes, said four pairs separated from each other along the length of the microchannel, wherein the two pairs of the electrodes on both ends are used to supply voltages and the two pairs of the electrodes in the middle are used to generate a change of electrode impedance. Preferably, the change of voltage between one of the middle pairs and one of the end pairs is monitored.

The present apparatuses can further comprise an impedance analyzer.

In yet another aspect, the present invention is directed to a method for analyzing a particle, which method comprises: a) providing an above-described apparatus for analyzing a particle in a microchannel; b) allowing a particle to be analyzed to pass through the electrode pair in the microchannel to generate a change of impedance between said electrodes; and c) monitoring said change of impedance to analyze said particle.

The present methods can be used to monitor any suitable parameters of a particle. For example, the present methods can further comprise analyzing amount or number of particle(s). The present methods can be used to monitor any suitable particles.

The present methods can be used to monitor cells as well as non-cell particles. Exemplary cells include animal cells, plant cells, fungal cells, bacterial cells, recombinant cells and cultured cells. The present methods can be used to monitor any suitable parameters of a cell, e.g., the nucleic acid content of the cell. See Song at al., *Proc. Natl. Acad. Sci. U.S.A.*, 97(20): 10687-90 (2000). Preferably, the DNA content of the cell is monitored.

In yet another aspect, the present invention is directed to an apparatus for analyzing a particle, which apparatus comprises: a) a container suitable for containing a solution comprising a particle to be analyzed; and b) a membrane separating said container into two electrically isolated chambers, said membrane comprising an aperture having a pore size that equals to or is slightly larger than size of said particle and two electrodes suitable for detecting a change of impedance in said solution caused by a transit passage of said particle through said aperture.

The membrane of the present apparatuses can have any suitable thickness. In one example, the membrane can have a thickness from about 1 micron to about 100 microns. In another example, the membrane can have a thickness from about 5 micron to about 30 micron. In another example, the membrane can have a thickness that equals to or is smaller than a diameter of a particle to be analyzed.

The aperture of the present apparatuses can have any suitable pore size, depending on the size of the particles to be analyzed. For example, the aperture can have a pore size of about 2, 5, 10, 15, 20, 30, or 50 microns.

The two electrodes of the present apparatuses can have any suitable locations and configurations. In one example, the two electrodes can be located on the opposite sides of the membrane. In another example, the two electrodes can have a concentric dimension surrounding the aperture.

In one embodiment, the present apparatuses can comprise a plurality of membranes arranged in series to allow a particle to pass apertures of said membranes sequentially. In another embodiment, the present apparatuses can further comprise an impedance analyzer.

In yet another aspect, the present invention is directed to a method for analyzing a particle, which method comprises: a) providing an above-described apparatus; b) placing a solution comprising a particle to be analyzed in the container and allowing said particle to pass through the aperture; and c) detecting a change of impedance in said solution caused by the transit passage of said particle through said aperture to analyze said particle.

The present methods can be used to monitor any suitable parameters of a particle. For example, the present methods can be used to analyze size or dielectric property of the particle.

To facilitate analysis, the particle can be labeled with a nano-sized dielectric or electric moiety. Preferably, the nano-sized dielectric or electric moiety can comprise an antibody that specifically binds to the particle to be analyzed. Also preferably, the nano-sized dielectric or electric moiety can be a gold particle.

The present methods can be used to monitor cells as well as non-cell particles. Exemplary cells include animal cells, plant cells, fungal cells, bacterial cells, recombinant cells and cultured cells. The present methods can be used to monitor any suitable parameters of a cell, e.g., size, dielectric property, or viability of the cell. To facilitate analysis, the cell can be labeled with a nano-sized dielectric or electric moiety. Preferably, the nano-sized dielectric or electric moiety can comprise an antibody that specifically binds to the cell to be analyzed. Also preferably, the nano-sized dielectric or electric moiety can be a gold particle.

E. Systems and Methods for Monitoring Cell-substrate Impedance and Solution Conductivity In yet another aspect, the present invention is directed to systems and methods for monitoring cell-substrate impedance and solution conductivity. Any apparatuses, systems and methods for monitoring cell-substrate impedance, including the ones described in the above sections and those commonly known in the art, can be used in the present systems and methods. Any apparatuses, systems and methods for monitoring solution conductivity that are commonly known in the art can be used in the present systems and methods. See e.g., U.S. Pat. No. 6,235,520 B1.

In one embodiment, the present invention is directed to a system for monitoring cell-substrate impedance and solution conductivity, which system comprises: a) a substrate defining a plurality of discrete microwells on a substrate surface, each of said wells comprising an apparatus for monitoring cell-substrate impedance described in the above sections; and b) a means for measuring the conductance of a solution medium in each microwell, said means including (i) a pair of electrodes adapted for insertion into a well on said substrate, and (ii) electrical means for applying a low-voltage, AC signal across said electrodes when said electrodes are submerged in said medium, and (iii) electrical means for synchronously measuring the current across said electrodes, said system can be used to monitor attachment, growth or metabolic activity of cells contained in each well.

In another embodiment, the present invention is directed to a system for monitoring cell-substrate impedance and solution conductivity, which system comprises: a) a substrate defining a plurality of discrete microwells on a substrate surface, each of said wells comprising an apparatus for monitoring cell-substrate impedance described in the above sections; and b) a sub-system comprising: i) at least one pair of electrodes adapted for insertion into a first well on said substrate; and (ii) circuitry adapted for applying a low-voltage. AC signal across said first pair of electrodes when said electrodes are submerged in solution medium in said first well, and for synchronously measuring the current across said electrodes, said system can be used to monitor attachment, growth or metabolic activity of cells contained in each well.

In still another embodiment, the present invention is directed to a method for monitoring cell attachment, growth or metabolic activity, which method comprises: a) providing an above-described system for monitoring cell-substrate impedance and solution conductivity; b) placing a solution comprising cells to be monitored into at least one well of said system; and c) monitoring cell-substrate impedance and solution conductivity in said well to monitor attachment, growth or metabolic activity of cells contained in each well. Preferably, cells are monitored in multiple wells or all wells of the system simultaneously.

F. EXAMPLES

The following examples are intended to illustrate but not to limit the invention.

Example 1

Figure 26B:
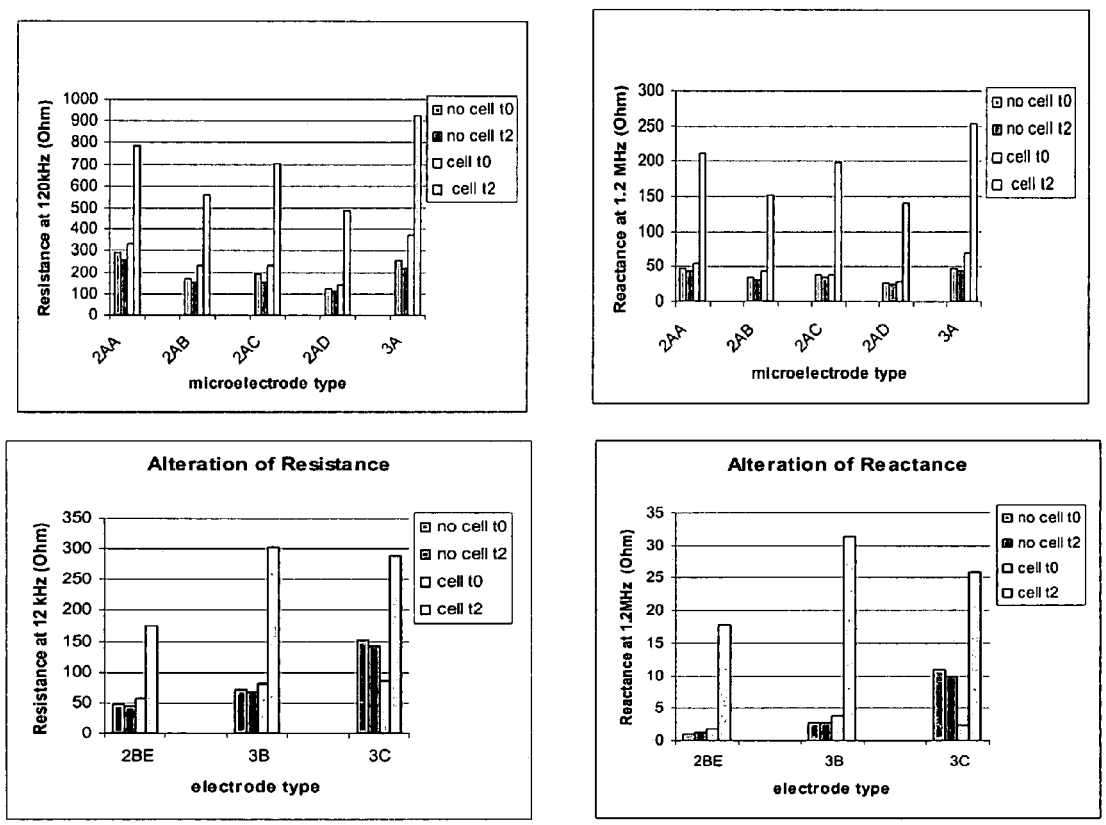
FIG. 26 illustrates resistance and reactance (mainly capacitive reactance) for 8 different types of electrodes attached with or without NIH 3T3 cells. The unit for both resistance and reactance is Ohm. The magnitudes of the reactance were plotted in a log-scale. Note that the polarity for the reactance at most of the frequencies was negative (capacitive reactance). In results shown in FIG. 26 through FIG. 32, different types of electrodes were fabricated in glass substrates (1 cm by 1 cm by 1 mm). The experimental devices for experiments were constructed by gluing bottom less, conical or cylinder shaped plastic tubes over glass substrates on which electrode structures were fabricated. Typically, the plastic tubes had diameter between 4.5 mm and 6.2 mm on the end that was glued onto the glass substrates. The glass substrates formed the bottom of the wells (or fluidic containers) and the plastic tubes form the wall of the wells (or fluidic containers). For experiments, suspensions of cells in media or media were added into the wells (or fluidic containers). Electrode structures on the substrate were used to measure impedance changes following cell attachment to the electrode surfaces to monitor cell attachment and/or growth in the wells (or fluidic containers).

Resistance and Capacitive Reactance for 8 Different Types of Electrodes Attached with or without Cells FIG. 26 illustrates resistance and reactance for 8 different types of electrodes attached with or without NIH 3T3 cells. The unit for both resistance and reactance is Ohm. The magnitudes of the reactance were plotted in a log-scale. Note that the polarity for the reactance at most of the frequencies was negative (capacitive reactance). The diameter of the electrode for 2AA, 2AB, 2AC, 2AD, and 3A is 1 mm; the diameter of the electrode for 2BE, 3B and 3C is 3 mm. The features of each electrode types are different and are summarized in Table 1. The surfaces of electrodes were coated with chemical and biological molecules. In this experiment, fibronectin was used. After coating, NIH 3T3 cells were then seeded onto the surfaces of the electrodes. The resistance and reactance (capacitive reactance) were measured at 0 hour (immediately after seeding the cells) and at two hours after the seeding. (A, B) Resistance and capacitive reactance as a function of frequency for eight different types of electrode geometry. Increase in resistance and decrease in capacitive reactance were seen in all five electrode types attached with NIH 3T3 (2 hours after seeding the cells), compared with their corresponding microelectrodes on which cells were not attached (0 hour after seeding the cells) as indicated. (B) The bar graph summarizes the resistance and capacitive reactance changes at a given frequency as indicated. Here, the capacitive reactance value is the absolute value. Changes of resistance and capacitive reactance were only seen in the electrodes attached with NIH 3T3 cells.

TABLE 1 summary of some of the electrodes that have been tested.

| Electrode Structure Name | Substrate Material | Electrode Structure Type | Dimension (micron) | Diameter of active area |
|---|---|---|---|---|
| 2CF | Glass | Interdigitated | 48/28 | 6 mm |
| 2BE | Glass | Interdigitated | 48/18 | 3 mm |
| 2AA | Glass | Interdigitated | 80/50 | 1 mm |
| 2AB | Glass | Interdigitated | 80/15 | 1 mm |
| 2AC | Glass | Interdigitated | 50/30 | 1 mm |
| 2AD | Glass | Interdigitated | 50/10 | 1 mm |
| 3C | Glass | Circle-on-line | 60/160/180 | 3 mm |
| 3B | Glass | Circle-on-line | 30/80/90 | 3 mm |
| 3A | Glass | Circle-on-line | 30/80/90 | 1 mm |
|  | Plastics (Kapton) | Interdigitated | 50/50 |  |

Electrodes 2AA, 2AB, 2AC, 2AD, 2BE and 2CF are interdigitated electrodes and have values 80/50, 80/15, 80/30, 50/10, 48/18 and 48/28 for electrode width and gap width, respectively.
Electrodes 3A, 3B and 3C are circle-on-stick (or circle on a line) electrodes having 30/80/90, 30/80/90 and 60/160/180 for the stick (i.e. line) width and stick (i.e. line) gap, electrode circle diameter, respectively.}

Example 2

Quantitative Measurement of Cells Using the 3B Electrode

Figure 27:
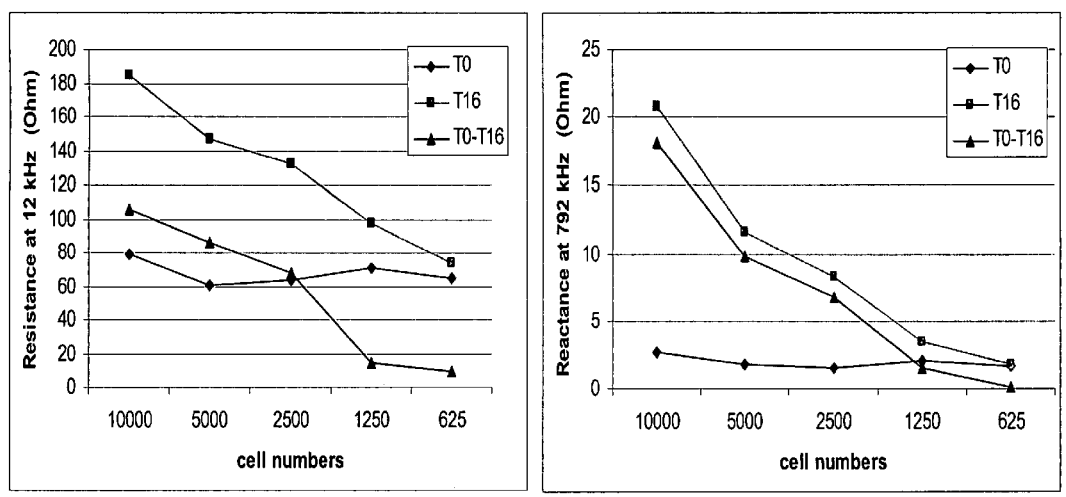
FIG. 27 illustrates quantitative measurement of cells using the electrode structures of 3B geometry.

FIG. 27 illustrates quantitative measurement of cells using the electrodes of 3B geometry. The apparatuses for experiments were constructed by gluing bottom less, conical or cylinder shaped plastic tubes over glass substrates on which 3B electrodes were fabricated. The plastic tubes had a diameter of about 5.5 mm on the end that was glued onto the glass substrates. The glass substrates formed the bottom of the wells (or fluidic containers) and the plastic tubes form the wall of the wells (or fluidic containers). Serial diluted NIH 3T3 cells (10,000 cells, 5,000 cells, 2,500 cells, 1,250 cells and 625 cells) were added into the apparatuses and onto the surface of the 3B electrodes that had been coated with fibronectin. Resistance and reactance were measured at 0 hour (immediately after seeding), and at 16 hours after seeding. The curves represent resistance and capacitive reactance data from a given frequency as indicated. Note that the polarity for the reactance at the frequency of 792 kHz was negative (capacitive reactance) and the magnitudes of the reactance were shown. $T_0$ curve indicates the baseline resistance and capacitive reactance for the electrodes onto which cells had not been attached. T0-T16 curve indicates the resistance and capacitive reactance changes after cell attached to the electrodes. The current 3B electrode is able to sense less than 600 cells. The dynamic quantification range of the current 3B electrode is between 10,000 and 500 for NIH 3T3 cells.

Example 3

Figure 28:
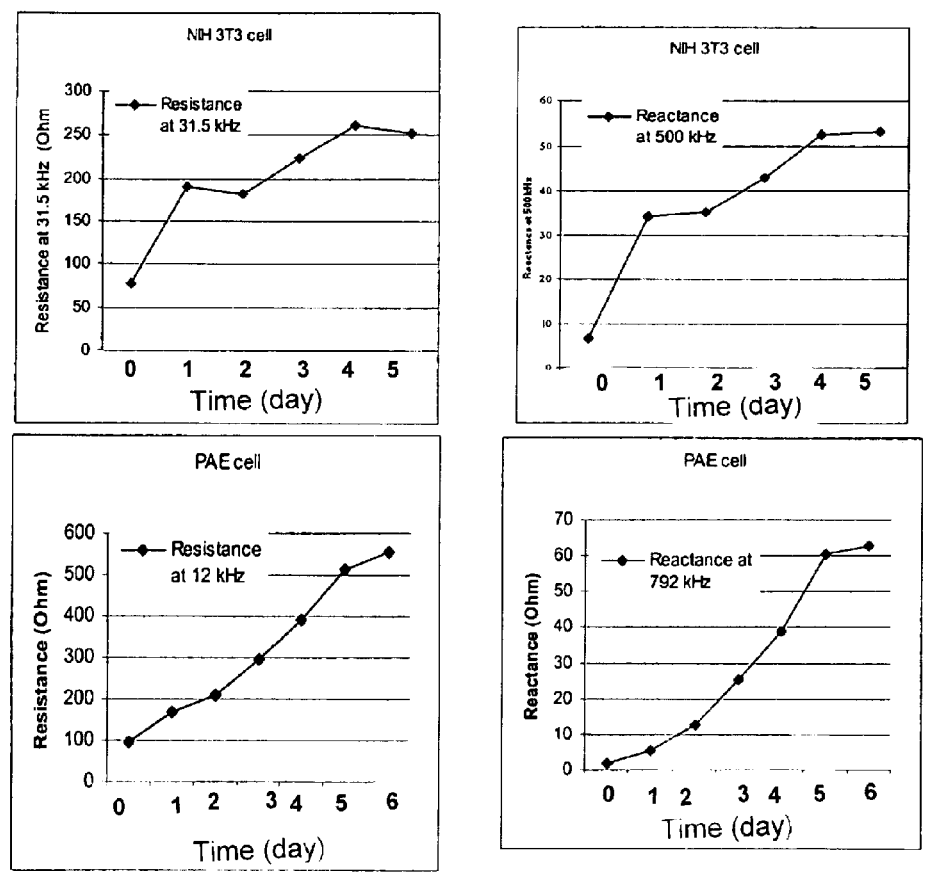
FIG. 28 illustrates real time monitoring of NIH 3T3 and PAE cell proliferation using the electrode structures of 3C and 3B geometry.

Real Time Monitoring of NIH 3T3 and PAE Cell Proliferation Using the 3C and 3B Electrodes FIG. 28 illustrates real time monitoring of NIH 3T3 and porcine aortic endothelia (PAE) cell proliferation using the 3C and 3B electrodes. The apparatuses for experiments were constructed using similar methods to those described for FIG. 26 and FIG. 27. Two thousand five hundred NIH 3T3 cells and 2,500 PAE cells were seeded onto the coated electrodes. For NIH 3T3 cells, the electrode was coated with fibronectin; for PAE cells, the electrode was coated with gelatin. Resistance and capacitive reactance were measured daily to monitor the cell proliferation. Note that the polarity for the reactance at the frequency of 792 kHz was negative (capacitive reactance) and the magnitudes of the reactance were shown. Day 0 indicates the measurement immediately after seeding of the cells. Here, the capacitive reactance value shown in the figure is the absolute value. The resistance and capacitive reactance increase with the cultivation time (days) in both cell types, indicating cell proliferation. The NIH 3T3 cell growth plateaued at day 4, while PAE cell growth plateaued at day 5, suggesting the NIH 3T3 cells proliferate faster than PAE.

Example 4

Figure 29:
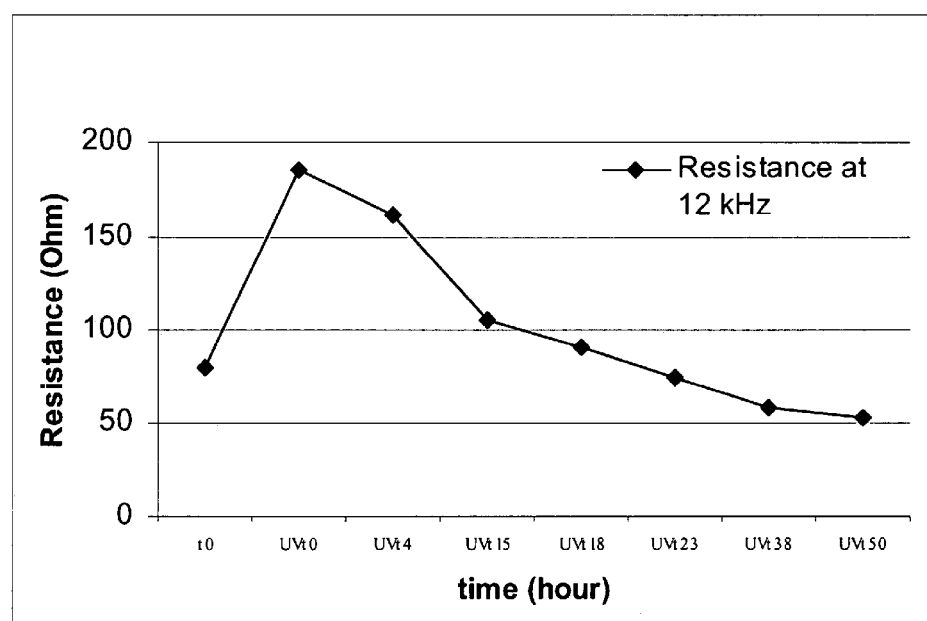
FIG. 29 illustrates real-time monitoring of NIH 3T3 cell death induced by ultraviolet (UV) using the electrode structures of 3B geometry.

Real-time Monitoring of NIH 3T3 Cell Death Induced by Ultraviolet (UV) Using the 3B Electrode FIG. 29 illustrates real-time monitoring of NIH 3T3 cell death induced by ultraviolet (UV) using the 3B electrode. The apparatuses for experiments were constructed using similar methods to those described for FIG. 26 and FIG. 27. Ten thousand NIH 3T3 cells were seeded onto a fibronectin-coated 3B electrode, and cultivated cells in 5% CO2 incubator till fully confluent. For UV exposure, the media on the cell monolayer was withdrawn and the cell layer was directly exposed to UV for five minutes. After UV exposure, the original media were then added back to the monolayer. Resistance and capacitive reactance were measured immediately, indicated as UVt0. The UV exposed electrode was then incubated in 5% C02 incubator and the cell death induced by UV was monitored by measuring resistance and capacitive reactance at different time intervals as indicated. The figure showed the resistance decline after UV exposure, indicating UV-induced cell death. The cell death can be detected as early as 4 hours after UV exposure and cell death rate reached to 100% at 23 hours after UV exposure. The cell death measured by resistance was correlated with cell morphology changes observed under a microscope (data not shown).

Example 5

$IC_{50}$s for Tamoxifen at Different Time Intervals

Figure 30:
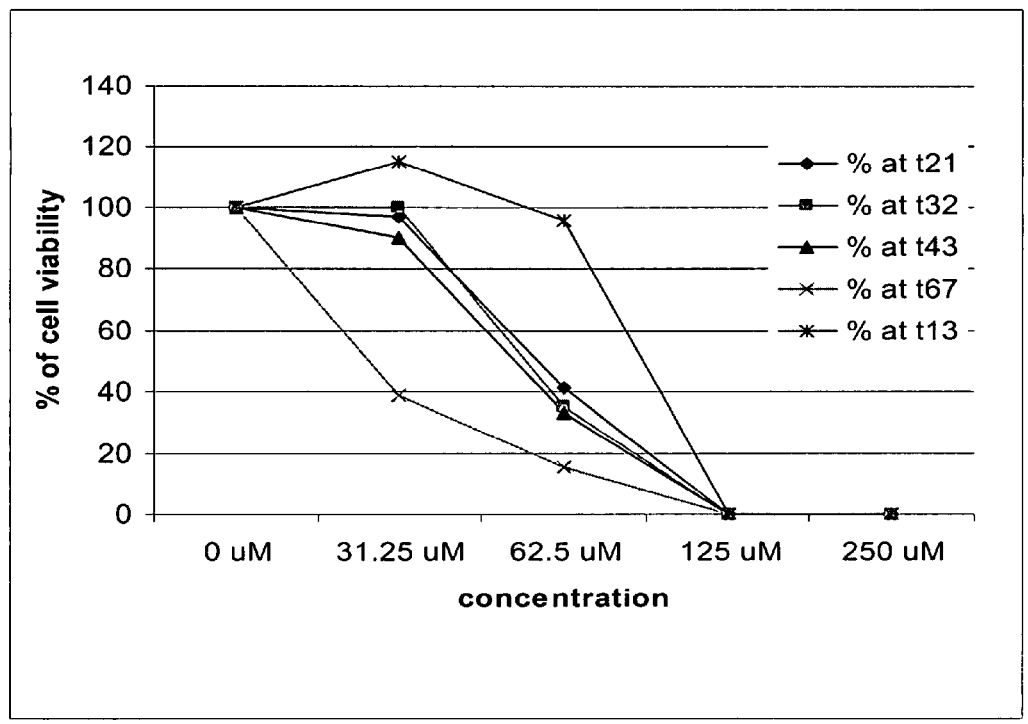
FIG. 30 illustrates $IC_{50}$s for tamoxifen toxicity effect at different time intervals.

FIG. 30 illustrates $IC_{50}$s for tamoxifen at different time intervals. $IC_{50}$s for Tamoxifen at different time intervals were measured by real-time monitoring of the cytotoxic effect of Tamoxifen on the NIH 3T3 cells. The 3C electrodes were used for the experiment. The apparatuses for experiments were constructed using similar methods to those described for FIG. 26 and FIG. 27. The electrodes were coated with fibronectin and seeded with 10,000 NIH 3T3 cells per electrode. Once the cells reached 100% confluence, a serially diluted Tamoxifen was added to the cells as indicated. Resistance and reactance of the treated cell-electrode interface were measured at different time intervals. The percentage of cell viability was calculated as following:

% of cell viability=$100*(R_{t0}-R_{tx})/(R_{t0\_ctrl}-R_{tx\_ctrl})$ where $R_{t0}$ and $R_{tx}$ is resistance of the resistance of a treated electrode at T0 and at a given time interval, and $R_{t0\_ctrl}$ and $R_{tx\_ctrl}$ is the resistance of the control electrode at T0 and at the same time interval. Here the resistance used for the calculation was the value measured for a particular frequency (31 kHz). As shown in the figure, the IC50s at the 21 hour interval (t21), the 32 hour interval (t32) and the 43 hour interval (t43) are similar, while IC50s at the 13 hour (t13) and the 67 hour (t67) intervals are significantly different. This strongly suggests that appropriated treatment time for a given chemical compound is crucial to determine an accurate IC50. Monitoring of cytotoxic effect by real-time measuring resistance changes between the cell and the electrode showed the great advantages to obtain accurate IC50s.

Example 6

Resistance Comparison Among Four Different Cell Types Using the 3C Electrode

Figure 31:
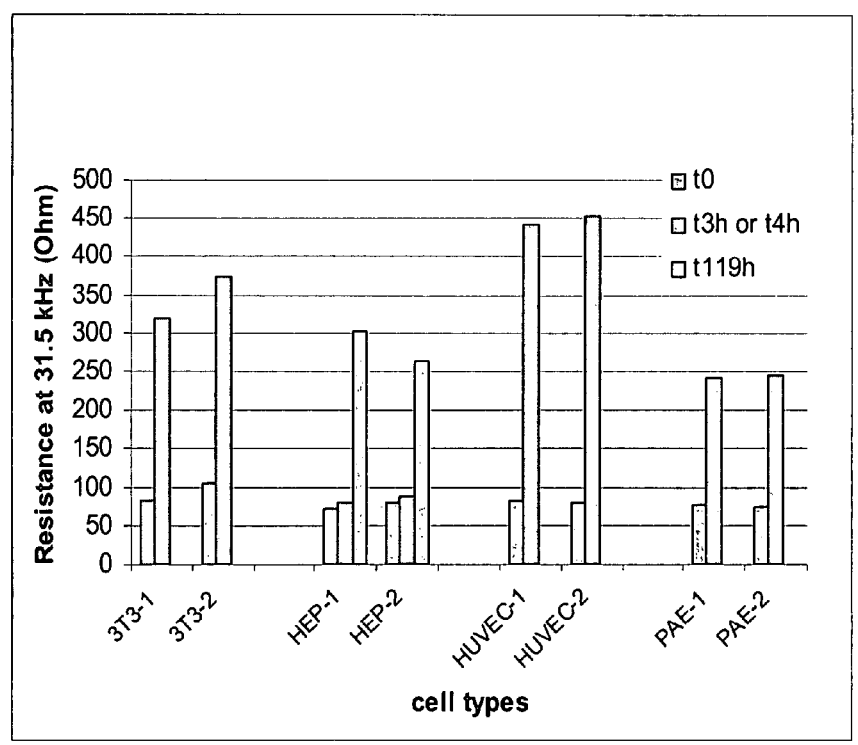
FIG. 31 illustrates impedance comparison among four different cell types using the electrode structures of 3C geometry.

FIG. 31 illustrates resistance comparison among four different cell types using the 3C electrode. Resistance for four cell types were measured using the 3C electrode. The apparatuses for experiments were constructed using similar methods to those described for FIG. 26 and FIG. 27. The four cell types were the NIH 3T3 cells (mouse fibroblasts), the HEP-G2 cells (human hepatocytes), the PAE cells (pig endothelia cells) and the HUVEC (human endothelia cells). For the NIH 3T3 and the HEP-G2, the electrode was coated with fibronectin; for the PAE and HUVEC, the electrode was coated with gelatin. Two electrodes were used for each cell type as indicated. For NIH 313 and HEP-G2, 10,000 cells were seeded onto each electrode; for HUVEC and PAE, 20000 cells were seeded onto each electrode. The resistance and capacitive reactance were measured (only resistance data were shown here) at time 0 and 3 or 4 hours after seeding. For HEP-G2, resistance was measured at 119 hours after seeding. Significant increases in resistance were seen in NIH 3T3 cells, HUVEC and PAE cells at 3 or 4 hours. In contrast, subtle increase in resistance was seen in HEP-G2 at 4 hours after seeding, indicating the slow attachment of hepatocytes to the electrodes. The resistance for HEP-G2 increased steadily after overnight incubation (data not shown) and reached to plateau at 119 hour after seeding.

Example 7

Reproducibility of Resistance Measurement

Figure 32:
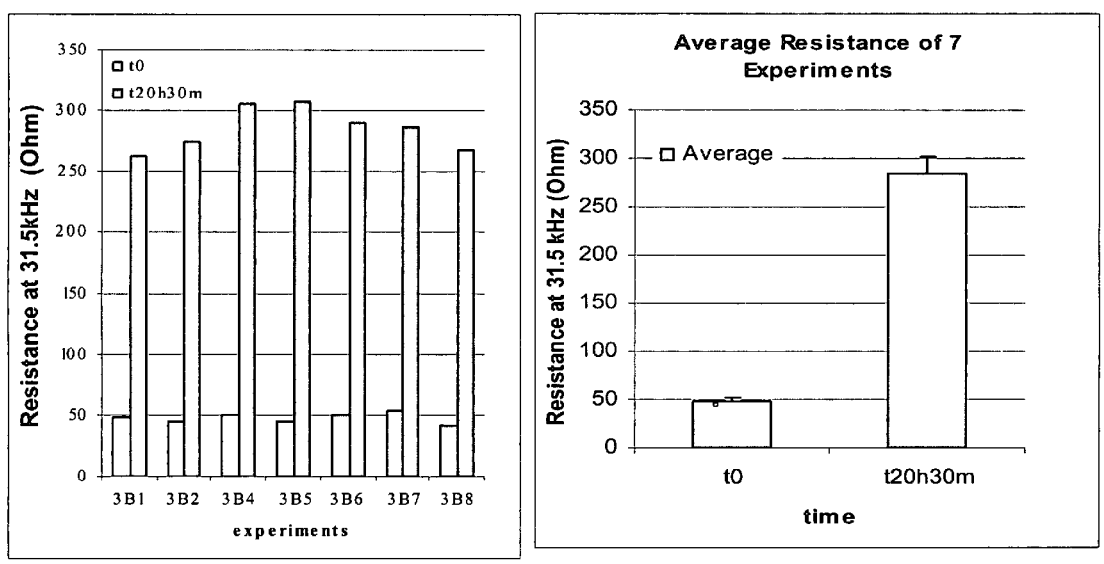
FIG. 32 illustrates reproducibility of impedance measurement.
Figure 33:
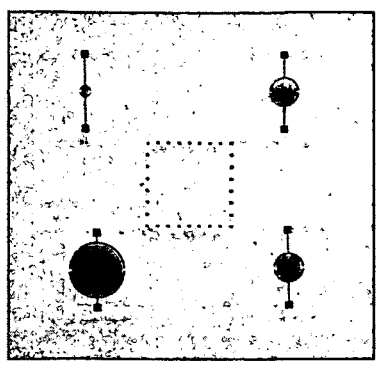
FIG. 33 illustrates five representative designs of the electronic cell chips having electrode structures fabricated on a substrate. The gold electrodes (thickness of ~0.2 micron) over a chromium seeding layer (thickness of ~30 nm) with different geometries and sizes are fabricated in the central region of the glass substrate. The size of the glass substrates is 1 cm×1 cm. The electrode structures on the substrates can be connected to electric detection interface (i.e., impedance measurement circuits or an impedance analyzer) via connection electrode pads located on the sides of the glass substrate.
Figure 34:
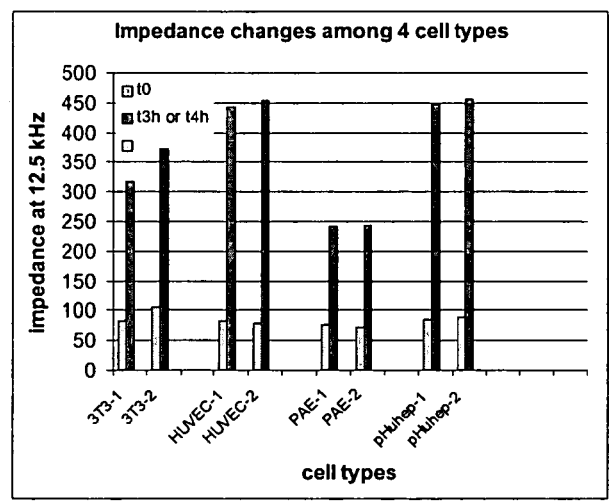
FIG. 34 illustrates detection or measurement of 4 different cell types on the testing devices. The 4 cell types were the NIH 3T3 cells (mouse fibroblasts), the PAE cells (porcine aortic endothelia), HUVEC (human endothelia cells), and pHuhep (primary human hepatocytes). For NIH 3T3, and pHuhep cells, the electrodes were coated with fibronectin; for the PAE and HUVEC, the electrodes were coated with gelatin. For each cell type, two devices were used as indicated. The resistance was measured at 0 and 3 or 4 hours after seeding. Significant increases in resistance were seen in NIH 3T3 cells, HUVEC, PAE, and pHuhep cells at 3 or 4 hours. Similar to the experimental devices used to obtain results shown in FIG. 26 through FIG. 32, the testing devices used to obtain the results shown in FIG. 34 (and FIG. 35 through FIG. 37) were constructed by gluing bottom less, conical or cylinder shaped plastic tubes over glass substrates on which electrode structures were fabricated. The glass substrates formed the bottom of the wells (or fluidic containers) and the plastic tubes form the wall of the wells (or fluidic containers). For experiments, suspensions of cells in media or media were added into the wells (or fluidic containers). Electrode structures on the substrate were used to measure impedance changes following cell attachment to the electrode surfaces to monitor cell attachment and/or growth in the wells (or fluidic containers).
Figure 35:
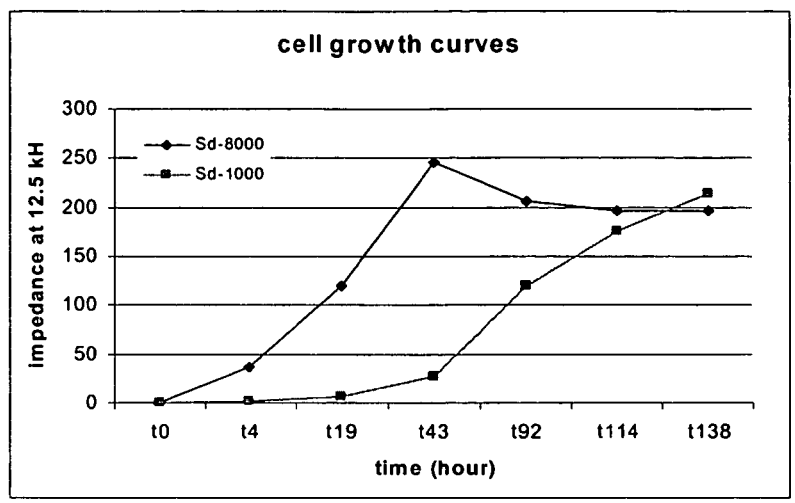
FIG. 35 illustrates real time monitoring of PAE cell proliferation on the testing devices. Cells were seeded onto the coated electrodes at different densities (8,000 cells and 1,000 cells). Resistance and reactance were measured at different time intervals as indicated to monitor the cell proliferation. "t0" indicates the measurement immediately after seeding of the cells. The resistance value increases with the cultivation time at both cell seeding densities, indicating cell proliferation. The cells with a high seeding density proliferated much faster than cells with a lower seeding density. Sd: seeding density.
Figure 36:
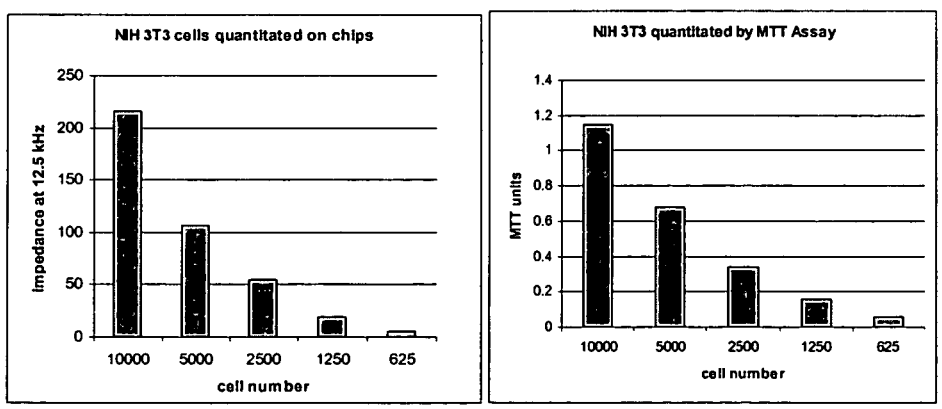
FIG. 36 illustrates quantitative measurement of cells on the testing devices and by MTT assay. Serially diluted NIH 3T3 cells (10,000 cells, 5,000 cells, 2,500 cells, 1,250 cells and 625 cells) were added either to the testing devices coated with fibronectin or a 96-well plate. For the assay using devices, impedance was measured at 16 hours after seeding. For MTT assay, cells were stained with MTT dye at 16 hours after seeding and then read on an ELISA plate reader at 540 nm. As shown in the figure, the device can quantitatively measure cell number changes. The results from both methods are almost identical.
Figure 37:
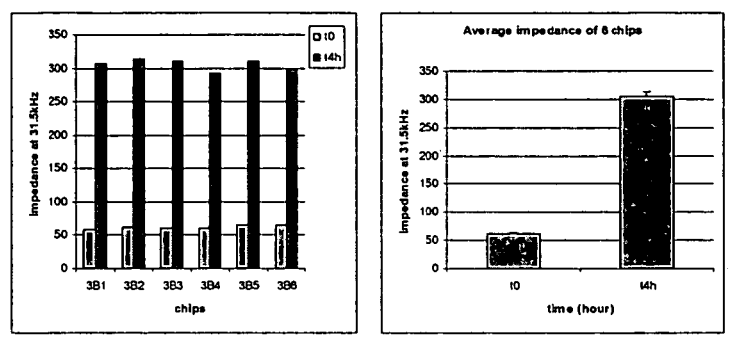
FIG. 37 illustrates reproducibility of resistance measurement on the testing devices. The reproducibility was tested on 6 devices seeded with primary human hepatocytes. The resistance for each electrode was measured immediately after seeding (t0), and 4 hours after the seeding. Significant increase in resistance values was seen in all devices after 4 hour incubation indicating the cell attachment and spreading onto electrode surfaces (and other regions of the substrate surfaces). The CV for t0 is 4.3% and for t4 h is 2.7% as shown in the right hand side panel.

FIG. 32 illustrates reproducibility of resistance measurement. The reproducibility was tested on seven electrodes (3B) seeded with HUVEC. The apparatuses for experiments were constructed using similar methods to those described for FIG. 26 and FIG. 27. The electrodes were coated with gelatin and seeded with 15,000 HUVEC cells per electrode. The resistance for each electrode was measure immediately after seeding ($t_o$), and 20 hours and 30 minutes after seeding. Significant increase in resistance was seen after 20 hour incubation indicating the cell attachment onto electrode. The average resistance for t) is 47.4 with standard deviation of 3.9; for t20 h30 m, the average resistance is 284.8 with standard deviation of 17.2. The coefficient of variance for to is 8.3%, and for t20 h30 m is 6.1.

We claim:

1. A method of making a device for detecting cells on an electrode surface through measurement of impedance change resulting from attachment of cells on the electrode surface, comprising:
   a) providing a non-conductive substrate with a deposited electrically conductive metal film;
   b) patterning said electrically conductive metal film using laser ablation of said conductive film from said substrate to form an array of electrodes, wherein each electrode comprises at least two electrode structures having a thickness up to 230 nm and that permit impedance measurement at each electrode structure, wherein each electrode structure comprises a plurality of electrode elements; and
   c) cleaning said substrate with an acid or base solution to remove re-deposition of ablated conductive material;
   d) connecting said electrode structures to a surface of said substrate opposite said electrode structures with a means for electronic connection selected from the group consisting of a flex circuit, metal clips, electrically conductive lines formed through said substrate, electrical wires and electrically conductive paste filled holes; and
   e) assembling said substrate to a bottomless multi-well plate to form an electrode-containing multi-well plate; wherein said electrode structures are positioned within wells of said multi-well plate.

2. The method according to claim 1, wherein said non-conductive substrate is constructed from a material selected from the group consisting of glass, a polymer, a plastic, a ceramic, fiberglass, and a combination thereof.

3. The method according to claim 1, wherein said electrically conductive metal film is constructed from a material selected from the group consisting of gold, chromium, nickel, copper, platinum, aluminum, sliver, steel, indium-tin-xide, and a combination thereof.

4. The method according to claim 1, wherein said electronic connection means comprises a PCB board with downward-facing straight-line conductor lines, wherein one end of said conductor lines is conductively bonded to connection pads on said substrate and the other end can be accessed from the bottom.

5. The method according to claim 1, wherein said electronic connection means comprises a flex circuit wrapped around edges of said substrate, wherein one end of said flex circuit comprises metal wires conductively bonded to connection pads on said substrate.

6. The methods according to claim 1, wherein said electronic connection means comprises metal clips that connect electrode pads on the top side of said substrate to the bottom side of said substrate.

7. The method according to claim 1, wherein said electronic connection means comprises wire bonding that connects connection pads located on said substrate to a PCB board comprising conductive vias, wherein said PCB board is accessible from the bottom side.

8. The method according to claim 1, wherein said electronic connection means comprises conductive-pasted-filled holes, further wherein the step of connecting said electrode structures further comprises producing holes at determined locations of said substrate and filling said holes with conductive paste.

9. The method according to claim 1, wherein the cleaning step further comprises mechanical scrubbing of the substrate.

10. The method according to claim 1, wherein said multi-well plate is selected from the group consisting of a 3 well, 12 well, 24 well, 48 well, 96 well, 192 well, 384 well, 768 well and 1536 well plate.

11. The method according to claim 1, wherein said electrode structures with electrode elements comprising com rise a geometry selected from the group consisting of circle-on-line, diamond-on-line, and castellated.

12. The method according to claim 1, wherein the widths of said electrode elements are from 20 microns to 500 microns.

13. The method according to claim 1, wherein a gap between electrode elements of different electrode structures is between about 3 microns and about 80 microns.

14. The method according to claim 1, wherein said electrode structures with electrode elements comprise an interdigitated geometry or sinusoidal geometry.

* * * * *